US012274167B2

(12) United States Patent
Ding et al.

(10) Patent No.: US 12,274,167 B2
(45) Date of Patent: Apr. 8, 2025

(54) ORGANIC ELECTROLUMINESCENT MATERIALS AND DEVICES

(71) Applicant: BEIJING SUMMER SPROUT TECHNOLOGY CO., LTD., Beijing (CN)

(72) Inventors: Hualong Ding, Beijing (CN); Chi Yuen Raymond Kwong, Beijing (CN); Chuanjun Xia, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 796 days.

(21) Appl. No.: 17/378,429

(22) Filed: Jul. 16, 2021

(65) Prior Publication Data
US 2022/0020935 A1    Jan. 20, 2022

(30) Foreign Application Priority Data

Jul. 20, 2020   (CN) .......................... 202010698126.6
Jun. 30, 2021   (CN) .......................... 202110716169.7

(51) Int. Cl.
H01L 51/50    (2006.01)
C07D 263/32   (2006.01)
(Continued)

(52) U.S. Cl.
CPC ......... H10K 85/656 (2023.02); C07D 263/32 (2013.01); C07D 413/14 (2013.01);
(Continued)

(58) Field of Classification Search
None
See application file for complete search history.

(56) References Cited

U.S. PATENT DOCUMENTS 5,703,436 A    12/1997 Forrest et al.
5,707,745 A    1/1998 Forrest et al.
(Continued)

FOREIGN PATENT DOCUMENTS

CN    105176519 A    12/2015
CN    107629034 A    1/2018
(Continued)

OTHER PUBLICATIONS

Suzuki et. al., Synthesis and characterization of novel strong electron acceptors: bithiazole analogues of etracyanodiphenoquinodimethane (TCNDQ); 2000; Tetrahedron Letters 41 (2000) 8359-8364 (Year: 2000).*

(Continued)

Primary Examiner — Gregory D Clark
(74) Attorney, Agent, or Firm — ArentFox Schiff LLP; Joseph M. Maraia; Marlo Schepper Grolnic

(57) ABSTRACT

Disclosed are a novel organic electroluminescent material and a device thereof. Such a novel organic electroluminescent material has a structure of Formula 1, and when applied to the organic electroluminescent device, can improve the balance of electrons and holes in the organic electroluminescent device and thus bring excellent device effects such as the improvement of external quantum efficiency, current efficiency, and service life. The novel organic electroluminescent material can be used to prepare organic semiconductor devices and is suitable for different types of organic semiconductor devices, including but not limited to fluorescent OLEDs, phosphorescent OLEDs, white OLEDs, laminated OLEDs, OTFTs, OPVs, etc. Further disclosed are an electroluminescent device comprising the organic electroluminescent material and a compound formulation comprising the organic electroluminescent material.

27 Claims, 2 Drawing Sheets

(51) Int. Cl.
| | |
|---|---|
| *C07D 413/14* | (2006.01) |
| *H10K 85/60* | (2023.01) |
| *H10K 50/15* | (2023.01) |
| *H10K 50/17* | (2023.01) |
| *H10K 50/19* | (2023.01) |

(52) U.S. Cl.
CPC .......... *H10K 85/654* (2023.02); *H10K 50/15* (2023.02); *H10K 50/17* (2023.02); *H10K 50/19* (2023.02)

(56) References Cited

U.S. PATENT DOCUMENTS

| | | | |
|---|---|---|---|
| 5,844,363 | A | 12/1998 | Gu et al. |
| 6,097,147 | A | 8/2000 | Baldo et al. |
| 6,303,238 | B1 | 10/2001 | Thompson et al. |
| 7,279,704 | B2 | 10/2007 | Walters et al. |
| 7,968,146 | B2 | 6/2011 | Wagner et al. |
| 2003/0230980 | A1 | 12/2003 | Forrest et al. |
| 2004/0174116 | A1 | 9/2004 | Lu et al. |
| 2015/0349273 | A1 | 12/2015 | Hung et al. |
| 2016/0359122 | A1 | 12/2016 | Boudreault et al. |
| 2017/0012215 | A1 | 1/2017 | Miyashita et al. |
| 2019/0181349 | A1 | 6/2019 | Xia |
| 2020/0062778 | A1 | 2/2020 | Cui et al. |
| 2021/0167298 | A1 | 6/2021 | Pang et al. |
| 2022/0020935 | A1 | 1/2022 | Ding et al. |
| 2022/0140252 | A1 | 5/2022 | Ding et al. |

FOREIGN PATENT DOCUMENTS

| | | | |
|---|---|---|---|
| JP | H0338578 | A | 2/1991 |
| JP | 2008169125 | A | 7/2008 |
| JP | 2021070681 | A | 5/2021 |
| KR | 1020170003472 | A | 1/2017 |
| KR | 1020170079357 | A | 7/2017 |
| KR | 1020230010023 | A | 1/2023 |
| WO | 2016124694 | A1 | 8/2016 |

OTHER PUBLICATIONS

Kaepplinger et. al., Barton-Kellogg Olefination of Conjugated Dithioxo Compounds; Sulfur Letters, Aug. 2003, vol. 26, pp. 141-147 (Year: 2003).*
Al-Ahmad et al., "New Family of Redox-Active Heterocycles," J. Amer. Chem. Soc. 117(3), pp. 1145-1146, DOI:10.1021/ja00108a038 (1995).
Office Action dated Dec. 23, 2022, for related CN Application No. 202110716169.7 (24 Pages).
Office Action dated Feb. 3, 2023, for related JP Application No. 2021-119068 (12 Pages).
Office Action dated Apr. 3, 2023, for related KR Application No. 10-2021-0094718 (16 Pages).
RN 115606-23-0, Registry, STN Columbus (2 Pages).
RN 116153-37-8, Registry, STN Columbus (3 Pages).
Notice of Second Review Opinion in CN Application No. 202110716169.7 dated Jul. 6, 2023, with English translation, 8 pages.
Written Decision on Registration in KR Application No. 10-2021-0094718 dated Aug. 22, 2023, with English translation, 6 pages.
Albert et al., "Rational Design of Molecules with Large Hyperpolarizabilities. Electric Field, Solvent Polarity, and Bond Length Alternation Effects on Merocyanine Dye Linear and Nonlinear Optical Properties," J. Phys. Chem. 100, pp. 9714-9725 (1996).
English translation and German language version of Office Action in DE Application No. 10 2021 118 596.3, dated Apr. 28, 2022 (14 pps.).
Ishida et al., "Novel Electron Acceptors Bearing a Heteroquinonoid System III: 2,5-Bis(dicyanomethylene)-2,5-dihydrofuran and Its Conjugated Homologues as Novel Oxygen-Containing Electron Acceptors," Bull. Chem. Soc. Jpn. 63(10), pp. 2828-2835 (1990).
Khodair et al., "A new approach to the synthesis of substituted 4-imidazolidinones as potential antiviral and antitumor agents," Tetrahedron 54(19), pp. 4859-4872 (1998).
Koyioni et al., "Synthesis of 5,5'-Diaryliminio Quinoidal 2,2'-Bithiazoles," Org. Lett. 19, pp. 174-177, DOI:10.1021/acs.orglett.6b03474 (2017).
Machine Translation and German-language version of Wikipedia entry "Nucleophilia," dated Apr. 9, 2020 (8 pps.).
Nandi et al., "Theoretical study of static second-order nonlinear optical properties of push-pull heteroquinonoid dimers," J. Mol. Structure: Theochem 760, pp. 235-244 (2006).
Suzuki, K. et al., "Synthesis and characterization of novel strong electron acceptors: bithiazole analogues of tetracyanodiphenoquinodimethane (TCNDQ)," Tetrahedron Letters 41, pp. 8359-8364 (2000).
Tang et al., "Organic electroluminescent diodes," Appl. Phys. Lett. 51(12), pp. 913-915 (1987).
Turkevich et al., "[Synthesis of an] Asymmetric Thiazolidine-2,4-dione azine," Khimiya ta Biologiya 32(6), 7 pps. (1970).
Uoyama et al., "Highly efficient organic light-emitting diodes from delayed fluorescence," Nature 492, pp. 234-240 (Dec. 2012).
Wang et al., "Conjugated electron donor-acceptor molecules with (E)-[4,40-biimidazolylidene]-5,50(1H,10H)-dione for new organic semiconductors," J. Mater. Chem. C. 2, pp. 1149-1157 (2014).
Wang et al., "New alternating electron donor-acceptor conjugated polymers entailing (E)-[4,40-biimidazolylidene]-5,50(1H,10H)-dione moieties," Polym. Chem. vol. 4, iss. 20, pp. 5283-5290, DOI:10.1039/C3PY00129F (2013).
English translation of Office Action in JP Application No. 2021-119068, dated Sep. 2, 2022 (6 pgs.).

* cited by examiner

ORGANIC ELECTROLUMINESCENT MATERIALS AND DEVICES

CROSS-REFERENCE TO RELATED APPLICATION(S)

This application claims priority to Chinese Patent Application No. CN202010698126.6 filed on Jul. 20, 2020 and Chinese Patent Application No. CN202110716169.7 filed on Jun. 30, 2021, the disclosure of which are incorporated herein by reference in their entireties.

TECHNICAL FIELD

The present disclosure relates to a novel organic electroluminescent material and a device thereof. More particularly, the present disclosure relates to an organic electroluminescent material having a structure of Formula 1, an electroluminescent device containing the material, and a compound formulation containing the material.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This device laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since the OLED is a self-emitting solid state device, it offers tremendous potential for display and lighting applications. In addition, the inherent properties of organic materials, such as their flexibility, may make them well suited for particular applications such as fabrication on flexible substrates.

The OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of the fluorescent OLED is only 25%. This limitation hindered the commercialization of OLED. In 1997, Forrest and Thompson reported phosphorescent OLED, which uses triplet emission from heavy metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. A small molecule refers to any organic or organometallic material that is not a polymer. The molecular weight of the small molecule can be large as long as it has well defined structure. Dendrimers with well-defined structures are considered as small molecules. Polymer OLEDs include conjugated polymers and non-conjugated polymers with pendant emitting groups. Small molecule OLED can become the polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of the OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

The organic light-emitting display device uses a hole injection layer and an electron injection layer to promote charge injection, wherein the hole injection layer is a functional layer formed by a single material or more than one material. The method using a single material generally uses materials with a deep LUMO, such as HATCN. The method using more than one material is formed by doping a P-type, deep-LUMO material with a hole transporting material. This mode can generate migrated holes (free carriers) by doping base materials (generally hole transporting materials) with a dopant, and can improve the hole injection ability of the anode and change the Fermi level of the device. The deep-LUMO material is generally a conjugated system compound with one or more strong electron-withdrawing substituents. It is difficult to synthesize the deep-LUMO material because the deep-LUMO material has strong electron-withdrawing substituents, and meanwhile, it is difficult for the deep-LUMO material to have properties of deep LUMO, high stability, and high film formation. For example, F4-TCNQ (a p-type hole injection material) has a deep LUMO, but its evaporation temperature is too low, which affects the deposition control, the reproducibility of production performance, and the thermal stability of devices. For example, HATCN has the problem of film formation in devices because of its strong crystallinity, and its LUMO is not deep enough to be used as p-type doping. Since the hole injection layer has a great impact on the voltage, efficiency, and lifetime of the OLED device, it is very important and urgent to develop a deep-LUMO material with high stability and high film formation in the industry. The present disclosure provides a series of novel organic electroluminescent materials with a dehydrogenated ring structure. These materials have LUMO energy levels with different depths and suitable evaporation temperature and thus can be used as a hole injection layer independently and an excellent P-type dopant.

K. Suzuki, M. Tomura, S. Tanaka, and Y. Yamashita disclose a compound having bithiophene and bithiazole structures in *Tetrahedron Letter,* 2000, 41, 8359-8364, wherein the specific structure of the compound is

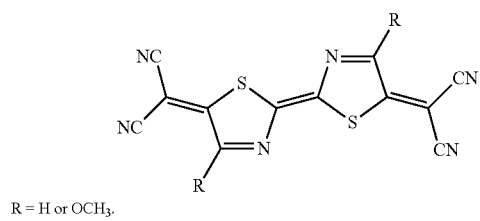

R = H or OCH$_3$.

However, this document does not disclose or teach any properties and applications of the compound when R is other groups.

P. K. Nandi, K. Mandal, and T. Kar, J. disclose a compound having a bithiophene structure in *Molecular Structure: THEOCHEM,* 2006, 760, 235-244, wherein the specific structure of the compound is

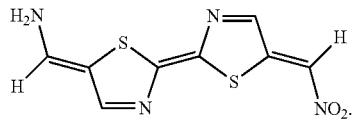 [SMILES: N/C=c1/cn/c(=c2/nc/c(=C/[N+](=O)[O-])s2)s1]

The research of this document focuses on the nonlinear optical properties and applications of the compound but does not disclose or teach the properties and applications of any compound having a substituent structure similar to the substituent structure of the present application.

H. Ishida, K. Yui, Y. Aso, T. Otsubo, and F. Ogura disclose a series of compounds having structures of thiophene, bithiophene, and the like in *Bull. Chem. Soc. Jpn.,* 1990, 63, 2828-2835, wherein specific examples of compounds are

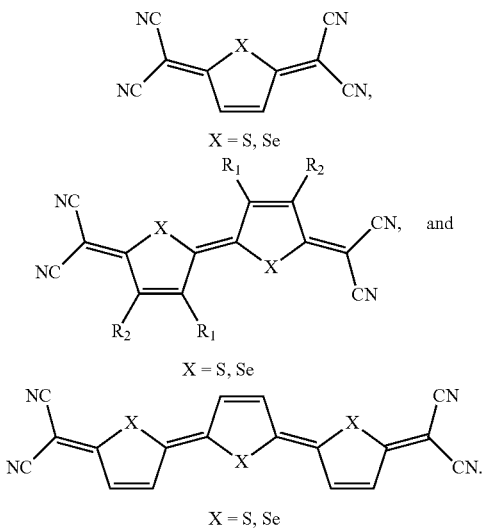

However, this document does not disclose or teach the properties and applications of any compound having a parent core structure similar to the parent core structure of the present application.

JPH0338578 discloses a class of compounds containing structures of bifuran, bithiophene, and the like as electron acceptors, and the disclosed general formula structure includes

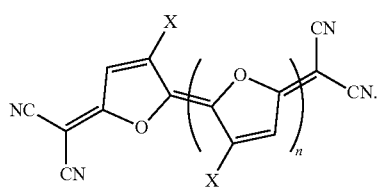

However, this application does not disclose or teach the properties and applications of any compound having a parent core structure similar to the parent core structure of the present application.

CN105176519 discloses a radialene compound containing a structure of thiazole, wherein the general structure formula of the compound is

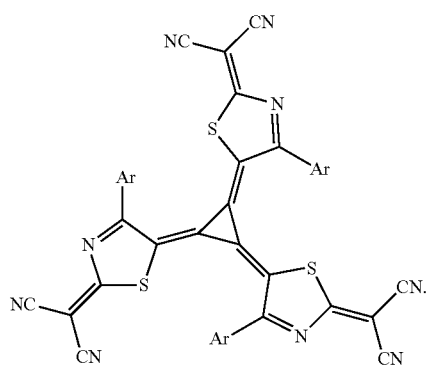

This application is concerned with the properties of compounds having the radialene structure but does not disclose or teach the properties and applications of any compound having a parent core structure similar to the parent core structure of the present application.

It is necessary to develop a hole injection material in organic electroluminescent materials, such material can improve the transport balance of electrons and holes and improve the device performance, and thus it is very important to develop novel high-performance hole injection materials.

SUMMARY

The present disclosure aims to provide a series of compounds having a structure of Formula 1 to solve at least part of the preceding problems.

According to an embodiment of the present disclosure, disclosed is a compound which has a structure represented by Formula 1:

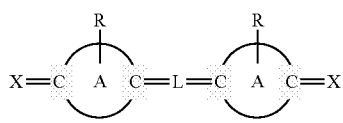

Formula 1 wherein

L is, at each occurrence identically or differently, selected from

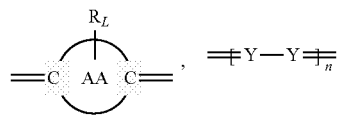

or any combination thereof;

ring AA is a conjugated structure having 4 to 30 ring atoms and at least one intra-ring double bond;

n is, at each occurrence identically or differently, selected from an integer from 0 to 10;

Y is, at each occurrence identically or differently, selected from the group consisting of $CR_L$ and N;

ring A is, at each occurrence identically or differently, a 5-membered heterocyclic ring, and the 5-membered heterocyclic ring comprises an intra-ring double bond, at least one N atom, and at least one W; W is, at each occurrence identically or differently, selected from the group consisting of O, S, Se, and $NR_N$;

X is, at each occurrence identically or differently, selected from the group consisting of Se, NR', and CR"R'";

R and $R_L$ represent, at each occurrence identically or differently, mono-substitution, multiple substitutions or non-substitution;

R, R', R", R'", $R_L$, and $R_N$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

when L is selected from

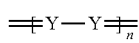

and n=0, at least one of substituents R and $R_N$ is a group having at least one electron-withdrawing group;

when X is selected from NR' or CR"R'", at least one of R', R", and R'" is a group having at least one electron-withdrawing group;

adjacent substituents R", R'" can be optionally joined to form a ring; and adjacent substituents R, $R_L$ can be optionally joined to form a ring; when adjacent substituents $R_L$ are joined to form a ring, the resulting ring has at least 4 ring atoms; and when adjacent substituents R are joined to form a ring, the resulting ring has at least 6 ring atoms.

According to another embodiment of the present disclosure, further disclosed is an electroluminescent device which includes the compound described in the preceding embodiment.

According to another embodiment of the present disclosure, further disclosed is a compound formulation which includes the compound described in the preceding embodiment.

The compound having the structure of Formula 1 disclosed in the present application can be applied to the organic electroluminescent device and can improve the balance of electrons and holes in the device, thereby bringing excellent device effects such as the improvement of external quantum efficiency, current efficiency, and lifetime. The compound can be used to prepare semiconductor devices and is suitable for different types of semiconductor devices, including but not limited to fluorescent OLEDs, phosphorescent OLEDs, white OLEDs, laminated OLEDs, OTFTs, OPVs, etc.

DETAILED DESCRIPTION

Figure 1:
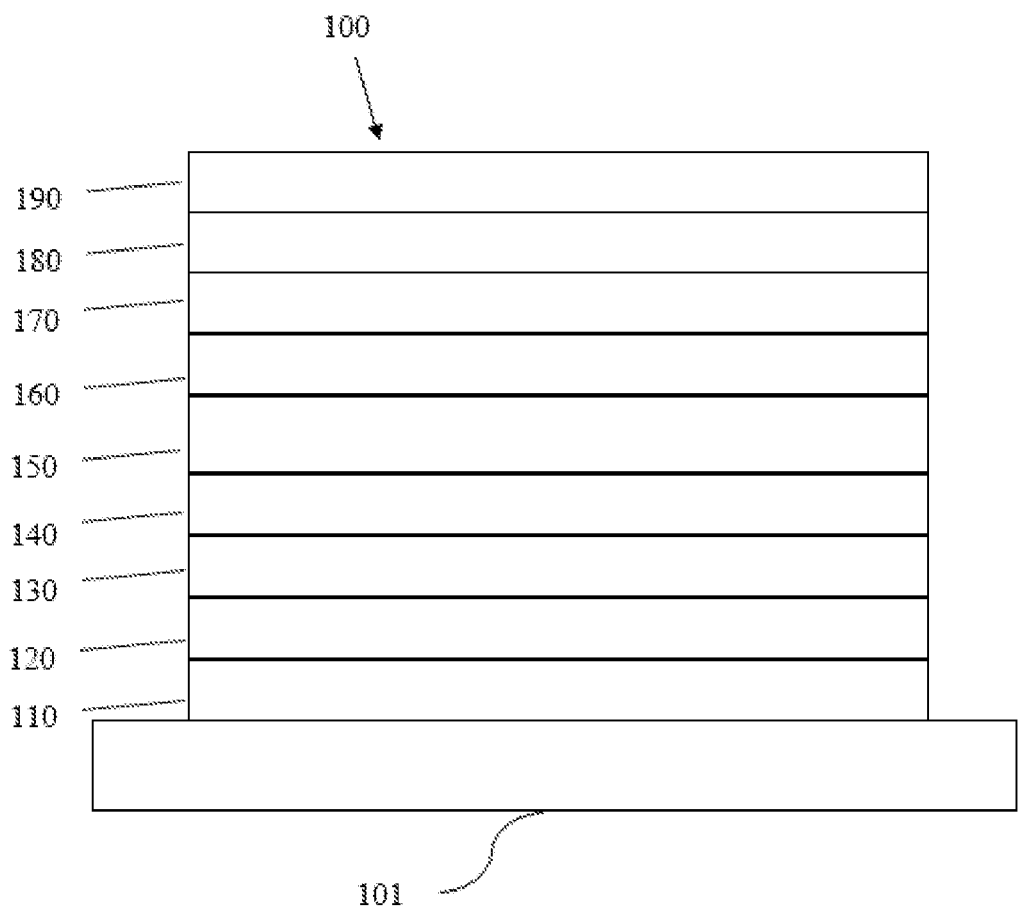
FIG. 1 is a schematic diagram of an organic light-emitting apparatus that may include a compound and a compound formulation disclosed by the present disclosure.

OLEDs can be fabricated on various types of substrates such as glass, plastic, and metal foil. FIG. 1 schematically shows an organic light emitting device 100 without limitation. The figures are not necessarily drawn to scale. Some of the layers in the figures can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transport layer is m-MTDATA doped with F4-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transport layer is BPhen doped with Li at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers are described in more detail in U.S. Pat. No. 6,097,147 and U.S. Patent Application Publication No. 2003/0230980, which are incorporated by reference herein in their entireties. Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting examples. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may comprise a single layer or multiple layers.

Figure 2:
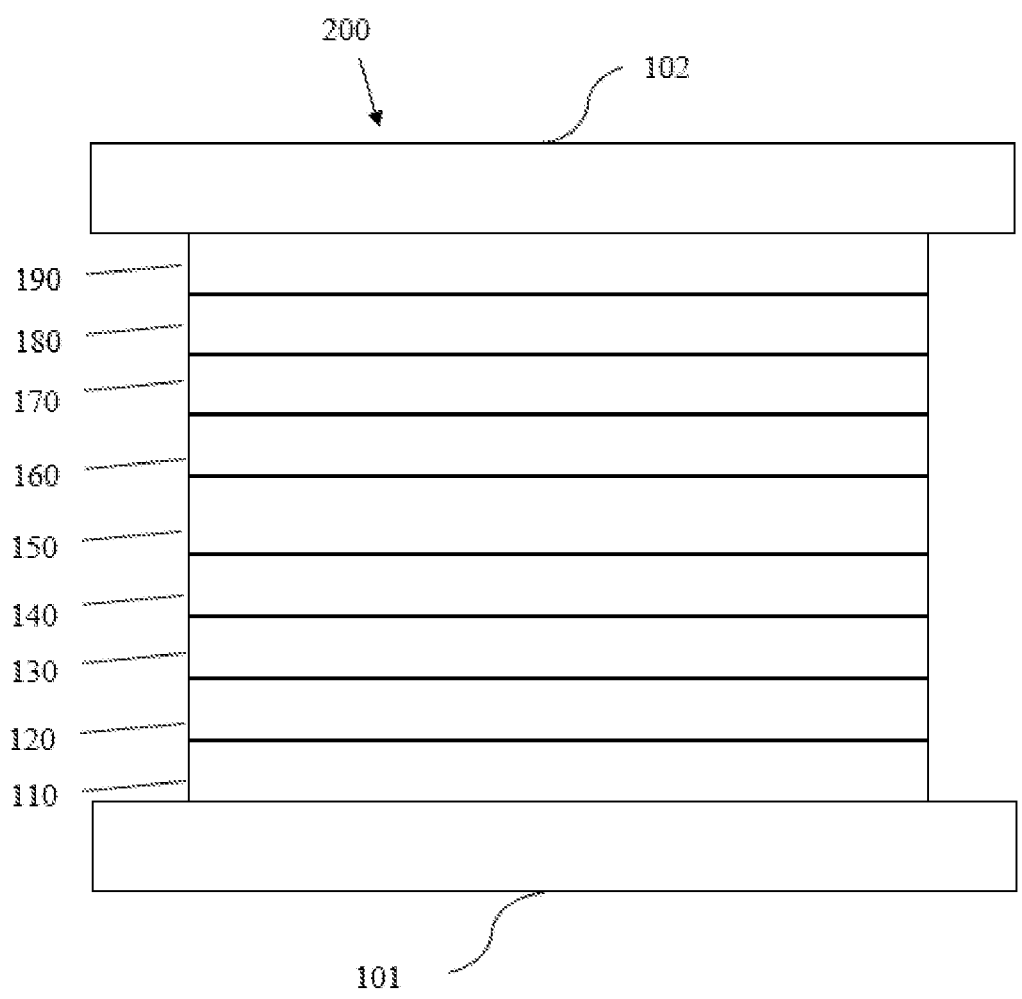
FIG. 2 is a schematic diagram of another organic light-emitting apparatus that may include a compound and a compound formulation disclosed by the present disclosure.

An OLED can be encapsulated by a barrier layer. FIG. 2 schematically shows an organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass or organic-inorganic hybrid layers. The barrier layer should be placed directly or indirectly outside of the OLED device. Multilayer thin film encapsulation was described in U.S. Pat. No. 7,968,146, which is incorporated by reference herein in its entirety.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from the substrate. There may be other layers between the first and second layers, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing (RISC) rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is generally characterized as a donor-acceptor charge-transfer (CT) type emission. The spatial separation of the HOMO and LUMO in these donor-acceptor type compounds generally results in small $\Delta E_{S-T}$. These states may involve CT states. Generally, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—as used herein includes both straight and branched chain alkyl groups. Alkyl may be alkyl having 1 to 20 carbon atoms, preferably alkyl having 1 to 12 carbon atoms, and more preferably alkyl having 1 to 6 carbon atoms. Examples of alkyl groups include a methyl group, an ethyl group, a propyl group, an isopropyl group, a n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group. Of the above, preferred are a methyl group, an ethyl group, a propyl group, an isopropyl group, a n-butyl group, an s-butyl group, an isobutyl group, a t-butyl group, an n-pentyl group, a neopentyl group, and an n-hexyl group. Additionally, the alkyl group may be optionally substituted.

Cycloalkyl—as used herein includes cyclic alkyl groups. The cycloalkyl groups may be those having 3 to 20 ring carbon atoms, preferably those having 4 to 10 carbon atoms. Examples of cycloalkyl include cyclobutyl, cyclopentyl, cyclohexyl, 4-methylcyclohexyl, 4,4-dimethylcyclohexyl, 1-adamantyl, 2-adamantyl, 1-norbornyl, 2-norbornyl, and the like. Of the above, preferred are cyclopentyl, cyclohexyl, 4-methylcyclohexyl, and 4,4-dimethylcyclohexyl. Additionally, the cycloalkyl group may be optionally substituted.

Heteroalkyl—as used herein, includes a group formed by replacing one or more carbons in an alkyl chain with a hetero-atom(s) selected from the group consisting of a nitrogen atom, an oxygen atom, a sulfur atom, a selenium atom, a phosphorus atom, a silicon atom, a germanium atom, and a boron atom. Heteroalkyl may be those having 1 to 20 carbon atoms, preferably those having 1 to 10 carbon atoms, and more preferably those having 1 to 6 carbon atoms. Examples of heteroalkyl include methoxymethyl, ethoxymethyl, ethoxyethyl, methylthiomethyl, ethylthiomethyl, ethylthioethyl, methoxymethoxymethyl, ethoxymethoxymethyl, ethoxyethoxyethyl, hydroxymethyl, hydroxyethyl, hydroxypropyl, mercaptomethyl, mercaptoethyl, mercaptopropyl, aminomethyl, aminoethyl, aminopropyl, dimethylaminomethyl, trimethylsilyl, dimethylethylsilyl, dimethylisopropylsilyl, t-butyldimethylsilyl, triethylsilyl, triisopropylsilyl, trimethylsilylmethyl, trimethylsilylethyl, and trimethylsilylisopropyl. Additionally, the heteroalkyl group may be optionally substituted.

Alkenyl—as used herein includes straight chain, branched chain, and cyclic alkene groups. Alkenyl may be those having 2 to 20 carbon atoms, preferably those having 2 to 10 carbon atoms. Examples of alkenyl include vinyl, 1-propenyl group, 1-butenyl, 2-butenyl, 3-butenyl, 1,3-butandienyl, 1-methylvinyl, styryl, 2,2-diphenylvinyl, 1,2-diphenylvinyl, 1-methylallyl, 1,1-dimethylallyl, 2-methylallyl, 1-phenylallyl, 2-phenylallyl, 3-phenylallyl, 3,3-diphenylallyl, 1,2-dimethylallyl, 1-phenyl-1-butenyl, 3-phenyl-1-butenyl, cyclopentenyl, cyclopentadienyl, cyclohexenyl, cycloheptenyl, cycloheptatrienyl, cyclooctenyl, cyclooctatetraenyl, and norbornenyl. Additionally, the alkenyl group may be optionally substituted.

Alkynyl—as used herein includes straight chain alkynyl groups. Alkynyl may be those having 2 to 20 carbon atoms, preferably those having 2 to 10 carbon atoms. Examples of alkynyl groups include ethynyl, propynyl, propargyl, 1-butynyl, 2-butynyl, 3-butynyl, 1-pentynyl, 2-pentynyl, 3,3-dimethyl-1-butynyl, 3-ethyl-3-methyl-1-pentynyl, 3,3-diisopropyl-1-pentynyl, phenylethynyl, phenylpropynyl, etc. Of the above, preferred are ethynyl, propynyl, propargyl, 1-butynyl, 2-butynyl, 3-butynyl, 1-pentynyl, and phenylethynyl. Additionally, the alkynyl group may be optionally substituted.

Aryl or an aromatic group—as used herein includes non-condensed and condensed systems. Aryl may be those having 6 to 30 carbon atoms, preferably those having 6 to 20 carbon atoms, and more preferably those having 6 to 12 carbon atoms. Examples of aryl groups include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Examples of non-condensed aryl groups include phenyl, biphenyl-2-yl, biphenyl-3-yl, biphenyl-4-yl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-(2-phenylpropyl)phenyl, 4'-methylbiphenylyl, 4"-t-butyl-p-terphenyl-4-yl, o-cumenyl, m-cumenyl, p-cumenyl, 2,3-xylyl, 3,4-xylyl, 2,5-xylyl, mesityl, and m-quarterphenyl. Additionally, the aryl group may be optionally substituted.

Heterocyclic groups or heterocycle—as used herein include non-aromatic cyclic groups. Non-aromatic heterocyclic groups includes saturated heterocyclic groups having 3 to 20 ring atoms and unsaturated non-aromatic heterocyclic groups having 3 to 20 ring atoms, where at least one ring atom is selected from the group consisting of a nitrogen atom, an oxygen atom, a sulfur atom, a selenium atom, a silicon atom, a phosphorus atom, a germanium atom, and a boron atom. Preferred non-aromatic heterocyclic groups are those having 3 to 7 ring atoms, each of which includes at least one hetero-atom such as nitrogen, oxygen, silicon, or sulfur. Examples of non-aromatic heterocyclic groups include oxiranyl, oxetanyl, tetrahydrofuranyl, tetrahydropyranyl, dioxolanyl, dioxanyl, aziridinyl, dihydropyrrolyl, tetrahydropyrrolyl, piperidinyl, oxazolidinyl, morpholinyl, piperazinyl, oxepinyl, thiepinyl, azepinyl, and tetrahydrosilolyl. Additionally, the heterocyclic group may be optionally substituted.

Heteroaryl—as used herein, includes non-condensed and condensed hetero-aromatic groups having 1 to 5 hetero-atoms, where at least one hetero-atom is selected from the group consisting of a nitrogen atom, an oxygen atom, a sulfur atom, a selenium atom, a silicon atom, a phosphorus atom, a germanium atom, and a boron atom. A hetero-aromatic group is also referred to as heteroaryl. Heteroaryl may be those having 3 to 30 carbon atoms, preferably those having 3 to 20 carbon atoms, and more preferably those having 3 to 12 carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridoindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4- azaborine, borazine, and aza-analogs thereof. Additionally, the heteroaryl group may be optionally substituted.

Alkoxy—as used herein, is represented by —O-alkyl, —O-cycloalkyl, —O-heteroalkyl, or —O-heterocyclic group. Examples and preferred examples of alkyl, cycloalkyl, heteroalkyl, and heterocyclic groups are the same as those described above. Alkoxy groups may be those having 1 to 20 carbon atoms, preferably those having 1 to 6 carbon atoms. Examples of alkoxy groups include methoxy, ethoxy, propoxy, butoxy, pentyloxy, hexyloxy, cyclopropyloxy, cyclobutyloxy, cyclopentyloxy, cyclohexyloxy, tetrahydrofuranyloxy, tetrahydropyranyloxy, methoxypropyloxy, ethoxyethyloxy, methoxymethyloxy, and ethoxymethyloxy. Additionally, the alkoxy group may be optionally substituted.

Aryloxy—as used herein, is represented by —O-aryl or —O-heteroaryl. Examples and preferred examples of aryl and heteroaryl are the same as those described above. Aryloxy groups may be those having 6 to 30 carbon atoms, preferably those having 6 to 20 carbon atoms. Examples of aryloxy groups include phenoxy and biphenyloxy. Additionally, the aryloxy group may be optionally substituted.

Arylalkyl—as used herein, contemplates alkyl substituted with an aryl group. Arylalkyl may be those having 7 to 30 carbon atoms, preferably those having 7 to 20 carbon atoms, and more preferably those having 7 to 13 carbon atoms. Examples of arylalkyl groups include benzyl, 1-phenylethyl, 2-phenylethyl, 1-phenylisopropyl, 2-phenylisopropyl, phenyl-t-butyl, alpha-naphthylmethyl, 1-alpha-naphthylethyl, 2-alpha-naphthylethyl, 1-alpha-naphthylisopropyl, 2-alpha-naphthylisopropyl, beta-naphthylmethyl, 1-beta-naphthyl ethyl, 2-beta-naphthyl ethyl, 1-beta-naphthylisopropyl, 2-beta-naphthylisopropyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, and 1-chloro-2-phenylisopropyl. Of the above, preferred are benzyl, p-cyanobenzyl, m-cyanobenzyl, o-cyanobenzyl, 1-phenylethyl, 2-phenylethyl, 1-phenylisopropyl, and 2-phenylisopropyl. Additionally, the arylalkyl group may be optionally substituted.

Alkylsilyl—as used herein, contemplates a silyl group substituted with an alkyl group. Alkylsilyl groups may be those having 3 to 20 carbon atoms, preferably those having 3 to 10 carbon atoms. Examples of alkylsilyl groups include trimethylsilyl, triethylsilyl, methyldiethylsilyl, ethyldimethylsilyl, tripropylsilyl, tributylsilyl, triisopropylsilyl, methyldiisopropylsilyl, dimethylisopropylsilyl, tri-t-butylsilyl, triisobutylsilyl, dimethyl t-butylsilyl, and methyldi-t-butylsilyl. Additionally, the alkylsilyl group may be optionally substituted.

Arylsilyl—as used herein, contemplates a silyl group substituted with an aryl group. Arylsilyl groups may be those having 6 to 30 carbon atoms, preferably those having 8 to 20 carbon atoms. Examples of arylsilyl groups include triphenylsilyl, phenyldibiphenylylsilyl, diphenylbiphenylsilyl, phenyldiethylsilyl, diphenylethylsilyl, phenyldimethylsilyl, diphenylmethylsilyl, phenyldiisopropylsilyl, diphenylisopropylsilyl, diphenyl- butylsilyl, diphenylisobutylsilyl, diphenyl t-butylsilyl. Additionally, the arylsilyl group may be optionally substituted.

The term "aza" in azadibenzofuran, azadibenzothiophene, etc. means that one or more of C—H groups in the respective aromatic fragment are replaced by a nitrogen atom. For example, azatriphenylene encompasses dibenzo[f,h]quinoxaline, dibenzo[f,h]quinoline and other analogs with two or more nitrogens in the ring system. One of ordinary skill in the art can readily envision other nitrogen analogs of the aza-derivatives described above, and all such analogs are intended to be encompassed by the terms as set forth herein.

In the present disclosure, unless otherwise defined, when any term of the group consisting of substituted alkyl, substituted cycloalkyl, substituted heteroalkyl, substituted heterocyclic group, substituted arylalkyl, substituted alkoxy, substituted aryloxy, substituted alkenyl, substituted alkynyl, substituted aryl, substituted heteroaryl, substituted alkylsilyl, substituted arylsilyl, substituted amino, substituted acyl, substituted carbonyl, a substituted carboxylic acid group, a substituted ester group, substituted sulfinyl, substituted sulfonyl, and substituted phosphino is used, it means that any group of alkyl, cycloalkyl, heteroalkyl, heterocyclic group, arylalkyl, alkoxy, aryloxy, alkenyl, alkynyl, aryl, heteroaryl, alkylsilyl, arylsilyl, amino, acyl, carbonyl, a carboxylic acid group, an ester group, sulfinyl, sulfonyl, and phosphino may be substituted with one or more moieties selected from the group consisting of deuterium, halogen, unsubstituted alkyl having 1 to 20 carbon atoms, unsubstituted cycloalkyl having 3 to 20 ring carbon atoms, unsubstituted heteroalkyl having 1 to 20 carbon atoms, an unsubstituted heterocyclic group having 3 to 20 ring atoms, unsubstituted arylalkyl having 7 to 30 carbon atoms, unsubstituted alkoxy having 1 to 20 carbon atoms, unsubstituted aryloxy having 6 to 30 carbon atoms, unsubstituted alkenyl having 2 to 20 carbon atoms, unsubstituted alkynyl having 2 to 20 carbon atoms, unsubstituted aryl having 6 to 30 carbon atoms, unsubstituted heteroaryl having 3 to 30 carbon atoms, unsubstituted alkylsilyl having 3 to 20 carbon atoms, unsubstituted arylsilyl group having 6 to 20 carbon atoms, unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or an attached fragment are considered to be equivalent.

In the compounds mentioned in the present disclosure, hydrogen atoms may be partially or fully replaced by deuterium. Other atoms such as carbon and nitrogen may also be replaced by their other stable isotopes. The replacement by other stable isotopes in the compounds may be preferred due to its enhancements of device efficiency and stability.

In the compounds mentioned in the present disclosure, multiple substitution refers to a range that includes a di-substitution, up to the maximum available substitution. When substitution in the compounds mentioned in the present disclosure represents multiple substitution (including di-, tri-, and tetra-substitutions etc.), that means the substituent may exist at a plurality of available substitution positions on its linking structure, the substituents present at a plurality of available substitution positions may have the same structure or different structures.

In the compounds mentioned in the present disclosure, adjacent substituents in the compounds cannot be joined to form a ring unless otherwise explicitly defined, for example, adjacent substituents can be optionally joined to form a ring. In the compounds mentioned in the present disclosure, the expression that adjacent substituents can be optionally joined to form a ring includes a case where adjacent substituents may be joined to form a ring and a case where adjacent substituents are not joined to form a ring. When adjacent substituents can be optionally joined to form a ring, the ring formed may be monocyclic or polycyclic, as well as alicyclic, heteroalicyclic, aromatic, or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

In the present disclosure, the number of ring atoms represents the number of atoms constituting a ring itself of a compound having a structure in which atoms are bonded in the form of a ring (for example, a monocyclic compound, a fused ring compound, a crosslinked compound, a carbocyclic compound, and a heterocyclic compound). When the ring is substituted by a substituent, the atoms contained in the substituent are not included in the number of ring atoms. The "number of ring atoms" recorded herein has the same meaning unless otherwise stated. For example, the number of ring atoms of

is 4, where • is the position where ring A is connected. The number of ring atoms of

is 5. The number of ring atoms of

is 6. The number of ring atoms of

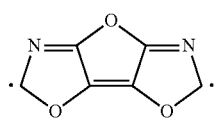

is 11.

The expression that adjacent substituents can be optionally joined to form a ring is also intended to mean that two substituents bonded to the same carbon atom are joined to each other via a chemical bond to form a ring, which can be exemplified by the following formula:

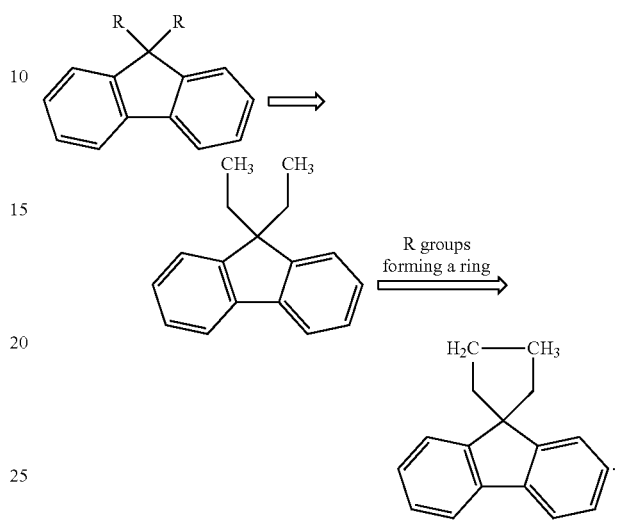

The expression that adjacent substituents can be optionally joined to form a ring is also intended to mean that two substituents bonded to carbon atoms which are directly bonded to each other are joined to each other via a chemical bond to form a ring, which can be exemplified by the following formula:

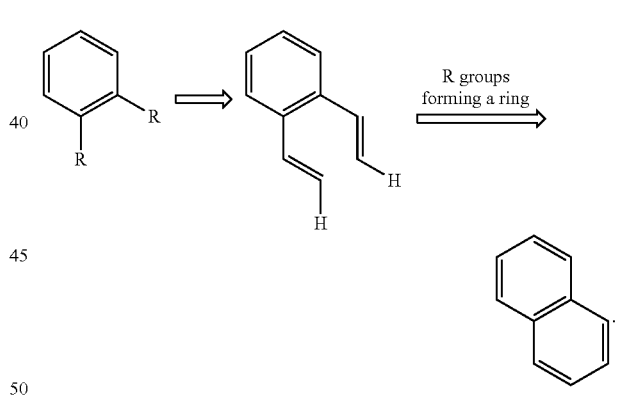

Furthermore, the expression that adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

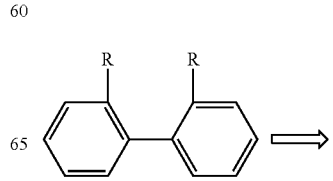

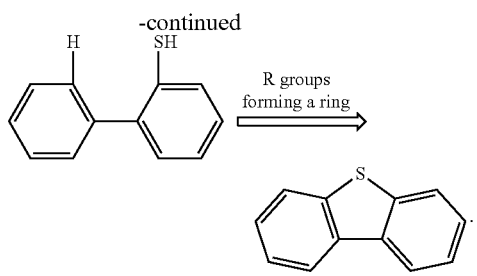

According to an embodiment of the present disclosure, disclosed is a compound which has a structure represented by Formula 1:

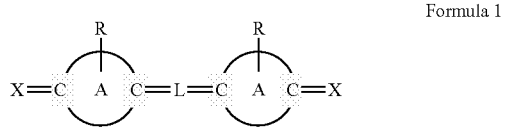

Formula 1 wherein
L is, at each occurrence identically or differently, selected from

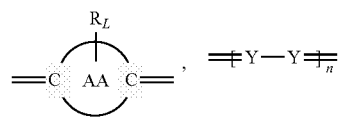

or any combination thereof;
ring AA is a conjugated structure having 4 to 30 ring atoms and at least one intra-ring double bond;
n is, at each occurrence identically or differently, selected from an integer from 0 to 10;
Y is, at each occurrence identically or differently, selected from the group consisting of $CR_L$ and N;
ring A is, at each occurrence identically or differently, a 5-membered heterocyclic ring, and the 5-membered heterocyclic ring comprises an intra-ring double bond, at least one N atom, and at least one W; W is, at each occurrence identically or differently, selected from the group consisting of O, S, Se, and $NR_N$;
X is, at each occurrence identically or differently, selected from the group consisting of Se, NR', and CR"R'";
R and $R_L$ represent, at each occurrence identically or differently, mono-substitution, multiple substitutions or non-substitution;
R, R', R", R''', $R_L$, and $R_N$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;
when L is selected from

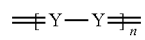

and n=0, at least one of substituents R and $R_N$ is a group having at least one electron-withdrawing group;
when X is selected from NR' or CR"R''', at least one of R', R", and R''' is a group having at least one electron-withdrawing group;
adjacent substituents R", R''' can be optionally joined to form a ring; and
adjacent substituents R, $R_L$ can be optionally joined to form a ring; when adjacent substituents $R_L$ are joined to form a ring, the resulting ring has at least 4 ring atoms; and when adjacent substituents R are joined to form a ring, the resulting ring has at least 6 ring atoms.

Herein, when n=0, which means that L does not exist, that is, the two rings in Formula 1 are directly connected by a double bond, a structure of Formula 1-1 is formed:

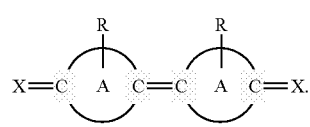

Formula 1-1

In this embodiment, "when L is selected from

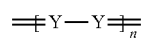

and n=0, at least one of substituents R and $R_N$ is a group having at least one electron-withdrawing group" is intended to mean that when Formula 1 has the structure of Formula 1-1, at least one of the substituent in the substituent group consisting of R and $R_N$ is a group having at least one electron-withdrawing group when R represents, at each occurrence identically or differently, mono-substitution, multiple substitutions or non-substitution. Obviously, when a certain one of R and $R_N$ does not exist, the preceding substituent group still needs to satisfy the condition that at least one substituent is a group having at least one electron-withdrawing group.

In this embodiment, "L is, at each occurrence identically or differently, selected from

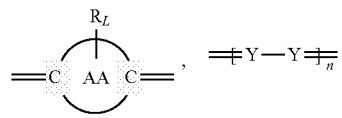

or any combination thereof," is intended to mean that L is, at each occurrence identically or differently, selected from

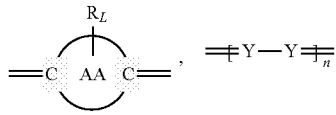

a combination of

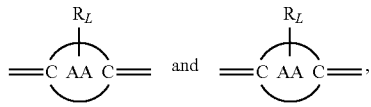

a combination of

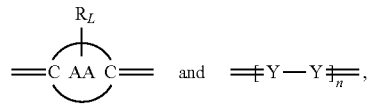

or a combination of

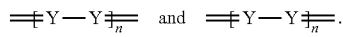

Herein, "adjacent substituents R", R'" can be optionally joined to form a ring" is intended to mean that the substituents R" and R'" can be joined to form a ring when X is selected from CR"R'". When the substituents R" and R'" are joined to form a ring, the resulting ring can have 4 ring atoms or 5 ring atoms. Obviously, it is possible that none of substituents R" and R'" are joined to form a ring.

Herein, "adjacent substituents R, $R_L$ can be optionally joined to form a ring" is intended to mean that for groups of adjacent substituents, for example, substituents R, substituents $R_L$, and substituents R and $R_L$, any one or more of these substituent groups can be joined to form a ring. When adjacent substituents $R_L$ are joined to form a ring, the resulting ring has at least 4 ring atoms; and when adjacent substituents R are joined to form a ring, the resulting ring has at least 6 ring atoms. Adjacent substituents R and $R_L$ can be randomly joined to form a ring. Obviously, it is possible that none of these substituents are joined to form a ring.

According to an embodiment of the present disclosure, wherein at least one of substituents R, $R_L$, and $R_N$ is a group having at least one electron-withdrawing group; preferably, at least one of R and $R_L$ is a group having at least one electron-withdrawing group.

In this embodiment, "wherein at least one of substituents R, $R_L$, and $R_N$ is a group having at least one electron-withdrawing group" means that when W is selected from $NR_N$, at least one of the substituents R, $R_L$, and $R_N$ is a group having at least one electron-withdrawing group; and when W is selected from O, S, and Se, at least one of the substituents R and $R_L$ is a group having at least one electron-withdrawing group.

In this embodiment, "wherein substituents R, $R_L$, and $R_N$ are each a group having at least one electron-withdrawing group" is intended to mean that when R and $R_L$ represent, at each occurrence identically or differently, mono-substitution, multiple substitutions or non-substitution, at least one substituent in the substituent group consisting of R, $R_L$, and $R_N$ is a group having at least one electron-withdrawing group. Obviously, when a certain one of R, $R_L$, and $R_N$ does not exist, the preceding substituent group still needs to satisfy the condition that at least one substituent is a group having at least one electron-withdrawing group. For example, when W is selected from O, S, and Se, at least one of substituents R and $R_L$ is a group having at least one electron-withdrawing group.

According to an embodiment of the present disclosure, wherein substituents R, R', R", R'", $R_L$, and $R_N$ are each a group having at least one electron-withdrawing group.

According to an embodiment of the present disclosure, wherein ring A contains CR, and R is a group having at least one electron-withdrawing group.

According to an embodiment of the present disclosure, wherein

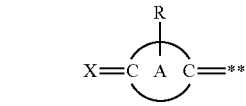

connected to both sides of L in Formula 1 is, at each occurrence identically or differently, selected from any one of the structures represented by Formula 2 to Formula 5:

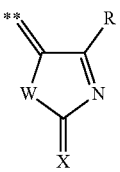

Formula 2

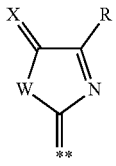

Formula 3

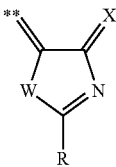

Formula 4

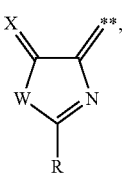

Formula 5 wherein in Formula 2 to Formula 5,
X is, at each occurrence identically or differently, selected from the group consisting of Se, NR', and CR"R'";
W is, at each occurrence identically or differently, selected from the group consisting of O, S, Se, and $NR_N$;
R, R', R", R'", and $R_N$ are, at each occurrence identically or differently, selected from the group consisting of:

hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

when X is selected from NR' or CR"R''', at least one of R', R", and R''' is a group having at least one electron-withdrawing group;

adjacent substituents R", R''' can be optionally joined to form a ring;

adjacent substituents R can be optionally joined to form a ring having at least 6 ring atoms; and

** represents a position where Formula 2 to Formula 5 are connected to L in Formula 1.

According to an embodiment of the present disclosure, wherein substituents R, R', R", R''', and $R_N$ are each a group having at least one electron-withdrawing group.

According to an embodiment of the present disclosure, wherein L is, at each occurrence identically or differently, selected from structures represented by Formula 6 and Formula 6A and combinations thereof:

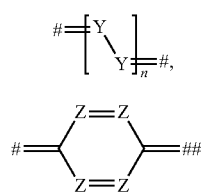

Formula 6

Formula 6A wherein in Formula 6 and Formula 6A, n is, at each occurrence identically or differently, selected from an integer from 0 to 10;

Y and Z are, at each occurrence identically or differently, selected from $CR_L$ or N;

$R_L$ is, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

adjacent substituents $R_A$ and $R_B$ can be optionally joined to form a ring;

adjacent substituents $R_L$ can be optionally joined to form a ring having 4 or more ring atoms; and # and ## represent positions where Formula 6 and Formula 6A are connected to ring A or L in Formula 1.

According to an embodiment of the present disclosure, wherein substituents $R_A$, $R_B$, and $R_L$ are each a group having at least one electron-withdrawing group.

According to an embodiment of the present disclosure, wherein n is, at each occurrence identically or differently, selected from 1, 2, 3, 4, 5, 6, 7, 8, 9, and 10; and m is, at each occurrence identically or differently, selected from 1, 2, 3, and 4.

According to an embodiment of the present disclosure, wherein L is

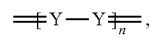

n is 0, and the compound has any one of the structures represented by Formula I to Formula XVI:

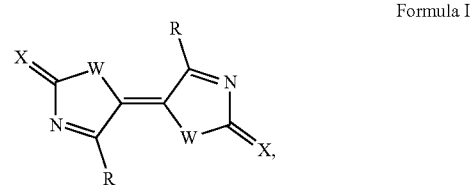

Formula I

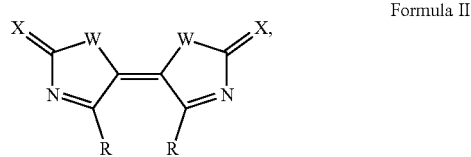

Formula II

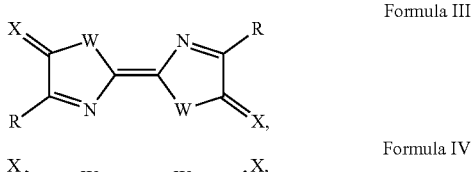

Formula III

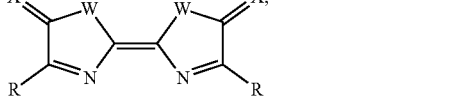

Formula IV

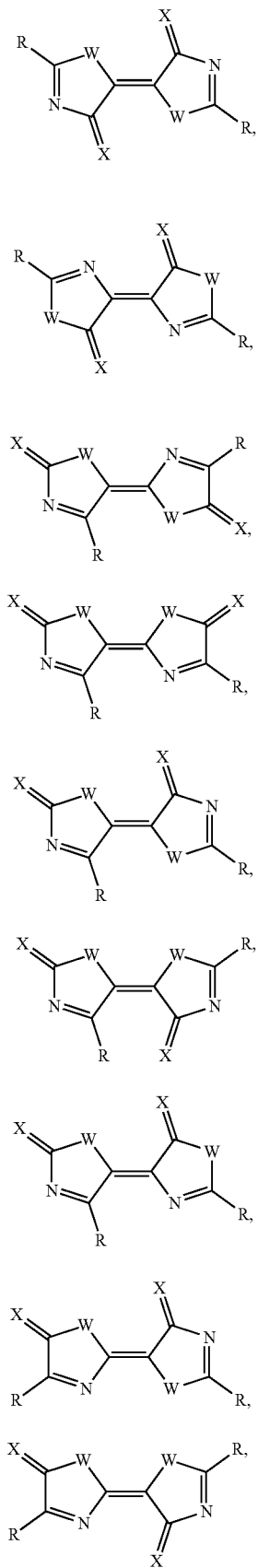

Formula V

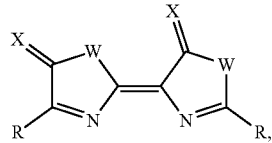

Formula XIV

Formula VI

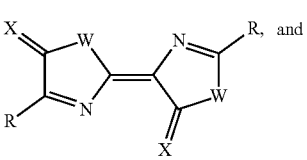

Formula XV

Formula VII

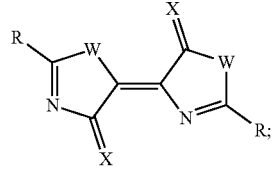

Formula XVI

Formula VIII

Formula IX

Formula X

Formula XI

Formula XII

Formula XIII wherein in Formula I to Formula XVI,

X is, at each occurrence identically or differently, selected from the group consisting of Se, NR', and CR"R'";

W is, at each occurrence identically or differently, selected from the group consisting of O, S, Se, and $NR_N$;

R, R', R", R'", and $R_N$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

when X is selected from NR' or CR"R'", at least one of R', R", and R'" is a group having at least one electron-withdrawing group;

at least one of substituents R and $R_N$ is a group having at least one electron-withdrawing group;

adjacent substituents R", R'" can be optionally joined to form a ring; and adjacent substituents R can be optionally joined to form a ring having at least 6 ring atoms.

According to an embodiment of the present disclosure, wherein the compound has any one of the following structures:

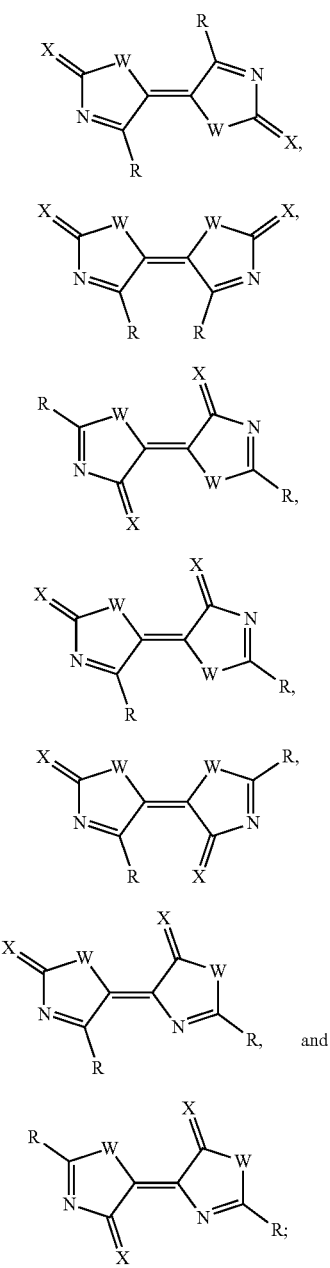

Formula I

Formula II

Formula V

Formula IX

Formula X

Formula XI and

Formula XVI wherein

X is, at each occurrence identically or differently, selected from the group consisting of Se, NR', and CR"R'";

W is, at each occurrence identically or differently, selected from the group consisting of O, S, Se, and $NR_N$;

R, R', R", R''', and $R_N$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

when X is selected from NR' or CR"R'", at least one of R', R", and R'" is a group having at least one electron-withdrawing group;

at least one of substituents R and $R_N$ is a group having at least one electron-withdrawing group;

adjacent substituents R", R'" can be optionally joined to form a ring; and adjacent substituents R can be optionally joined to form a ring having at least 6 ring atoms.

According to an embodiment of the present disclosure, wherein substituents R, R', R", R'", and $R_N$ are each a group having at least one electron-withdrawing group.

According to an embodiment of the present disclosure, the compound has any one of the structures represented by Formula LI and Formula LIA:

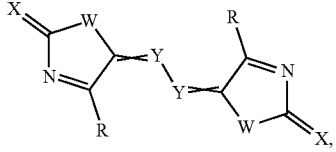

Formula LI

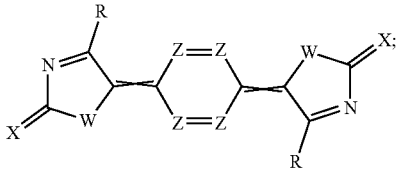

Formula LIA wherein in Formula LI and Formula LIA,

Y and Z are, at each occurrence identically or differently, selected from the group consisting of $CR_L$ and N;

X is, at each occurrence identically or differently, selected from the group consisting of Se, NR', and CR"R'";

W is, at each occurrence identically or differently, selected from the group consisting of O, S, Se, and $NR_N$;

R, R', R", R'", $R_L$, and $R_N$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

when X is selected from NR' or CR"R'", at least one of R', R", and R'" is a group having at least one electron-withdrawing group;

adjacent substituents R", R'" can be optionally joined to form a ring; and adjacent substituents R, $R_L$ can be optionally joined to form a ring; when adjacent substituents $R_L$ are joined to form a ring, the resulting ring has at least 4 ring atoms; and when adjacent substituents R are joined to form a ring, the resulting ring has at least 6 ring atoms.

Preferably, at least one of substituents R, $R_L$, and $R_N$ is a group having at least one electron-withdrawing group.

Herein, ⊰⊱ in a structure formula indicates that the structure has a cis-configuration and a trans-configuration. Taking

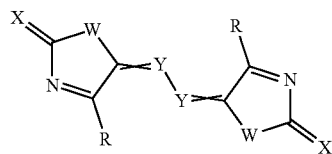

Formula LI as an example, when two R are identical, two Y are identical, and two X are identical in Formula LI, the following structures are included:

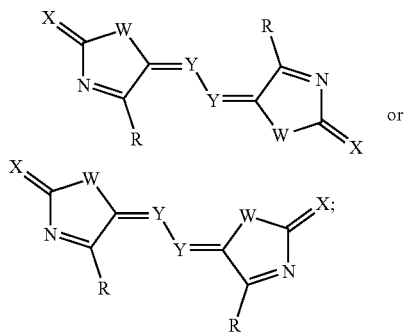

and when at least one pair of two R (referred as $R^1$ and $R^2$; $R^1$ and $R^2$ may be identical or different), and/or two Y (referred as $Y_1$ and $Y_2$; $Y_1$ and $Y_2$ may be identical or different), and/or two X (referred as $X_1$ and $X_2$; $X_1$ and $X_2$ may be identical or different) are different in Formula LI, the following structures are included:

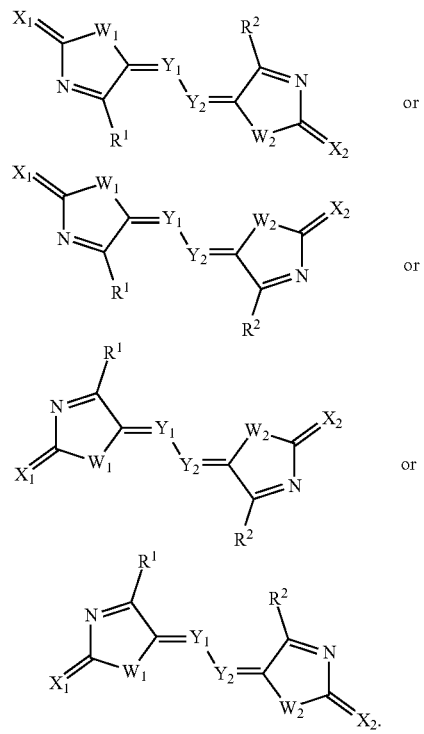

According to an embodiment of the present disclosure, wherein substituents $R_A$, $R_B$, R, R', R", R'", $R_L$, and $R_N$ are each a group having at least one electron-withdrawing group.

According to an embodiment of the present disclosure, wherein substituents R, $R_L$ are not joined to form a ring. For example, substituents R and R, substituents $R_L$ and $R_L$, and substituents R and $R_L$ are not joined to form a ring.

According to an embodiment of the present disclosure, wherein the compound has the structure represented by Formula II-I:

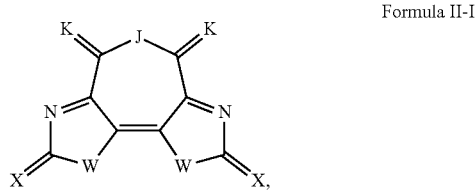

Formula II-I wherein
K is, at each occurrence identically or differently, selected from the group consisting of O, S, Se, and $CR_AR_B$;
X is, at each occurrence identically or differently, selected from the group consisting of Se, NR', and CR"R'";
W is, at each occurrence identically or differently, selected from the group consisting of O, S, Se, and $NR_N$;
J is, at each occurrence identically or differently, selected from the group consisting of O, S, Se, and $NR_{NJ}$;
preferably, J is, at each occurrence identically or differently, selected from $NR_{NJ}$;
$R_A$, $R_B$, R', R", R'", $R_N$ and $R_{NJ}$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

adjacent substituents $R_A$ and $R_B$ can be optionally joined to form a ring;

in Formula II-I, at least one of substituents $R_A$, $R_B$, $R_N$, and $R_{NJ}$ is a group having at least one electron-withdrawing group, and/or at least one of K is O;

when X is selected from NR' or CR"R'", at least one of R', R", and R'" is a group having at least one electron-withdrawing group; and adjacent substituents R", R'" can be optionally joined to form a ring.

According to an embodiment of the present disclosure, wherein in Formula II-I, at least one of substituents $R_A$, $R_B$, $R_N$, and $R_{NJ}$ is a group having at least one electron-withdrawing group, and/or at least one of K is O.

According to an embodiment of the present disclosure, wherein Y is, at each occurrence identically or differently, selected from $CR_L$ or N.

According to an embodiment of the present disclosure, wherein Y is, at each occurrence identically or differently, selected from $CR_L$.

According to an embodiment of the present disclosure, wherein X is, at each occurrence identically or differently, selected from CR"R'".

According to an embodiment of the present disclosure, wherein W is, at each occurrence identically or differently, selected from O, S or Se.

According to an embodiment of the present disclosure, wherein W is, at each occurrence identically or differently, selected from O or S.

According to an embodiment of the present disclosure, wherein W is O.

According to an embodiment of the present disclosure, wherein W is, at each occurrence identically or differently, selected from $NR_N$, and $R_N$ is, at each occurrence identically or differently, selected from the group consisting of: substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof.

According to an embodiment of the present disclosure, wherein $R_N$ is, at each occurrence identically or differently, selected from the group consisting of: substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, and combinations thereof.

According to an embodiment of the present disclosure, wherein at least one of R is a group having at least one electron-withdrawing group.

According to an embodiment of the present disclosure, wherein each of R', R", R'", $R_L$, $R_N$, and $R_{NJ}$ is a group having at least one electron-withdrawing group.

According to an embodiment of the present disclosure, wherein at least one of R represents mono-substitution or multiple substitutions, and at least one of R is a group having an electron-withdrawing group.

According to an embodiment of the present disclosure, wherein at least one of R is selected from substituted or unsubstituted aryl having 6 to 30 carbon atoms, substituted or unsubstituted heteroaryl having 3 to 30 carbon atoms, or combinations thereof.

According to an embodiment of the present disclosure, wherein at least one of R is substituted aryl having 6 to 30 carbon atoms having at least one electron-withdrawing group, substituted heteroaryl having 3 to 30 carbon atoms having at least one electron-withdrawing group or combinations thereof.

According to an embodiment of the present disclosure, wherein R is, at each occurrence identically or differently, a group having at least one electron-withdrawing group.

According to an embodiment of the present disclosure, wherein R is, at each occurrence identically or differently, selected from substituted or unsubstituted aryl having 6 to 30 carbon atoms, substituted or unsubstituted heteroaryl having 3 to 30 carbon atoms, or combinations thereof; and preferably, R is, at each occurrence, aryl which has 6 to 30 carbon atoms and is substituted with at least one electron-withdrawing group, heteroaryl which has 3 to 30 carbon atoms and is substituted with at least one electron-withdrawing group, or combinations thereof.

According to an embodiment of the present disclosure, wherein the Hammett constant of the electron-withdrawing group is greater than or equal to 0.05, preferably, is greater than or equal to 0.3, and more preferably, is greater than or equal to 0.5.

In the present disclosure, the Hammett substituent constant value of the electron-withdrawing group is greater than or equal to 0.05, for example, greater than or equal to 0.1 or greater than or equal to 0.2, preferably, is greater than or equal to 0.3, and more preferably, is greater than or equal to 0.5. The electron-withdrawing ability is strong, which can significantly reduce the LUMO energy level of the compound and achieve the effect of improving the charge mobility.

It is to be noted that the Hammett substituent constant value includes para and/or meta Hammett substituent constants. As long as both the para constant and meta constant are greater than 0 and one of the para constant and meta constant is greater than or equal to 0.05, the substituent can be used as the group selected in the present disclosure.

According to an embodiment of the present disclosure, wherein the electron-withdrawing group is selected from the group consisting of: halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, an aza-aromatic ring group, or any one of the following groups substituted by one or more of halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, and an aza-aromatic ring group: alkyl having 1 to 20 carbon atoms, cycloalkyl having 3 to 20 ring carbon atoms, heteroalkyl having 1 to 20 carbon atoms, a heterocyclic group having 3 to 20 ring atoms, aralkyl having 7 to 30 carbon atoms, alkoxy having 1 to 20 carbon atoms, aryloxy having 6 to 30 carbon atoms, alkenyl having 2 to 20 carbon atoms, alkynyl having 2 to 20 carbon atoms, aryl having 6 to 30 carbon atoms, heteroaryl having 3 to 30 carbon atoms, alkylsilyl having 3 to 20 carbon atoms, arylsilyl having 6 to 20 carbon atoms, and combinations thereof.

According to an embodiment of the present disclosure, wherein the electron-withdrawing group is selected from the group consisting of: halogen, a nitroso group, a nitro group, an acyl group, a carbonyl group, a carboxylic acid group, an ester group, $SF_5$, a boranyl group, a sulfinyl group, a sulfonyl group, a phosphoroso group, an aza-aromatic ring group, or any one of the following groups substituted by one or more of halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, and an aza-aromatic ring group: alkyl having 1 to 20 carbon atoms, cycloalkyl having 3 to 20 ring carbon atoms, heteroalkyl having 1 to 20 carbon atoms, aralkyl having 7 to 30 carbon atoms, alkoxy having 1 to 20 carbon atoms, aryloxy having 6 to 30 carbon atoms, alkenyl having 2 to 20 carbon atoms, alkynyl having 2 to 20 carbon atoms, aryl having 6 to 30 carbon atoms, heteroaryl having 3 to 30 carbon atoms, alkylsilyl having 3 to 20 carbon atoms, arylsilyl having 6 to 20 carbon atoms, and combinations thereof.

According to an embodiment of the present disclosure, wherein the electron-withdrawing group is selected from the group consisting of: fluorine, an acyl group, a carbonyl group, an ester group, $SF_5$, a boranyl group, an aza-aromatic ring group, and any one of the following groups substituted by one or more of fluorine, a cyano group, an isocyano group, SCN, OCN, $SF_5$, $CF_3$, $OCF_3$, $SCF_3$, and an aza-aromatic ring group: alkyl having 1 to 20 carbon atoms, cycloalkyl having 3 to 20 ring carbon atoms, heteroalkyl having 1 to 20 carbon atoms, aralkyl having 7 to 30 carbon atoms, alkoxy having 1 to 20 carbon atoms, aryloxy having 6 to 30 carbon atoms, alkenyl having 2 to 20 carbon atoms, alkynyl having 2 to 20 carbon atoms, aryl having 6 to 30 carbon atoms, heteroaryl having 3 to 30 carbon atoms, alkylsilyl having 3 to 20 carbon atoms, arylsilyl having 6 to 20 carbon atoms, and combinations thereof.

According to an embodiment of the present disclosure, wherein the electron-withdrawing group is selected from the group consisting of: fluorine, an acyl group, a carbonyl group, an ester group, $SF_5$, a boranyl group, an aza-aromatic ring group, and any one of the following groups substituted by one or more of fluorine, a cyano group, an isocyano group, SCN, OCN, $SF_5$, $CF_3$, $OCF_3$, $SCF_3$, and an aza-aromatic ring group: aryl having 6 to 30 carbon atoms, heteroaryl having 3 to 30 carbon atoms, and combinations thereof.

According to an embodiment of the present disclosure, wherein the electron-withdrawing group is selected from the group consisting of: fluorine, $SF_5$, a boranyl group, a pyridyl group, a pyrimidinyl group, an imidazolyl group, a thiazolyl group, an oxazolyl group, a triazinyl group, and any one of the following groups substituted by one or more of fluorine, a cyano group, an isocyano group, SCN, OCN, $SF_5$, $CF_3$, $OCF_3$, $SCF_3$, a pyridyl group, a pyrimidinyl group, an imidazolyl group, a thiazolyl group, an oxazolyl group, and a triazinyl group: a phenyl group, a biphenyl group, a naphthyl group, a phenanthryl group, an anthryl group, a pyridyl group, a pyrimidinyl group, and combinations thereof.

According to an embodiment of the present disclosure, wherein the electron-withdrawing group is selected from the group consisting of: any one of the following groups substituted by one or more of fluorine, $SF_5$, $CF_3$, $OCF_3$, and $SCF_3$: a phenyl group, a biphenyl group, a naphthyl group, a phenanthryl group, an anthryl group, a pyridyl group, a pyrimidinyl group, and combinations thereof.

According to an embodiment of the present disclosure, wherein the electron-withdrawing group is selected from the group consisting of: any one of the following groups substituted by one or more of fluorine, $SF_5$, $CF_3$, $OCF_3$, and $SCF_3$: aryl having 6 to 30 carbon atoms, heteroaryl having 3 to 30 carbon atoms, and combinations thereof.

According to an embodiment of the present disclosure, wherein the electron-withdrawing group is selected from a group consisting of: F, $CF_3$, $OCF_3$, $SF_5$, $SO_2CF_3$, a cyano group, an isocyano group, SCN, OCN, a pyrimidinyl group, a triazinyl group, and combinations thereof.

According to an embodiment of the present disclosure, wherein X is, at each occurrence identically or differently, selected from the group consisting of the following structures:

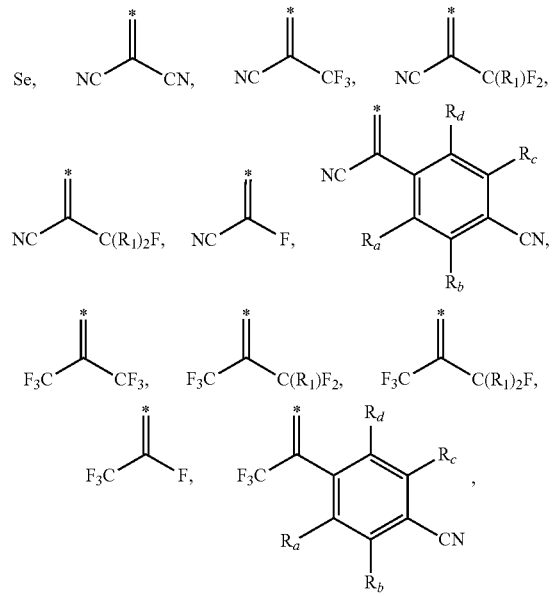

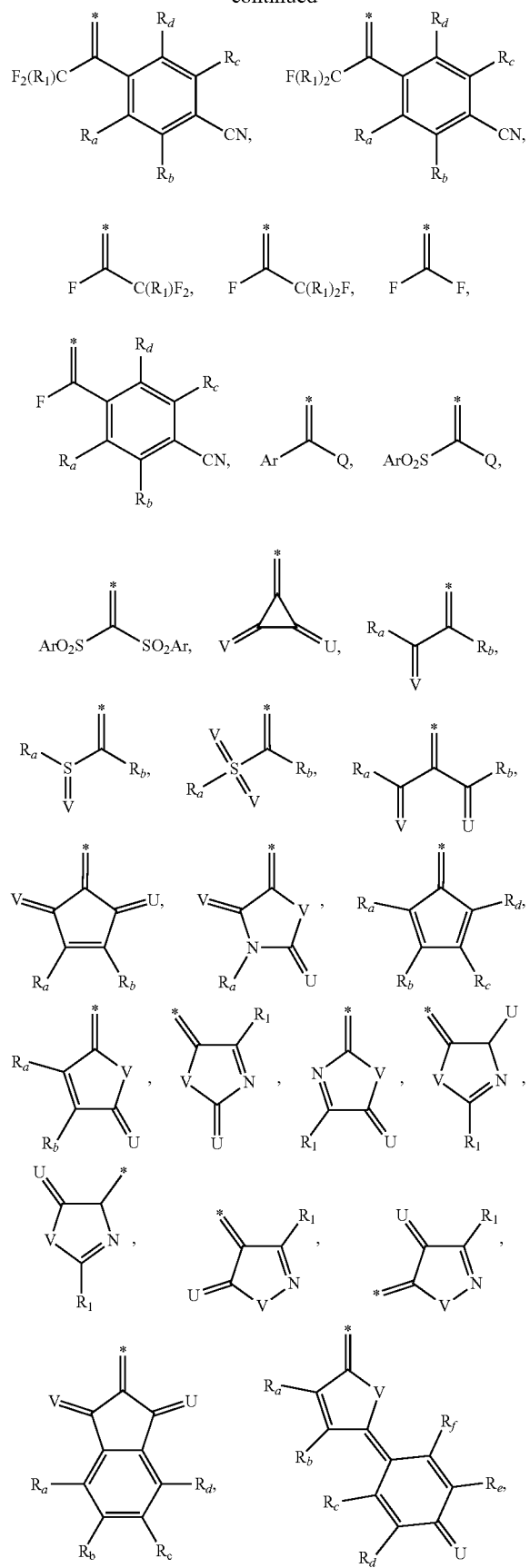
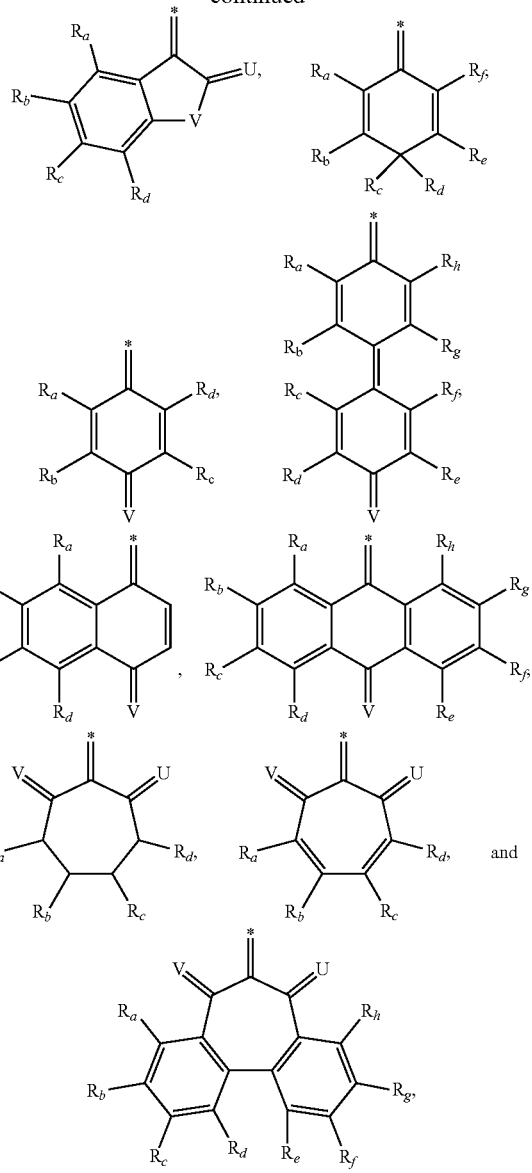

wherein V, U, and T are, at each occurrence identically or differently, selected from the group consisting of $CR_vR_h$, $NR_v$, O, S, and Se;

wherein Ar is, at each occurrence identically or differently, selected from substituted or unsubstituted aryl having 6 to 30 carbon atoms or substituted or unsubstituted heteroaryl having 3 to 30 carbon atoms;

wherein $R_1$, Q, $R_a$, $R_b$, $R_c$, $R_d$, $R_e$, $R_f$, $R_g$, $R_h$, $R_v$, and $R_u$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

preferably, $R_1$ is, at each occurrence identically or differently, selected from the group consisting of: F, $CF_3$, $OCF_3$, $SF_5$, $SO_2CF_3$, a cyano group, an isocyano group, SCN, OCN, pentafluorophenyl, 4-cyanotetrafluorophenyl, tetrafluoropyridyl, a pyrimidinyl group, a triazinyl group, and combinations thereof;

wherein Q is a group having at least one electron-withdrawing group, and for any one of the preceding structures, when one or more of $R_a$, $R_b$, $R_c$, $R_d$, $R_e$, $R_f$, $R_g$, $R_h$, $R_v$, and $R_u$ occur, at least one of $R_a$, $R_b$, $R_c$, $R_d$, $R_e$, $R_f$, $R_g$, $R_h$, $R_v$, and $R_u$ is a group having at least one electron-withdrawing group; preferably, the group having at least one electron-withdrawing group is selected from the group consisting of: F, $CF_3$, $OCF_3$, $SF_5$, $SO_2CF_3$, a cyano group, an isocyano group, SCN, OCN, pentafluorophenyl, 4-cyanotetrafluorophenyl, tetrafluoropyridyl, a pyrimidinyl group, a triazinyl group, and combinations thereof;

adjacent substituents $R_1$, $R_a$ $R_b$, $R_c$, $R_d$, $R_e$, $R_f$, $R_g$, $R_h$, $R_v$, and $R_u$ can be optionally joined to form a ring; and

* represents a position where X having the preceding structures is connected to ring A in Formula 1.

According to an embodiment of the present disclosure, wherein $R_1$ is, at each occurrence identically or differently, selected from the group consisting of: F, $CF_3$, $OCF_3$, $SF_5$, $SO_2CF_3$, a cyano group, an isocyano group, SCN, OCN, pentafluorophenyl, 4-cyanotetrafluorophenyl, tetrafluoropyridyl, a pyrimidinyl group, a triazinyl group, and combinations thereof.

According to an embodiment of the present disclosure, wherein X is, at each occurrence identically or differently, selected from the group consisting of the following structures:

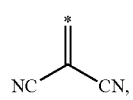

Se,

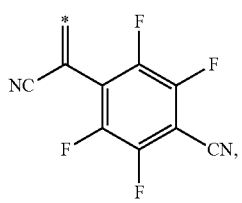

A1

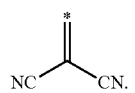

A2

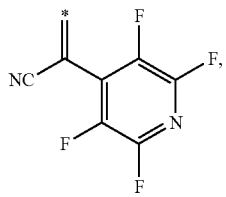

A3

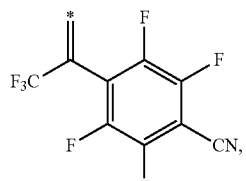

A4

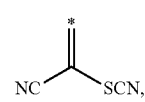

A5

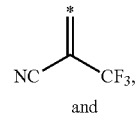

A6 and

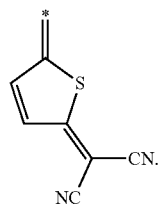

A7

According to an embodiment of the present disclosure, wherein X is selected from

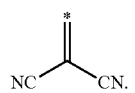

A1

According to an embodiment of the present disclosure, wherein R, $R_L$, $R_N$, and $R_{NJ}$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof.

According to an embodiment of the present disclosure, wherein R, $R_L$, $R_N$, and $R_{NJ}$ are, at each occurrence identically or differently, selected from the group consisting of: hydrogen, deuterium, a methyl group, an isopropyl group, $NO_2$, $SO_2CH_3$, $SCF_3$, $C_2F_5$, $OC_2F_5$, diphenylmethylsilyl, a phenyl group, methoxyphenyl, p-methylphenyl, 2,6-diisopropylphenyl, a biphenylyl group, polyfluorophenyl, difluopyridyl, nitrophenyl, dimethylthiazolyl, CN, a vinyl group substituted by one or more of CN or $CF_3$, an acetenyl group substituted by one of CN or $CF_3$, dimethylphosphoryl, diphenylphosphoryl, F, $CF_3$, $OCF_3$, $SF_5$, $SO_2CF_3$, a cyano group, an isocyano group, SCN, OCN, trifluoromethylphenyl, trifluoromethoxyphenyl, bis(trifluoromethyl)phenyl, bis(trifluoromethoxy)phenyl, 4-cyanotetrafluorophenyl, a phenyl or biphenylyl group substituted by one or more of F, CN or $CF_3$, tetrafluoropyridyl, a pyrimidinyl group, a triazinyl group, a pyridyl group, diphenylboryl, phenoxaborin, and combinations thereof.

According to an embodiment of the present disclosure, wherein R, $R_L$, $R_N$, and $R_{NJ}$ are, at each occurrence identically or differently, selected from the group consisting of the following structures:

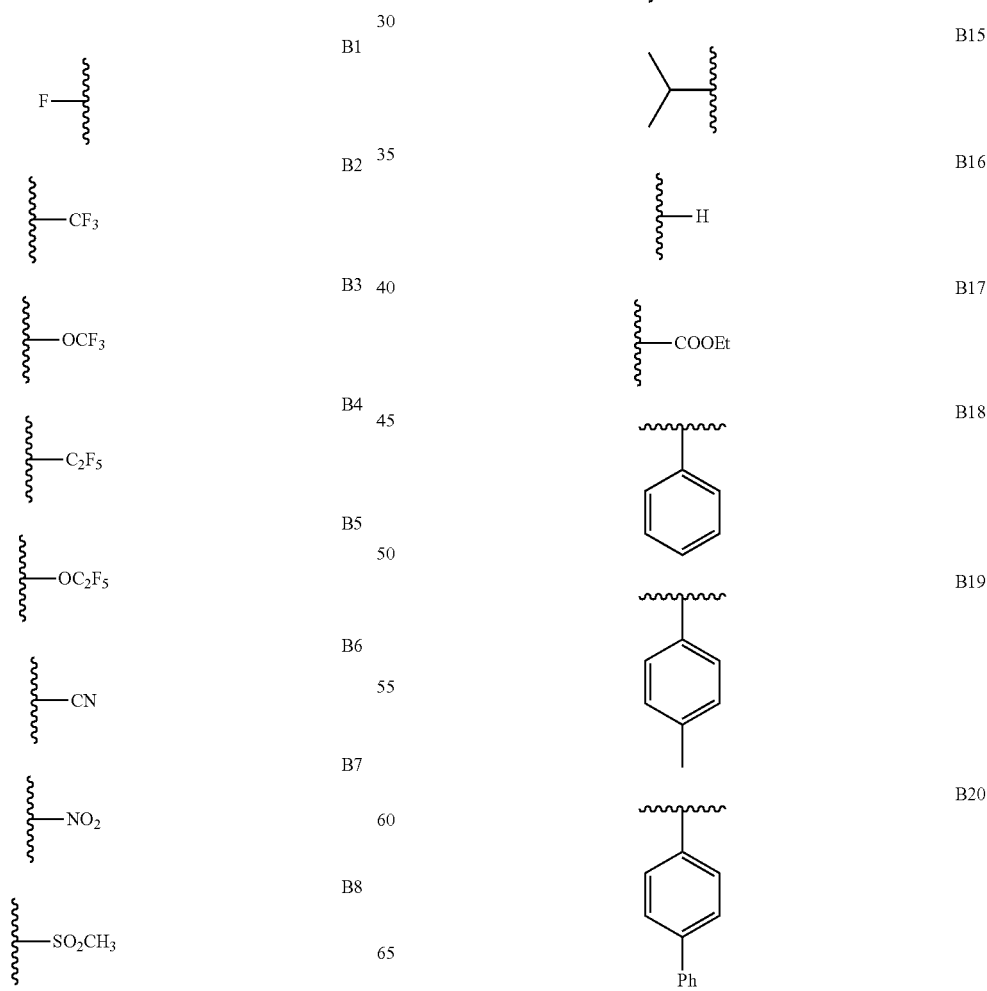

B21 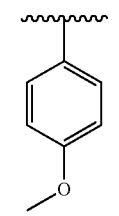
B22 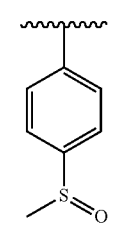
B23 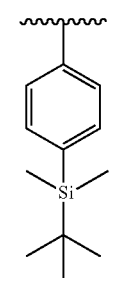
B24 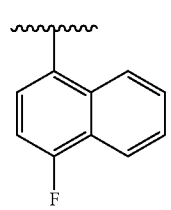
B25 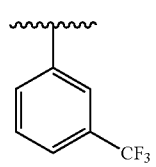
B26 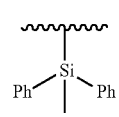
B27 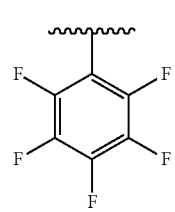
B28 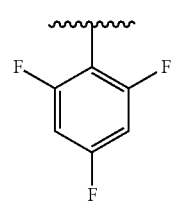
B29 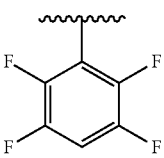
B30 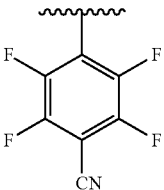
B31 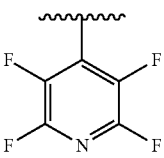
B32 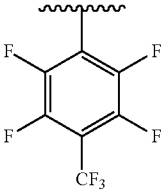
B33 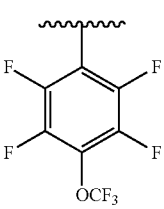
B34 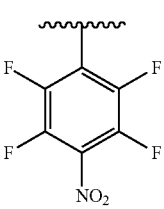
B35 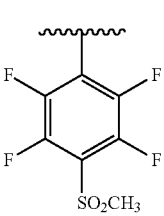
B36 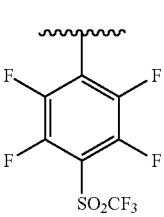

-continued
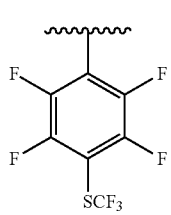 B37
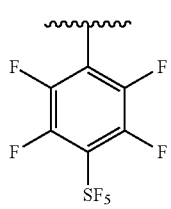 B38
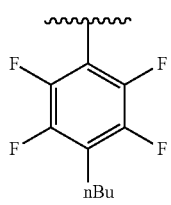 B39
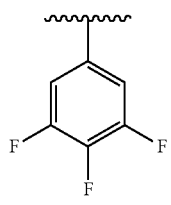 B40
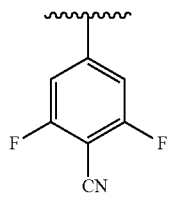 B41
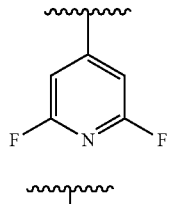 B42
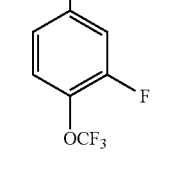 B43
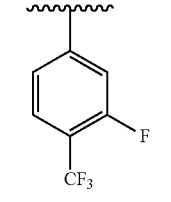 B44
-continued
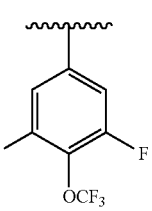 B45
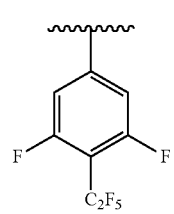 B46
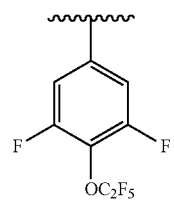 B47
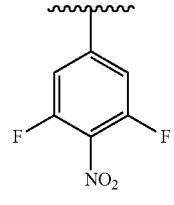 B48
 B49
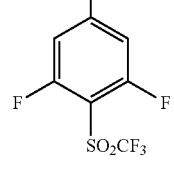 B50
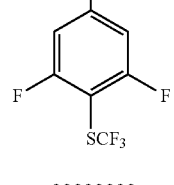 B51
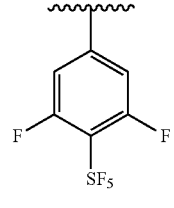 B52

-continued
B53 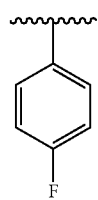
B54 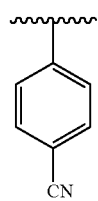
B55 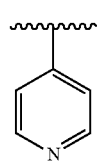
B56 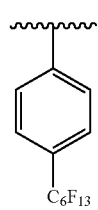
B57 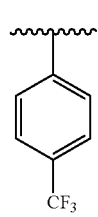
B58 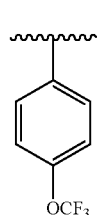
B59 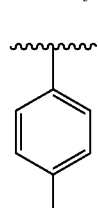
B60 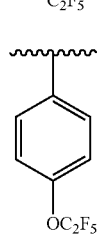
-continued
B61 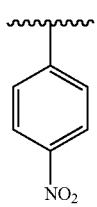
B62 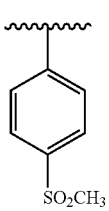
B63 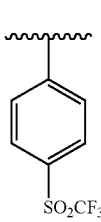
B64 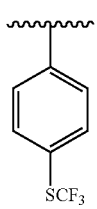
B65 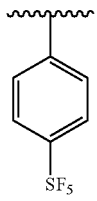
B66 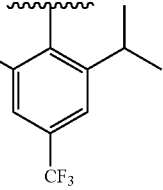
B67 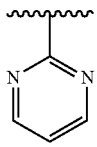
B68 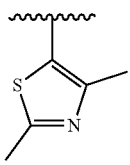

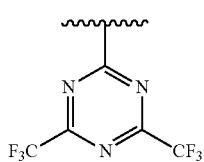 B69
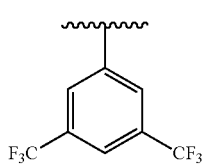 B70
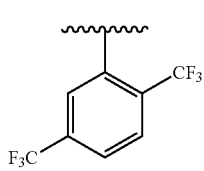 B71
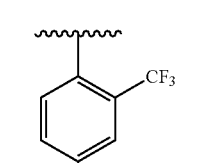 B72
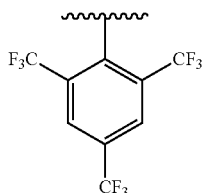 B73
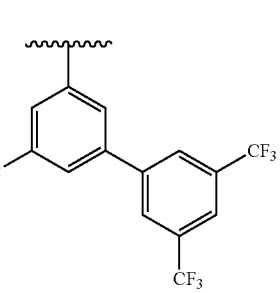 B74
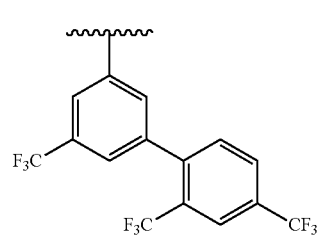 B75
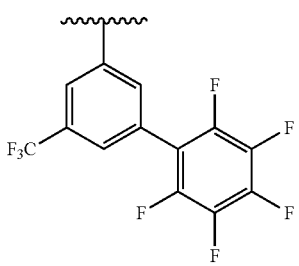 B76
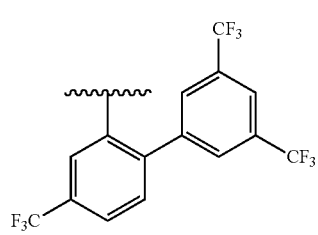 B77
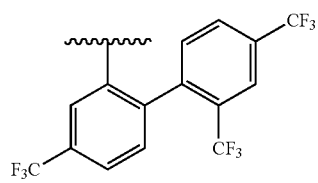 B78
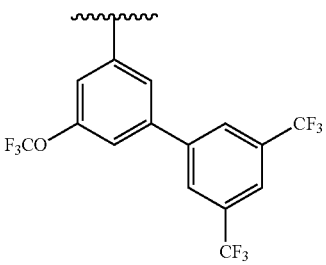 B79
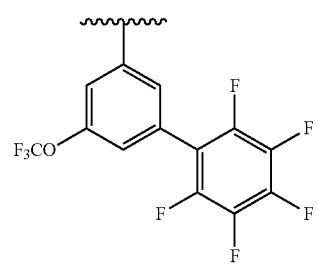 B80
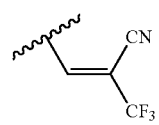 B81
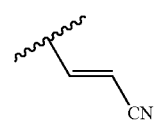 B82
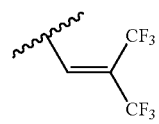 B83

-continued
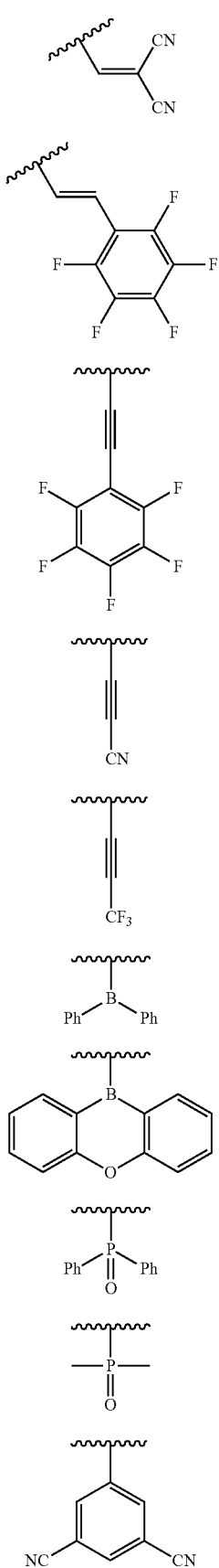
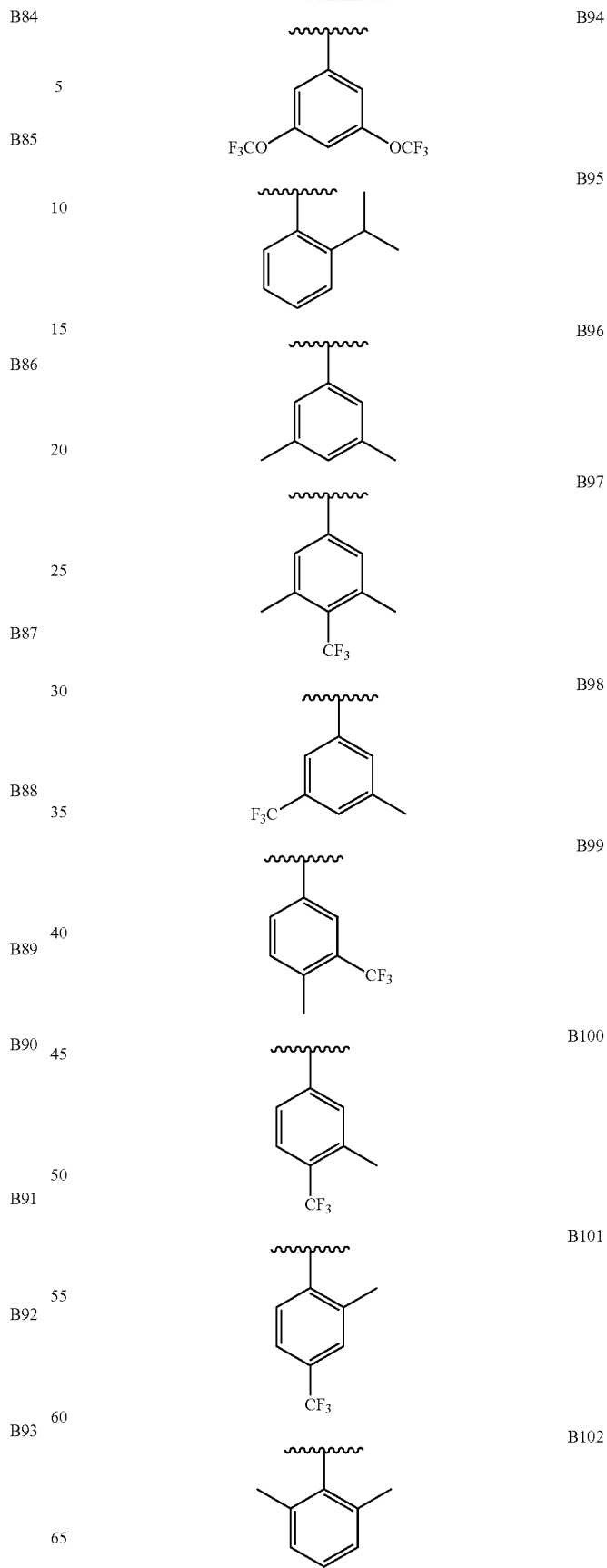

-continued
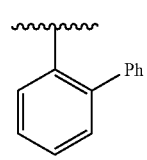 B103
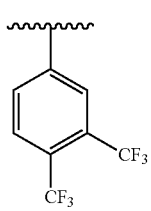 B104
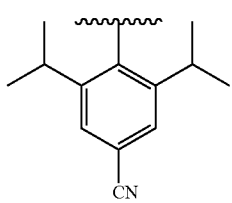 B105
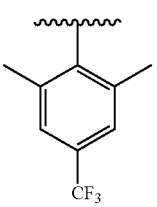 B106
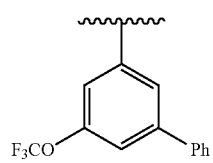 B107
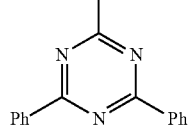 B108
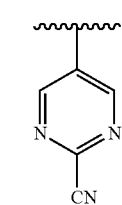 B109
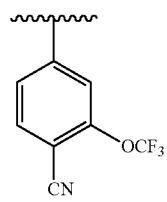 B110
-continued
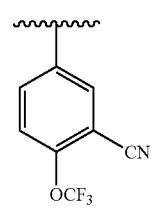 B111
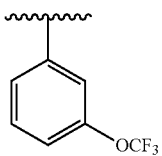 B112
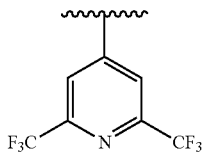 B113
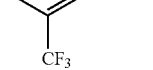 B114
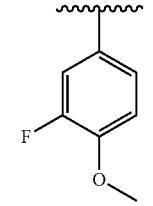 B115
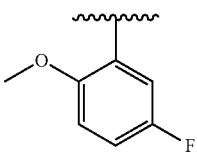 B116
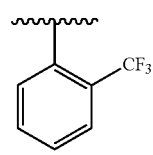 B117
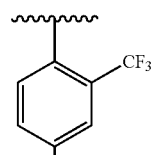 B118
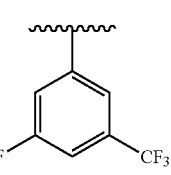 B119

B120 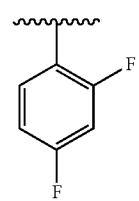

B121 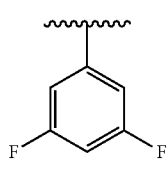

B122 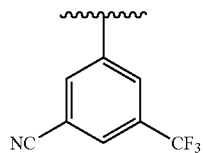

B123 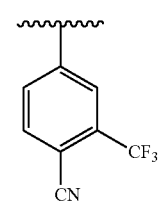

B124 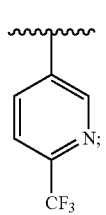

wherein ⁓ represents a position where R having the preceding structures is connected to Formula 1 and a position where $R_L$ having the preceding structures is connected to L; ⁓ further represents a position where $R_{NJ}$ is connected to N when J is selected from $NR_{NJ}$; and ⁓ further represents a position where $R_N$ is connected to N when W is selected from $NR_N$.

According to an embodiment of the present disclosure, wherein R, $R_L$, $R_N$, and $R_{NJ}$ are, at each occurrence identically or differently, selected from the group consisting of the following:

B6 

B13 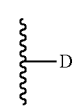

B14 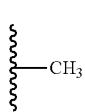

B16 

B17 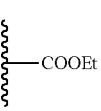

B18 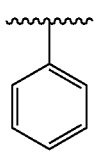

B25 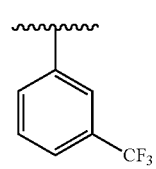

B27 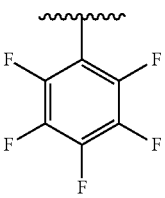

B28 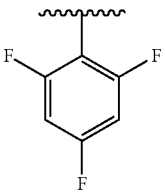

B30 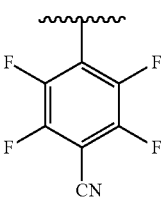

B31 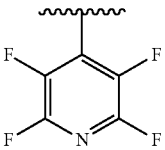

B40 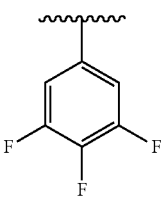

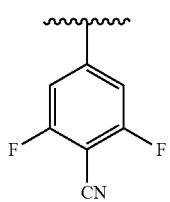 B41
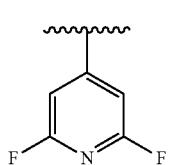 B42
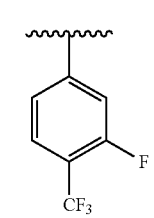 B44
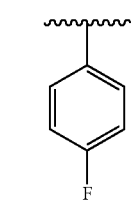 B53
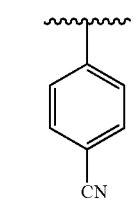 B54
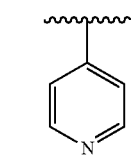 B55
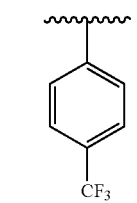 B57
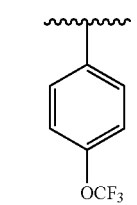 B58
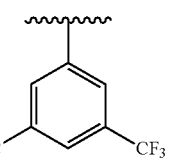 B70
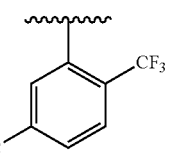 B71
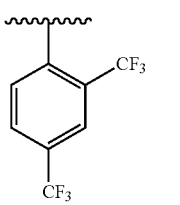 B72
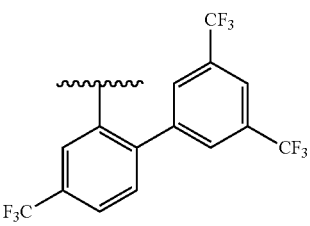 B77
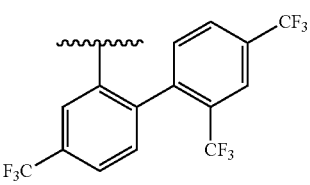 B78
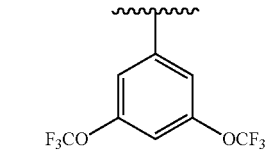 B94
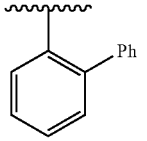 B103
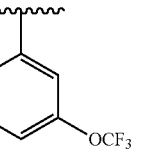 B112
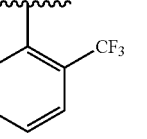 B117

-continued

B118

[Structure: phenyl with CF₃ ortho and F para]

B119

[Structure: phenyl with F, F, CF₃ substituents]

B120

[Structure: phenyl with F, F substituents]

B121

[Structure: phenyl with F, F substituents]

B122

[Structure: phenyl with NC and CF₃ substituents]

B123

[Structure: phenyl with CF₃ and CN substituents]

B124

[Structure: pyridine with CF₃]

wherein ⁓ represents a position where R having the preceding structures is connected to Formula 1 and a position where $R_L$ having the preceding structures is connected to L; ⁓ further represents a position where $R_{NJ}$ is connected to N when J is selected from $NR_{NJ}$; and ⁓ further represents a position where $R_N$ is connected to N when W is selected from $NR_N$.

According to an embodiment of the present disclosure, wherein substituents R, R', R", R''', $R_L$, $R_N$, $R_{NJ}$, $R_A$, and $R_B$ are each a group having at least one electron-withdrawing group.

According to an embodiment of the present disclosure, wherein substituents R, R', R", R''', $R_L$, $R_N$, $R_{NJ}$, $R_A$, and $R_B$ are groups that do not contain electron-rich groups, and examples of electron-rich groups are substituted or substituted amino groups. When the substituents contain electron-rich groups, the LUMO energy level becomes shallower than the LUMO energy level when the substituents contain electron-withdrawing groups, which is not conducive to hole injection.

According to an embodiment of the present disclosure, wherein the compound is selected from the group consisting of: Compound I-1 to Compound I-114, Compound II-1 to Compound II-108, Compound III-1 to Compound III-108, Compound IV-1 to Compound IV-108, Compound V-1 to Compound V-108, Compound VI-1 to Compound VI-108, Compound VII-1 to Compound VII-108, Compound VIII-1 to Compound VIII-108, Compound IX-1 to Compound IX-108, Compound X-1 to Compound X-108, Compound XI-1 to Compound XI-108, Compound XII-1 to Compound XII-108, Compound XIII-1 to Compound XIII-108, Compound XIV-1 to Compound XIV-108, Compound XV-1 to Compound XV-108, and Compound XVI-1 to Compound XVI-108, wherein specific structures of Compound I-1 to Compound I-114, Compound II-1 to Compound II-108, Compound III-1 to Compound III-108, Compound IV-1 to Compound IV-108, Compound V-1 to Compound V-108, Compound VI-1 to Compound VI-108, Compound VII-1 to Compound VII-108, Compound VIII-1 to Compound VIII-108, Compound IX-1 to Compound IX-108, Compound X-1 to Compound X-108, Compound XI-1 to Compound XI-108, Compound XII-1 to Compound XII-108, Compound XIII-1 to Compound XIII-108, Compound XIV-1 to Compound XIV-108, Compound XV-1 to Compound XV-108, and Compound XVI-1 to Compound XVI-108 are shown in claim 20.

According to an embodiment of the present disclosure, wherein the compound is selected from the group consisting of: Compound LIO-1 to Compound LIO-108, and Compound LIOA-1 to Compound LIOA-66, wherein specific structures of Compound LIO-1 to Compound LIO-108, and Compound LIOA-1 to Compound LIOA-66 are shown in claim 20.

According to an embodiment of the present disclosure, wherein the compound is selected from the group consisting of Compound II-IO-1 to Compound II-IO-60, wherein specific structures of Compound II-IO-1 to Compound II-IO-60 are shown in claim 20.

According to an embodiment of the present disclosure, disclosed is an organic electronic device which includes:
an anode,
a cathode, and
an organic layer disposed between the anode and the cathode, wherein the organic layer includes the compound described in any one of the preceding embodiments.

According to an embodiment of the present disclosure, disclosed is an electroluminescent device which includes:
an anode,
a cathode, and
an organic layer disposed between the anode and the cathode, wherein the organic layer includes the compound described in any one of the preceding embodiments.

According to an embodiment of the present disclosure, wherein the organic layer is a hole injection layer or a hole transporting layer, and the hole injection layer or the hole transporting layer is formed by the compound alone.

According to an embodiment of the present disclosure, wherein the organic layer is a hole injection layer or a hole transporting layer, and the hole injection layer or the hole transporting layer further includes at least one hole transporting material; wherein the molar doping ratio of the compound to the hole transporting material ranges from 10000:1 to 1:10000; and preferably, the molar ratio of the compound to the hole transporting material ranges from 10:1 to 1:100.

According to an embodiment of the present disclosure, wherein the electroluminescent device includes a plurality of stack layers between the anode and the cathode, and the plurality of stack layers include a first emissive layer and a second emissive layer, wherein a first stack layer includes the first emissive layer, a second stack layer includes the second emissive layer, and a charge generation layer is disposed between the first stack layer and the second stack layer, wherein the charge generation layer includes a p-type charge generation layer and an n-type charge generation layer;

wherein the p-type charge generation layer includes the compound; preferably, the p-type charge generation layer further includes at least one hole transporting material, wherein the molar doping ratio of the compound to the hole transporting material ranges from 10000:1 to 1:10000; preferably, wherein the molar doping ratio of the compound to the hole transporting material ranges from 10:1 to 1:100.

According to an embodiment of the present disclosure, wherein the hole transporting material includes a compound having a triarylamine unit, a spirodifluorene compound, a pentacene compound, an oligothiophene compound, an oligomeric phenyl compound, an oligomeric phenylenevinyl compound, an oligomeric fluorene compound, a porphyrin complex or a metal phthalocyanine complex.

According to an embodiment of the present disclosure, wherein the charge generation layer further includes a buffer layer disposed between the p-type charge generation layer and the N-type charge generation layer, and the buffer layer includes the compound.

According to an embodiment of the present disclosure, the electroluminescent device is prepared by vacuum evaporation.

According to an embodiment of the present disclosure, further disclosed is a compound formulation which includes the compound described in any one of the preceding embodiments.

Combination with Other Materials

The materials described in the present disclosure for a particular layer in an organic light-emitting device can be used in combination with various other materials present in the device. The combinations of these materials are described in more detail in U.S. Pat. App. No. 20160359122 at paragraphs 0132-0161, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light-emitting device may be used in combination with a variety of other materials present in the device. For example, compounds disclosed herein may be used in combination with a wide variety of hosts, transport layers, blocking layers, injection layers, electrodes and other layers that may be present. The combination of these materials is described in detail in paragraphs 0080-0101 of U.S. Pat. App. No. 20150349273, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatograph-mass spectrometry produced by SHIMADZU, gas chromatograph-mass spectrometry produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this patent.

The measured LUMO energy levels obtained herein were used to determine the electrochemical properties of the compound by cyclic voltammetry. The CorrTest CS120 electrochemical workstation produced by Wuhan Contest Instruments Corp., Ltd was used. The three-electrode working system was as follows: the platinum disk electrode was used as the working electrode, the $Ag/AgNO_3$ electrode was used as the reference electrode, and the platinum wire electrode was used as the auxiliary electrode. With anhydrous DCM as the solvent and 0.1 mol/L tetrabutylammonium hexafluorophosphate as the supporting electrolyte, the target compound was prepared into $10^{-3}$ mol/L solution. Before testing, nitrogen was introduced into the solution for 10 minutes to deoxidize. The instrument parameters were as follows: the scanning rate was 100 mV/s, the potential interval was 0.5 mV, and the test window was 1 V to 0.5 V.

Material Synthesis Example

The method for preparing the compound of the present disclosure is not limited herein. Typically, the following compounds are used as examples without limitations, and synthesis routes and preparation methods thereof are described below.

Synthesis Example 1: Synthesis of Compound I-6

Step 1: Synthesis of [Intermediate 1-b]

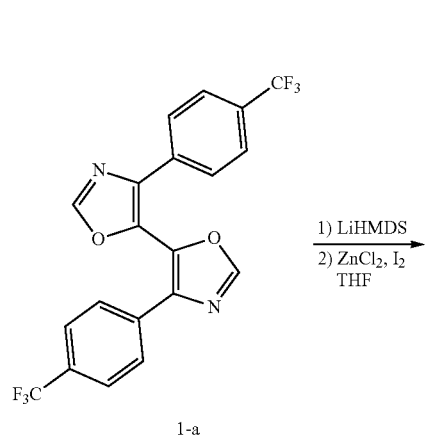

Step 2: Synthesis of [Intermediate 1-c]

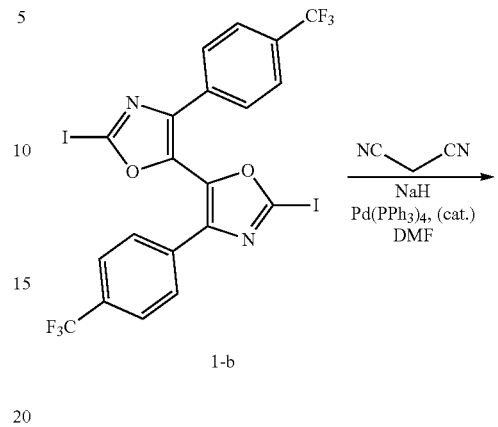

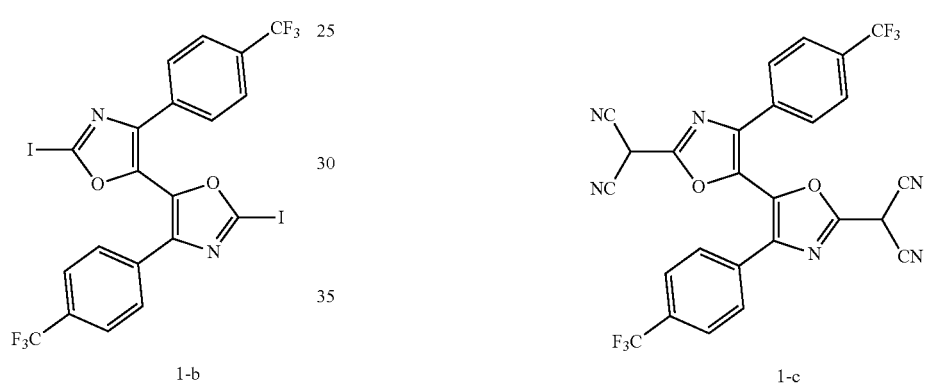

Under nitrogen protection, 1-a (9.20 g, 21.7 mmol) was added to THF (400 mL), the temperature was reduced to −72° C. (by ethanol/dry ice), LiHMDS solution (1.0 M, 100 mL) was slowly dropped, then the temperature was slowly raised to −30° C., and the reaction proceeded for 0.5 hours. $ZnCl_2$ (2.0 M, 50 mL) solution was dropped at −30° C., the temperature was slowly raised to 0° C., and the reaction proceeded for 10 minutes. Elemental solid iodine (23.2 g, 91.4 mmol) was added to the reaction solution, and the reaction proceeded at 0° C. for 2 hours. After the reaction was complete, the reaction was quenched with saturated $NH_4Cl$ solution. The reaction product was washed with saturated sodium thiosulfate solution, extracted with DCM, dried with anhydrous $Na_2SO_4$, and then filtered, and the solvent was removed through rotary evaporation. The product Intermediate 1-b (12.8 g, with a yield of 87%) as white solids was obtained by column chromatography on silica gel (with DCM/PE=1/1 as the eluent). $^1$H NMR (400 MHz, $CDCl_3$) δ=7.59 (d, J=8.4 Hz, 4H), 7.48 (d, J=8.4 Hz, 4H).

Under nitrogen protection, malononitrile (0.79 g, 11.9 mmol) was added to anhydrous DMF (30 mL), and NaH (0.48 g, 12.0 mmol, 60% content) was added portion-wise at 0° C. and stirred for 20 minutes. Intermediate 1-b (2.0 g, 3.0 mmol) and $Pd(PPh_4)_3$ (0.35 g, 3.0 mmol) were added, the temperature was raised to 90° C., and the reaction proceeded for 24 hours. After the complete conversion was achieved, the reaction product was poured into ice water, pH was adjusted to be less than 1 with 2N dilute hydrochloric acid, and then a large number of yellow solids were precipitated and then filtered. The filter cake was washed with a small amount of water and petroleum ether. The solid product was dissolved with acetone, the solvent was removed by rotary evaporation, and then the solid product was dried. The dried solid product was dissolved in dichloromethane (50 mL), filtered, and washed three times with dichloromethane (20 mL) to give Intermediate 1-c (1.3 g, with a yield of 80%) as yellow solids. $^1$HNMR (400 MHz, $d_6$-DMSO) δ=7.62 (d, J=6.8 Hz, 4H), 7.51 (d, J=6.8 Hz, 4H).

Step 3: Synthesis of Compound I-6

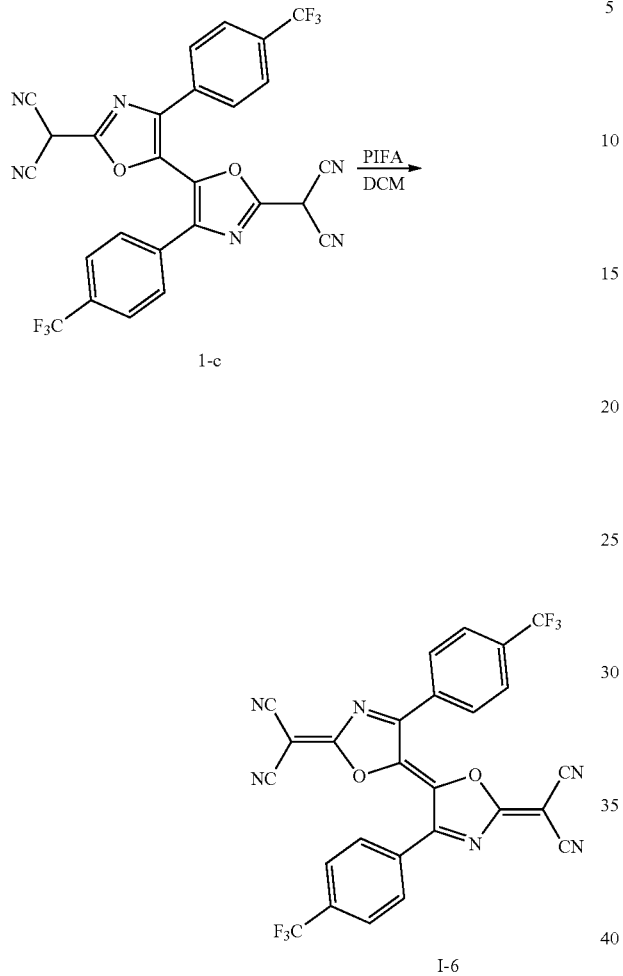

Under nitrogen protection, Intermediate 1-c (1.3 g, 2.4 mmol) was added to DCM (250 mL), the temperature was reduced to 0° C., PIFA (2.1 g, 4.9 mmol) was added portion-wise and stirred at room temperature for 3 days, and the solution was purple-black. After most of the solvent was removed by rotary evaporation, black solids were obtained by filtration. The black solids were washed twice with DCM/PE=1:1 (20 mL) and finally dried to give I-6 (1.0 g, with a yield of 77%) as black solids. $^1$HNMR (400 MHz, $d_6$-acetone) δ=8.34 (s, 2H), 8.06 (s, 2H). The product was confirmed as the target product with a molecular weight of 550. The CV of Compound I-6 was measured in DCM to obtain the LUMO of the compound, which was −4.81 eV. The black solids were heated for 12 hours under a vacuum condition of $1.9*10^{-4}$ Pa and at constant temperature of 280° C. and then sublimated to give the product Compound I-6 as black solids.

Synthesis Example 2: Synthesis of Compound I-8

Step 1: Synthesis of [Intermediate 2-b]

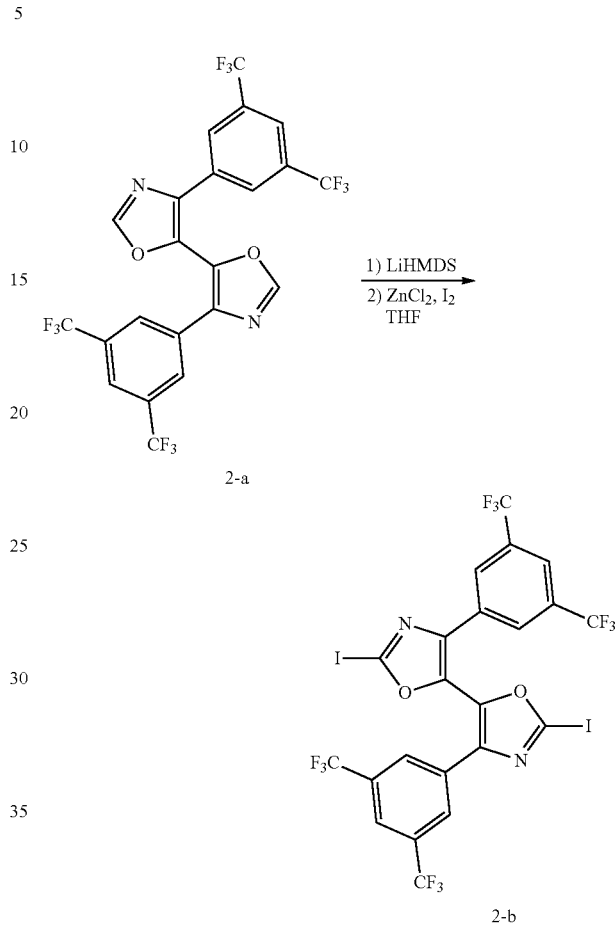

Under nitrogen protection, 2-a (11.5 g, 20.5 mmol) was added to THF (200 mL), the temperature was reduced to −72° C. (by ethanol/dry ice), LiHMDS solution (1.0 M, 85 mL) was slowly dropped, then the temperature was slowly raised to −30° C., and the reaction proceeded for 0.5 hours. $ZnCl_2$ (2.0 M, 43 mL) solution was dropped at −30° C., the temperature was slowly raised to 0° C., and the reaction proceeded for 10 minutes. Elemental solid iodine (22.0 g) was added to the reaction solution, and the reaction proceeded at 0° C. for 2 hours. After the reaction was complete, the reaction was quenched with saturated $NH_4Cl$ solution. The reaction product was washed with saturated sodium thiosulfate solution, extracted with DCM, dried with anhydrous $Na_2SO_4$, and filtered, and the solvent was removed through rotary evaporation. The product Intermediate 2-b (15.6 g, with a yield of 94%) as white solids was obtained by column chromatography on silica gel (with DCM/PE=1/1 as the eluent). $^1$HNMR (400 MHz, $CDCl_3$) δ=8.02 (s, 4H), 7.79 (s, 2H).

Step 2: Synthesis of [Intermediate 2-c]

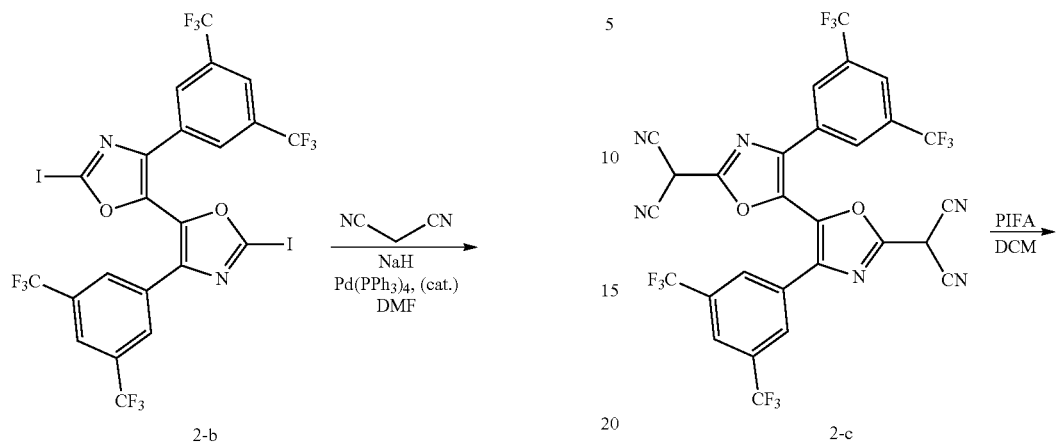

2-b

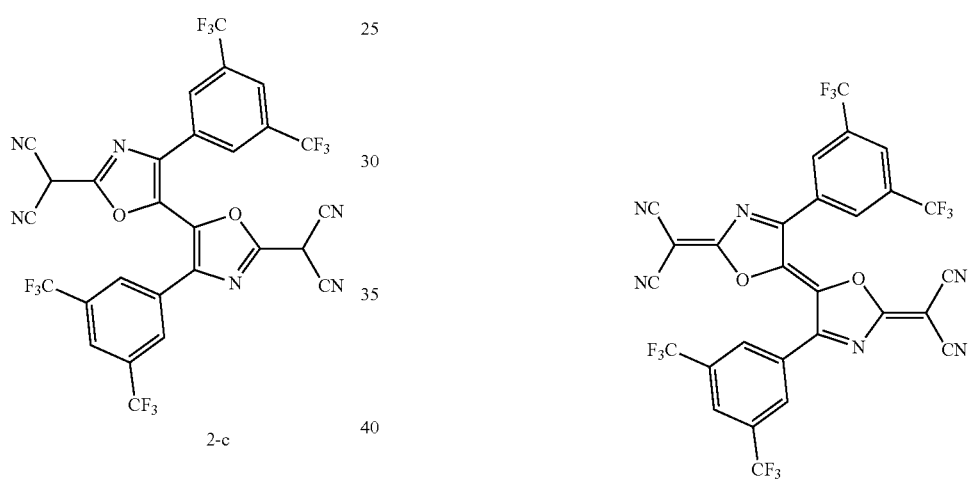

2-c

Under nitrogen protection, malononitrile (2.74 g, 41.4 mmol) was added to anhydrous DMF (100 mL), and NaH (1.67 g, 41.8 mmol, 60% content) was added portion-wise at 0° C. and stirred for 30 minutes. Then Intermediate 2-b (8.05 g, 9.9 mmol) and Pd(PPh$_4$)$_3$ (1.14 g) were added, the temperature was raised to 90° C., and the reaction proceeded for 24 hours. After the complete conversion was achieved, the reaction product was poured into ice water, pH was adjusted to be less than 1 with 2N dilute hydrochloric acid, and then a large number of yellow solids were precipitated and then filtered. The filter cake was washed with a large amount of water and petroleum ether. The solid product was dissolved with acetone, the solvent was removed by rotary evaporation, and then the solid product was dried. The dried solid product was then dissolved in dichloromethane (100 mL), filtered, washed three times with DCM/PE=1/1 (30 mL), and finally filtered to give 2-c (6.5 g, with a yield of 95%) as yellow solids. $^1$HNMR (400 MHz, d$_6$-acetone) δ=8.22 (s, 4H), 8.02 (s, 2H).

Step 3: Synthesis of Compound I-8

I-8

Under nitrogen protection, Intermediate 2-c (6.5 g, 9.4 mmol) was added to DCM (900 mL), the temperature was reduced to 0° C., PIFA (8.1 g, 18.9 mmol) was added portion-wise and stirred at room temperature for 3 days, and the solution was purple-black. After most of the solvent was removed by rotary evaporation, the solution was filtered, the filtered product was continuously washed twice with DCM/PE=1:1 and finally dried to give I-8 (5.3 g, with a yield of 82%) as black solids. The product was confirmed as the target product with a molecular weight of 686. The CV of Compound I-8 was measured in DCM to obtain the LUMO of the compound, which was −4.91 eV. The black solids were heated for 3 hours under a vacuum condition of $4.9*10^{-4}$ Pa and at a constant temperature of 270° C. and then sublimated to give the product Compound I-8 as black solids.

Synthesis Example 3: Synthesis of Compound I-109

Step 1: Synthesis of [Intermediate 5-b]

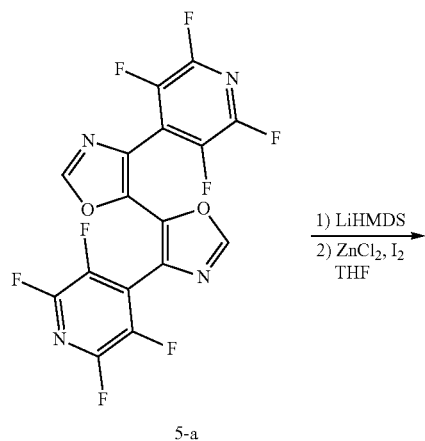

5-a

1) LiHMDS
2) ZnCl$_2$, I$_2$
THF

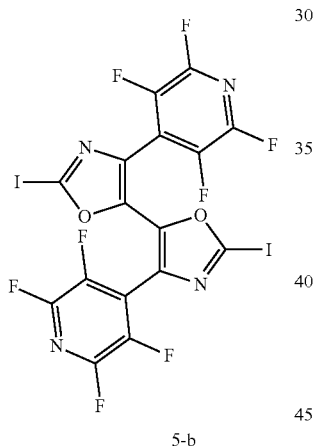

5-b

Step 2: Synthesis of [Intermediate 5-c]

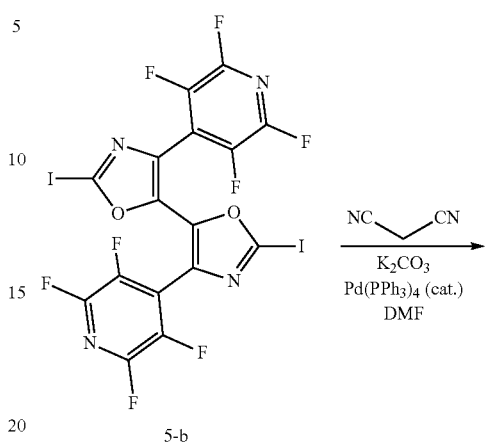

5-b

NC—CN
K$_2$CO$_3$
Pd(PPh$_3$)$_4$ (cat.)
DMF

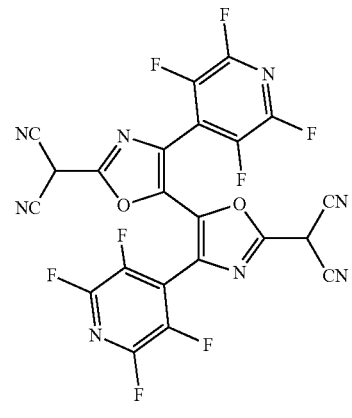

5-c

Under nitrogen protection, 5-a (10.3 g, 23.6 mmol) was added to THF (400 mL), the temperature was reduced to −72° C. (by ethanol/dry ice), LiHMDS solution (1.0 M, 60 mL) was slowly dropped, then the temperature was slowly raised to −30° C., and the reaction proceeded for 0.5 hours. ZnCl$_2$ (2.0 M, 30 mL) solution was dropped at −30° C., the temperature was slowly raised to 0° C., and the reaction proceeded for 10 minutes. Elemental solid iodine (20.1 g, 79.1 mmol) was added to the reaction solution, and the reaction proceeded at 0° C. for 2 hours. After the reaction was complete, the reaction was quenched with saturated NH$_4$Cl solution. The reaction product was washed with saturated sodium thiosulfate solution, extracted with DCM, dried with anhydrous Na$_2$SO$_4$, and then filtered, and the solvent was removed through rotary evaporation. The product Intermediate 5-b (13.7 g, with a yield of 84%) as white solids was obtained by column chromatography on silica gel (with DCM/THF/PE=4/1/4 as the eluent). $^{19}$FNMR (400 MHz, CDCl$_3$) δ=−88.73 (m, 4F), −139.23 (m, 4F).

Under nitrogen protection, malononitrile (2.2 g, 33 mmol) was added to anhydrous DMF (150 mL), and K$_2$CO$_3$ (4.45 g, 32.2 mmol) was added portion-wise at 0° C. and stirred for 20 minutes. Intermediate 5-b (10.4 g, 15.2 mmol) and Pd(PPh$_4$)$_3$ (1.55 g, 1.3 mmol) were added, the temperature was raised to 50° C., and the reaction proceeded for 10 hours. After the complete conversion was achieved, the reaction product was poured into ice water, pH was adjusted to be less than 1 with 2N dilute hydrochloric acid, and then a large number of yellow solids were precipitated and then filtered. The filter cake was washed with a small amount of water and petroleum ether. The solid product was dissolved with acetone, the solvent was removed by rotary evaporation, and then the solid product was dried. The dried solid product was dispersed with dichloromethane, filtered, and washed three times with dichloromethane (20 mL) to give Intermediate 5-c (3.9 g, with a yield of 46%) as yellow solids. $^{19}$FNMR (400 MHz, d$_6$-acetone) δ=−90.08 (m, 4F), −138.31 (m, 4F).

Step 3: Synthesis of Compound I-109

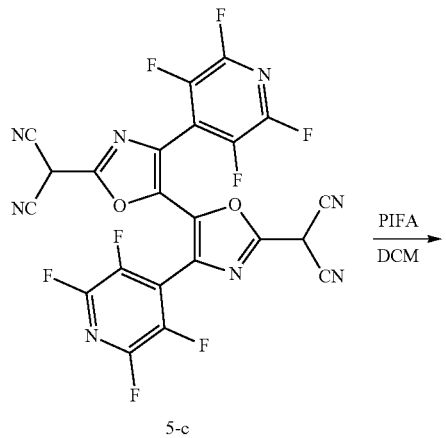

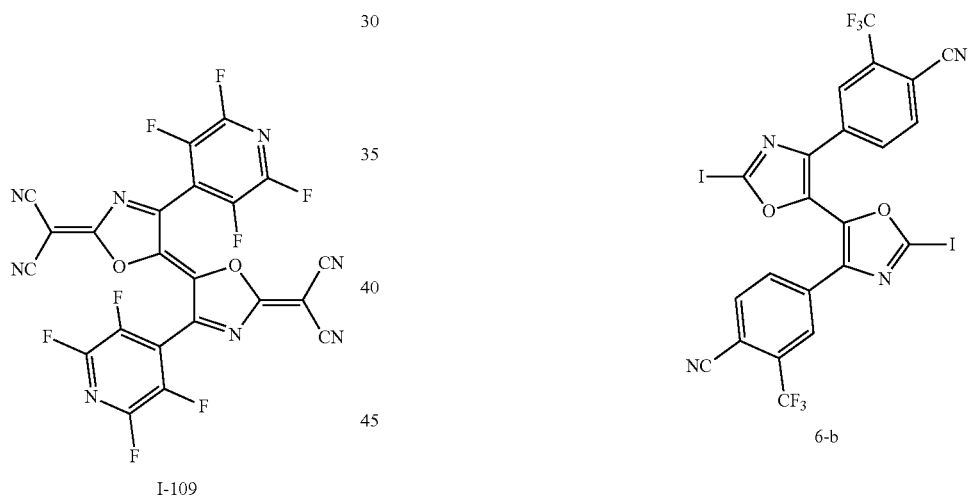

Under nitrogen protection, Intermediate 5-c (3.9 g, 6.9 mmol) was added to DCM (800 mL), the temperature was reduced to 0° C., PIFA (6.2 g, 14.4 mmol) was added portion-wise and stirred at room temperature for 2 days, and the solution was purple-black. After most of the solvent was removed by rotary evaporation, black solids were obtained by filtration. The black solids were washed twice with DCM/PE=1:1 (20 mL) and finally dried to give I-109 (2.4 g, with a yield of 62%) as black solids. $^{19}$FNMR (400 MHz, $d_6$-acetone) δ=−89.72 (s, 8F). The product was confirmed as the target product with a molecular weight of 560. The CV of Compound I-109 was measured in DCM to obtain the LUMO of the compound, which was −5.15 eV. The black solids were heated for 12 hours under a vacuum condition of $8.0*10^{-4}$ Pa and at a constant temperature of 300° C. and then sublimated to give the product Compound I-109 as black solids.

Synthesis Example 4: Synthesis of Compound I-110

Step 1: Synthesis of [Intermediate 6-b]

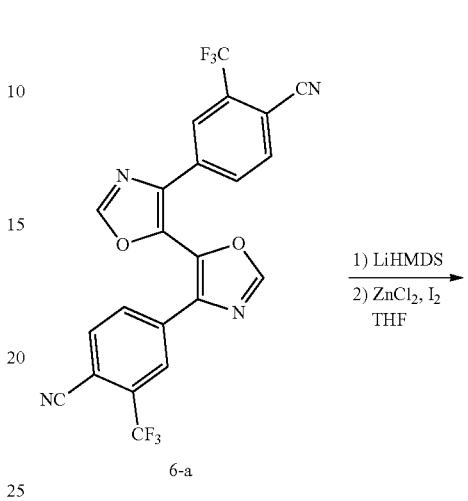

Under nitrogen protection, 6-a (10.4 g, 21.9 mmol) was added to THF (550 mL), the temperature was reduced to −72° C. (by ethanol/dry ice), LiHMDS solution (1.0 M, 70 mL) was slowly dropped, then the temperature was slowly raised to −30° C., and the reaction proceeded for 0.5 hours. $ZnCl_2$ (2.0 M, 35 mL) solution was dropped at −30° C., the temperature was slowly raised to 0° C., and the reaction proceeded for 10 minutes. Elemental solid iodine (18.5 g) was added to the reaction solution, and the reaction proceeded at 0° C. for 2 hours. After the reaction was complete, the reaction was quenched with saturated $NH_4Cl$ solution. The reaction product was washed with saturated sodium thiosulfate solution, extracted with DCM, dried with anhydrous $Na_2SO_4$, and filtered, and the solvent was removed through rotary evaporation. The product Intermediate 6-b (14.3 g, with a yield of 90%) as white solids was obtained by column chromatography on silica gel (with THF/PE=½ as the eluent). $^1$HNMR (400 MHz, $d_6$-acetone) δ=8.09 (m, 2H), 8.01 (d, J=8.4 Hz, 2H).

Step 2: Synthesis of [Intermediate 6-c]

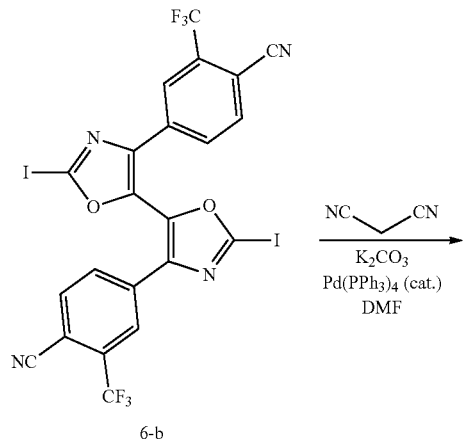

Step 3: Synthesis of Compound I-110

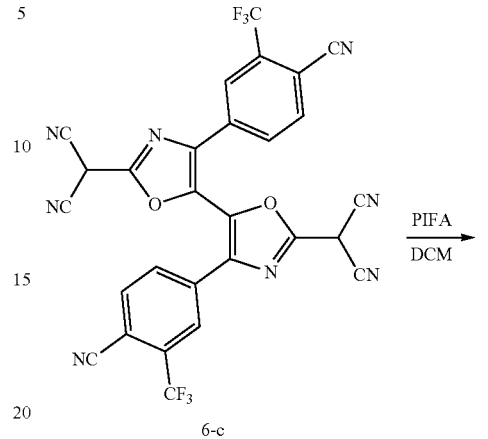

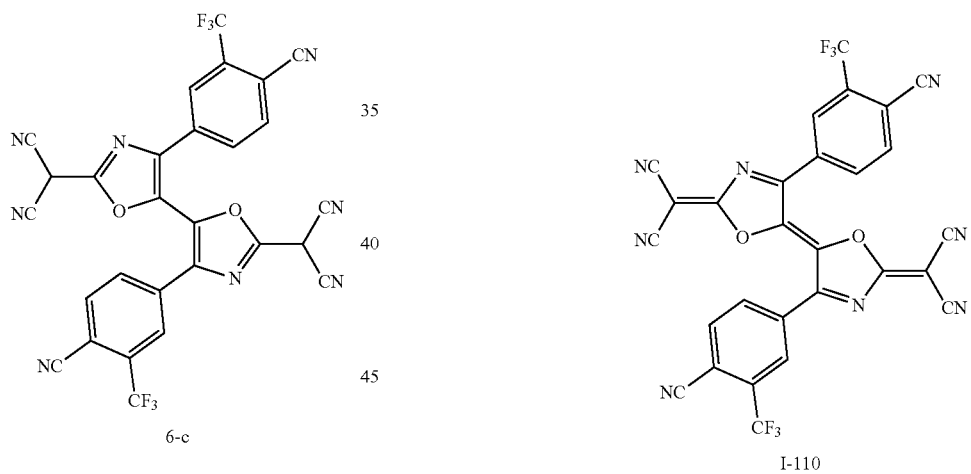

Under nitrogen protection, malononitrile (5.38 g, 81.5 mmol) was added to anhydrous DMF (200 mL), K₂CO₃ (11.2 g, 81.0 mmol), Intermediate 6-b (14.3 g, 19.7 mmol), and Pd(PPh₄)₃ (2.185 g) were added at 0° C., the temperature was raised to 80° C., and the reaction proceeded for 24 hours. After the complete conversion was achieved, the reaction product was poured into ice water, pH was adjusted to be less than 1 with 2N dilute hydrochloric acid, and then a large number of yellow solids were precipitated and then filtered. The filter cake was washed with a large amount of water and petroleum ether. The solid product was dissolved with acetone, the solvent was removed by rotary evaporation, and then the solid product was dried. The dried solid product was recrystallized with THF/PE=1/1 and finally filtered to give 6-c (11.3 g, with a yield of 95%) as yellow solids. ¹HNMR (400 MHz, d₆-acetone) δ=8.20 (m, 4H), 8.07 (d, J=8.0 Hz, 2H).

Under nitrogen protection, Intermediate 6-c (11.3 g, 18.8 mmol) was added to DCM (1200 mL), the temperature was reduced to 0° C., PIFA (16.2 g, 37.6 mmol) was added portion-wise and stirred at room temperature for 3 days, and the solution was purple-black. After most of the solvent was removed by rotary evaporation, the solution was filtered, the filtered product was continuously washed twice with DCM (100 mL) and finally dried to give I-110 (10.1 g, with a yield of 90%) as black solids. The product was confirmed as the target product with a molecular weight of 600. The CV of Compound I-110 was measured in DCM to obtain the LUMO of the compound, which was −4.97 eV. The black solids were heated for 12 hours under a vacuum condition of $1.1*10^{-4}$ Pa and at a constant temperature of 340° C. and then sublimated to give the product Compound I-110 as black solids.

Synthesis Example 5: Synthesis of Compound I-111

Step 1: Synthesis of [Intermediate 7-b]

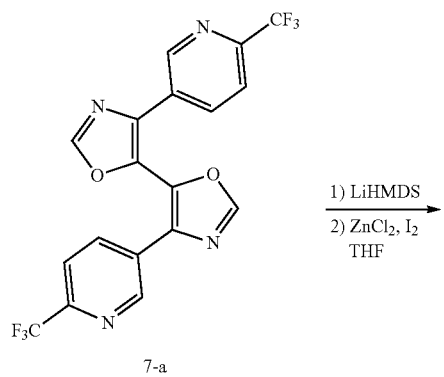

Step 2: Synthesis of [Intermediate 7-c]

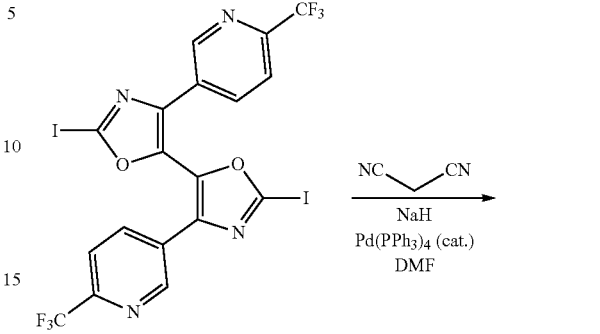

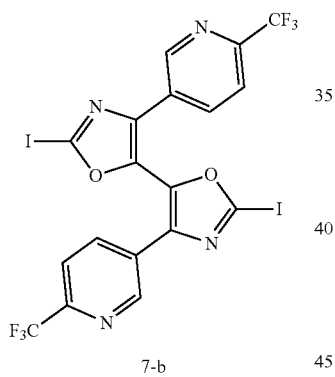

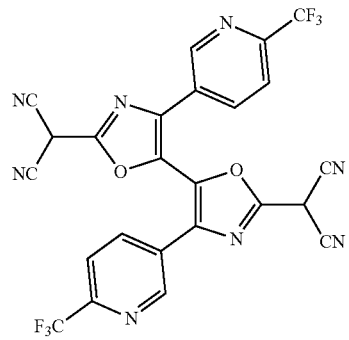

Under nitrogen protection, 7-a (6.3 g, 14.8 mmol) was added to THF (150 mL), the temperature was reduced to −72° C. (by ethanol/dry ice), LiHMDS solution (1.0 M, 34 mL) was slowly dropped, then the temperature was slowly raised to −30° C., and the reaction proceeded for 0.5 hours. ZnCl$_2$ (2.0 M, 17 mL) solution was dropped at −30° C., the temperature was slowly raised to 0° C., and the reaction proceeded for 10 minutes. Elemental solid iodine (11.5 g) was added to the reaction solution, and the reaction proceeded at 0° C. for 2 hours. After the reaction was complete, the reaction was quenched with saturated NH$_4$Cl solution. The reaction product was washed with saturated sodium thiosulfate solution, extracted with DCM, dried with anhydrous Na$_2$SO$_4$, and filtered, and the solvent was removed through rotary evaporation. The product Intermediate 7-b (8.4 g, with a yield of 97%) as white solids was obtained by column chromatography on silica gel (with DCM/EA/PE=4/1/4 as the eluent). $^1$HNMR (400 MHz, CDCl$_3$) δ=8.78 (s, 1H), 8.15 (d, J=8.0 Hz, 1H), 7.67 (d, J=8.0 Hz, 1H).

Under nitrogen protection, malononitrile (3.52 g, 53.3 mmol) was added to anhydrous DMF (130 mL), and NaH (2.138 g, 53.5 mmol, 60% content) was added at 0° C. and stirred for 20 minutes. Then Intermediate 7-b (8.3 g, 12.2 mmol) and Pd(PPh$_4$)$_3$ (1.435 g) were added, the temperature was raised to 80° C., and the reaction proceeded for 24 hours. After the complete conversion was achieved, the reaction product was poured into ice water, pH was adjusted to be less than 1 with 2N dilute hydrochloric acid, and then a large number of yellow solids were precipitated and then filtered. The filter cake was washed with a large amount of water and petroleum ether. The solid product was dissolved with acetone, the solvent was removed by rotary evaporation, and then the solid product was dried. The dried solid product was dispersed with dichloromethane and finally filtered to give 7-c (6.6 g, with a yield of 96%) as yellow solids. $^1$HNMR (400 MHz, d$_6$-DMSO) δ=8.75 (s, 1H), 8.08 (d, J=8.0 Hz, 1H), 7.67 (d, J=8.0 Hz, 1H).

Step 3: Synthesis of Compound I-111

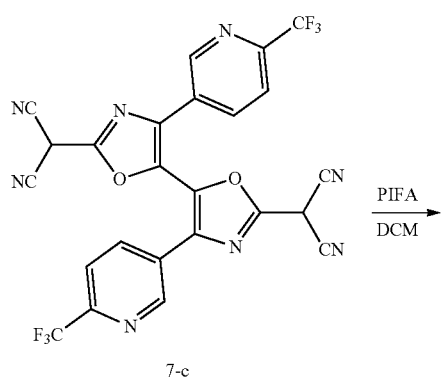

Synthesis Comparative Example 1: Synthesis of Compound S

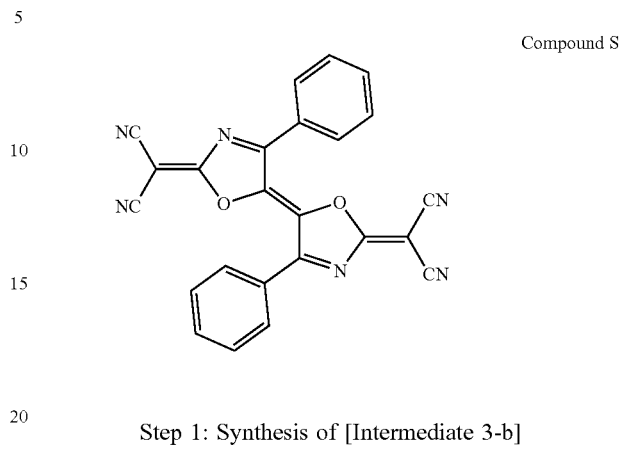

Step 1: Synthesis of [Intermediate 3-b]

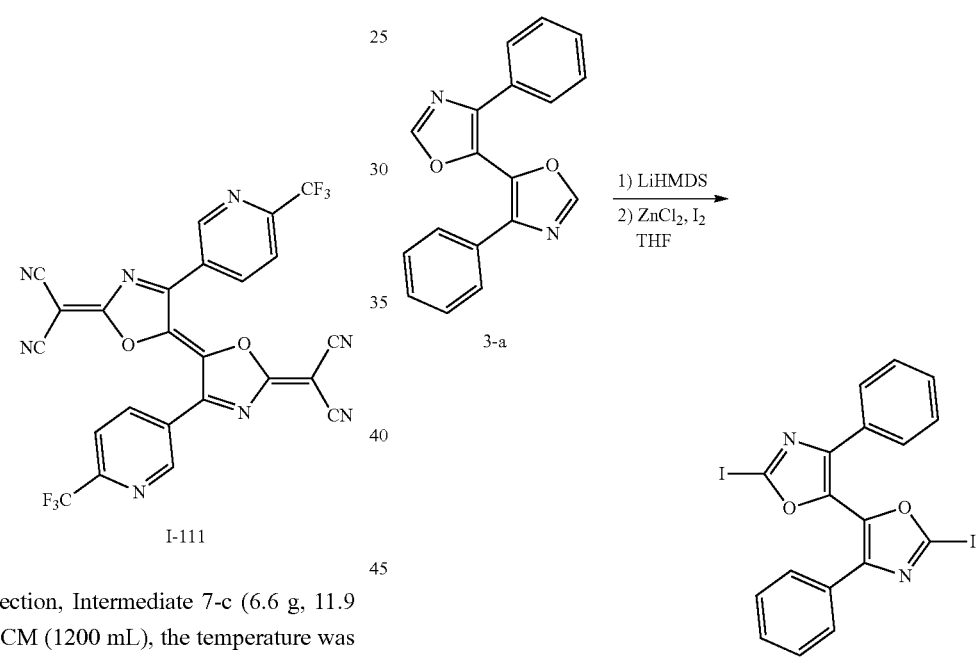

Under nitrogen protection, Intermediate 7-c (6.6 g, 11.9 mmol) was added to DCM (1200 mL), the temperature was reduced to 0° C., PIFA (10.7 g, 24.9 mmol) was added portion-wise and stirred at room temperature for 3 days, and the solution was purple-black. After most of the solvent was removed by rotary evaporation, the solution was filtered, the filtered product was continuously washed twice with DCM (100 mL) and finally dried to give I-111 (5.4 g, with a yield of 82%) as black solids. The product was confirmed as the target product with a molecular weight of 552. The CV of Compound I-111 was measured in DCM to obtain the LUMO of the compound, which was −4.92 eV. The black solids were heated for 12 hours under a vacuum condition of $7.7*10^{-4}$ Pa and at a constant temperature of 300° C. and then sublimated to give the product Compound I-111 as black solids.

Under nitrogen protection, 3-a (2.2 g, 7.6 mmol) was added to THF (50 mL), the temperature was reduced to −72° C. (by ethanol/dry ice), LiHMDS solution (1.0 M, 35 mL) was slowly dropped, then the temperature was slowly raised to −30° C., and the reaction proceeded for 0.5 hours. ZnCl$_2$ (2.0 M, 17 mL) solution was dropped at −30° C., the temperature was slowly raised to 0° C., and the reaction proceeded for 10 minutes. Elemental solid iodine (7.8 g) was added to the reaction solution, and the reaction proceeded at 0° C. for 2 hours. After the reaction was complete, the reaction was quenched with saturated NH$_4$Cl solution. The reaction product was washed with saturated sodium thiosulfate solution, extracted with DCM, dried with anhydrous Na$_2$SO$_4$, and filtered, and the solvent was removed through rotary evaporation. The product Intermediate 3-b (4.0 g, with a yield of 97%) as white solids was obtained by column chromatography on silica gel (with DCM/PE=½ as the eluent). ¹HNMR (400 MHz, CDCl₃) δ=7.51 (m, 4H), 7.24 (m, 6F).

Step 3: Synthesis of [Intermediate 3-c]

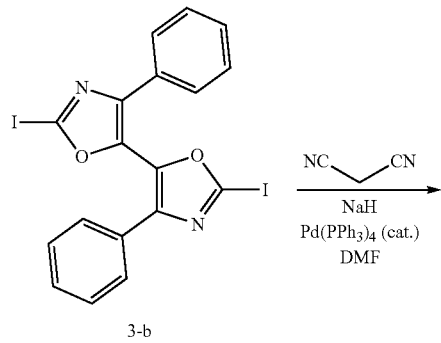

3-b

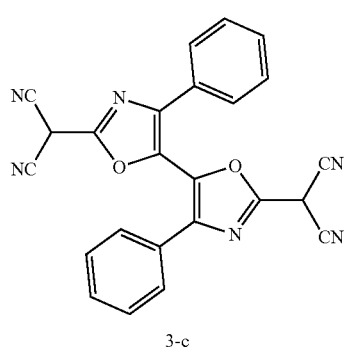

3-c

Under nitrogen protection, malononitrile (4.52 g, 68.4 mmol) was added to anhydrous DMF (160 mL), NaH (2.80 g, 70.0 mmol, 60% content) was added portion-wise at 0° C. and stirred for 30 minutes. Then Intermediate 3-b (8.8 g, 16.3 mmol) and Pd(PPh₄)₃ (1.88 g) were added, the temperature was raised to 90° C., and the reaction proceeded for 24 hours. After the complete conversion was achieved, the reaction product was poured into ice water, pH was adjusted to be less than 1 with 2N dilute hydrochloric acid, and then a large number of yellow solids were precipitated and then filtered. The filter cake was washed with a large amount of water and petroleum ether. The solid product was dissolved with acetone, and the solvent was subjected to rotary evaporation until the remaining acetone was about 50 mL. The mixture was filtered to give yellow solids. The yellow solids were washed three times with dichloromethane and finally filtered to give Intermediate 3-c (4.4 g, with a yield of 65%) as yellow solids. ¹HNMR (400 MHz, d₆-DMSO) δ=7.50 (m, 4H), 7.30 (m, 6H), 4.07 (b, 2H).

Step 4: Synthesis of Compound S

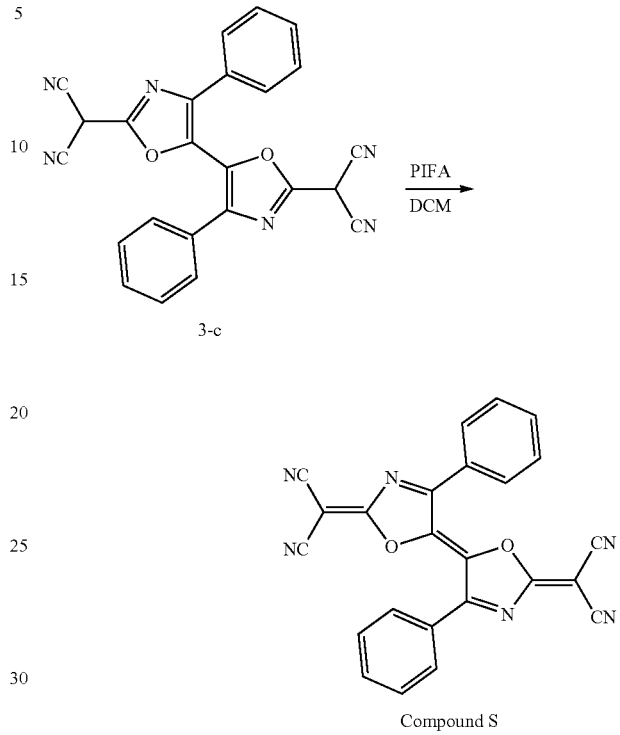

Compound S

Under nitrogen protection, Intermediate 3-c (4.4 g, 10.6 mmol) was added to DCM (600 mL), the temperature was reduced to 0° C., PIFA (9.3 g, 21.6 mmol) was added portion-wise and stirred at room temperature for 3 days, and the solution was purple-black. DCM was removed by rotary evaporation until the remaining DCM was about 20 mL, the solution was filtered, and the filtered product was continuously washed twice with DCM/PE=1:1 (50 mL) to finally give Compound S (2.9 g, with a yield of 66%) as black solids. The product was confirmed as the target product with a molecular weight of 414. The CV of Compound S was measured in DCM to obtain the LUMO of the compound, which was −4.70 eV The black solids were heated for 2 hours under a vacuum condition of $6.8*10^{-4}$ Pa and at a constant temperature of 300° C. and then sublimated to give the product Compound S as black solids.

Synthesis Comparative Example 2: Synthesis of Compound T

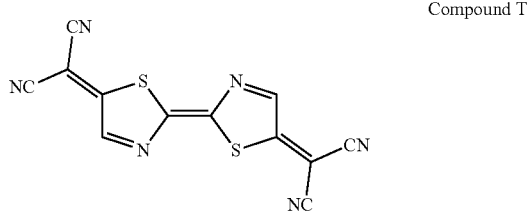

Compound T

Step 1: Synthesis of [Intermediate 4-b]

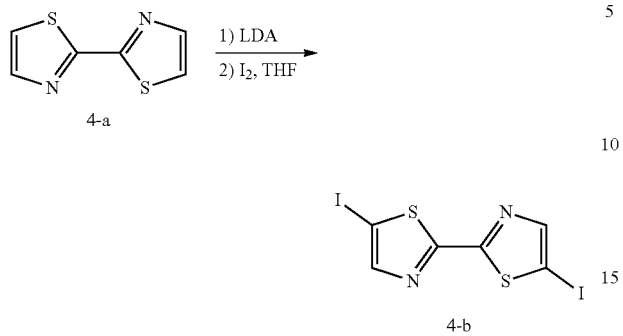

Under nitrogen protection, LDA (40 mL, 2.0 M) was added to THF (200 mL) at −72° C. (ethanol/dry ice), THF solution (60 mL) of 4-a (5.2 g, 31.0 mmol) was slowly dropped, and the reaction proceeded for 1 hour at a low temperature. The temperature was then raised to 0° C., THF (60 mL) solution of elemental iodine (17.3 g, 68.0 mmol) was slowly dropped, and the reaction proceeded at 0° C. for 1 hour. After the reaction was complete, the reaction was quenched with saturated $NH_4Cl$ solution. The reaction product was washed with saturated sodium thiosulfate solution, extracted with DCM, dried with anhydrous $Na_2SO_4$, the product was completely dissolved with DCM and then filtered with silica gel, and the solvent was removed through rotary evaporation. The product was recrystallized with DCM and THF to give product 4-b (8.9 g, with a yield of 68%) as yellow solids. $^1$HNMR (400 MHz, $CDCl_3$) δ=7.88 (s, 2H).

Step 2: Synthesis of [Intermediate 4-c]

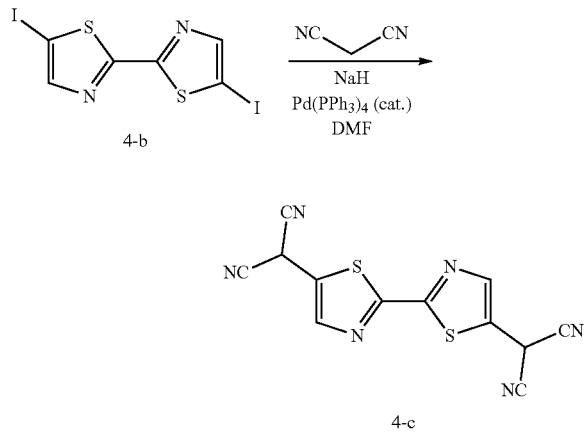

Under nitrogen protection, malononitrile (0.32 g, 4.8 mmol) was added to anhydrous DMF (12 mL), NaH (0.21 g, 5.2 mmol, 60% content) was added portion-wise at 0° C. and stirred for 30 minutes. Then Intermediate 4-b (0.5 g, 1.2 mmol) and $Pd(PPh_4)_3$ (0.14 g) were added, the temperature was raised to 100° C., and the reaction proceeded for 24 hours. After the complete conversion was achieved, the reaction product was poured into ice water, pH was adjusted to be less than 1 with 2N dilute hydrochloric acid, and then solids were precipitated and filtered. The solids were dissolved with acetone, and the solvent was removed through rotary evaporation, and then the solids were washed with DCM and finally filtered to give Intermediate 4-c (0.24 g, with a yield of 68%) as black solids. The solid product was directly used in the next step of the reaction.

Step 3: Synthesis of Compound T

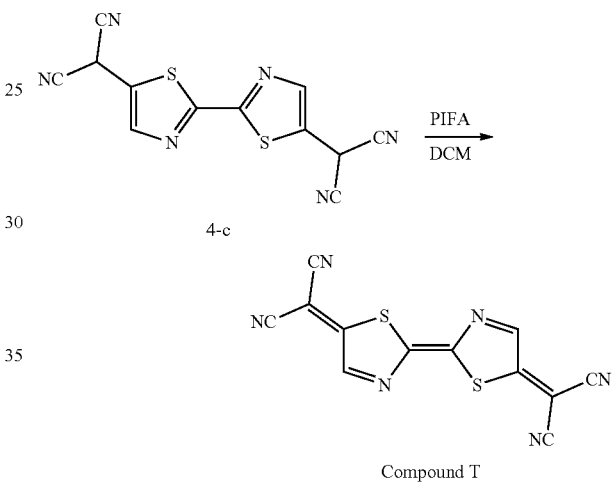

Under nitrogen protection, Intermediate 4-c (0.24 g) was added to DCM (80 mL), the temperature was reduced to 0° C., PIFA (0.69 g, 1.6 mmol) was added portion-wise and stirred at room temperature for 2 days, and the solution was purple-black. DCM was removed by rotary evaporation until the remaining DCM was about 10 mL, the solution was filtered, and the filtered product was continuously washed twice with DCM/PE=1:2 (10 mL) to finally give Compound T (0.16 g, with a yield of 67%) as black solids. $^1$HNMR (400 MHz, $CDCl_3$) δ=8.72 (s, 2H). The CV of Compound T was measured in DCM to obtain the LUMO of the compound, which was −4.64 eV. The black solids were heated for 30 minutes under a vacuum condition of $2.4*10^{-4}$ Pa and at a constant temperature of 300° C. and then sublimated, and no product Compound T was given.

For Compound T, since the substituent in the five-membered ring was just hydrogen, the molecule planarity was strong, and intermolecular force was strong, which leads to strong intermolecular stacking and difficulty in sublimation.

The persons skilled in the art should appreciate that the preceding preparation methods are merely illustrative. The persons skilled can obtain other compound structures of the present disclosure through the modifications of the preceding preparation methods.

Device Example

Device Example 1

A glass substrate having an Indium Tin Oxide (ITO) transparent electrode with a thickness of 80 nm was treated with oxygen plasma and UV ozone. Before deposition, the cleaned substrate was dried on a hot table in a glovebox. The following materials were sequentially deposited on the surface of the glass at a rate of 0.2 to 2 Angstroms per second at a vacuum degree of about $10^{-8}$ torr. First, Compound I-6 of the present disclosure was deposited onto the surface of the glass substrate to form a film with a thickness of 10 nm as a hole injection layer (HIL). Compound HT1 was deposited onto the preceding formed film to form a film with a thickness of 120 nm as a hole transporting layer (HTL). Compound EB1 was deposited onto the preceding formed film to form a film with a thickness of 5 nm as an electron blocking layer (EBL). Compound BH and Compound BD (with a weight ratio of 96:4) were co-deposited onto the preceding formed film to form a film with a thickness of 25 nm as an emissive layer (EML). Compound HB1 was deposited onto the preceding formed film to form a film with a thickness of 5 nm as a hole blocking layer (HBL). 8-hydroxyquinoline-lithium (Liq) and Compound ET1 (with a weight ratio of 60:40) were co-deposited onto the preceding formed film to form a film with a thickness of 30 nm as an electron transport layer (ETL). Finally, Liq was deposited as a film with a thickness of 1 nm as an electron injection layer (EIL), and aluminum with a thickness of 120 nm was deposited as a cathode. The device was then transferred back to the glovebox and encapsulated with a glass lid and a moisture absorbent to complete the device.

Device Example 2

The device in Device Example 2 was prepared in the same manner as that in Device Example 1, except that HIL was formed by using Compound I-8 rather than Compound I-6.

Device Example 3

The device in Device Example 3 was prepared in the same manner as that in Device Example 1, except that Compound I-6 and Compound HT1 (with a weight ratio of 7:93) were co-deposited on the surface of the glass substrate to form a film with a thickness of 10 nm as the hole injection layer (HIL).

Device Example 4

The device in Device Example 4 was prepared in the same manner as that in Device Example 1, except that Compound I-6 and Compound HT1 (with a weight ratio of 10:90) were co-deposited on the surface of the glass substrate to form a film with a thickness of 10 nm as the hole injection layer (HIL).

Device Example 5

The device in Device Example 5 was prepared in the same manner as that in Device Example 1, except that Compound I-8 and Compound HT1 (with a weight ratio of 3:97) were co-deposited on the surface of the glass substrate to form a film with a thickness of 10 nm as the hole injection layer (HIL).

Device Example 6

The device in Device Example 6 was prepared in the same manner as that in Device Example 1, except that Compound I-109 and Compound HT1 (with a weight ratio of 3:97) were co-deposited on the surface of the glass substrate to form a film with a thickness of 10 nm as the hole injection layer (HIL).

Device Example 7

The device in Device Example 7 was prepared in the same manner as that in Device Example 1, except that Compound I-111 and Compound HT1 (with a weight ratio of 3:97) were co-deposited on the surface of the glass substrate to form a film with a thickness of 10 nm as the hole injection layer (HIL).

Device Comparative Example 1

The device in Device Comparative Example 1 was prepared in the same manner as that in Device Example 1, except that HIL was formed by using Comparative Compound S rather than Compound I-6.

Device Comparative Example 2

The device in Device Comparative Example 2 was prepared in the same manner as that in Device Example 1, except that Compound HI1 and Compound HT1 (with a weight ratio of 7:93) were co-deposited on the surface of the glass substrate to form a film with a thickness of 10 nm as the hole injection layer (HIL).

Device Comparative Example 3

The device in Device Comparative Example 3 was prepared in the same manner as that in Device Example 1, except that Compound HI1 and Compound HT1 (with a weight ratio of 3:97) were co-deposited on the surface of the glass substrate to form a film with a thickness of 10 nm as the hole injection layer (HIL).

Device Comparative Example 4

The device in Device Comparative Example 4 was prepared in the same manner as that in Device Example 1, except that Compound S and Compound HT1 (with a weight ratio of 7:93) were co-deposited on the surface of the glass substrate to form a film with a thickness of 10 nm as the hole injection layer (HIL).

Device Comparative Example 5

The device in Device Comparative Example 5 was prepared in the same manner as that in Device Example 1, except that Compound S and Compound HT1 (with a weight ratio of 10:90) were co-deposited on the surface of the glass substrate to form a film with a thickness of 10 nm as the hole injection layer (HIL).

Detailed structures and thicknesses of layers of the devices are shown in Table 1. The layers using more than one material are obtained by doping different compounds at weight proportions as recorded in Table 1.

TABLE 1

Device structures in Device Examples and Comparative Examples

| Device ID | HIL | HTL | EBL | EML | HBL | ETL |
|---|---|---|---|---|---|---|
| Example 1 | Compound I-6 (10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Example 2 | Compound I-8 (10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Comparative Example 1 | Compound S (10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Example 3 | Compound I-6:Compound HT1 (7:93, 10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Comparative Example 2 | Compound HI1:Compound HT1 (7:93, 10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Comparative Example 4 | Compound S:Compound HT1 (7:93, 10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Example 4 | Compound I-6:Compound HT1 (10:90, 10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Comparative Example 5 | Compound S:Compound HT1 (10:90, 10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Example 5 | Compound I-8:Compound HT1 (3:97, 10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Example 6 | Compound I-109:Compound HT1 (3:97, 10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Example 7 | Compound I-111:Compound HT1 (3:97, 10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Comparative Example 3 | Compound HI1:Compound HT1 (3:97, 10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |

The structures of the materials used in the device are as follows:
HI1
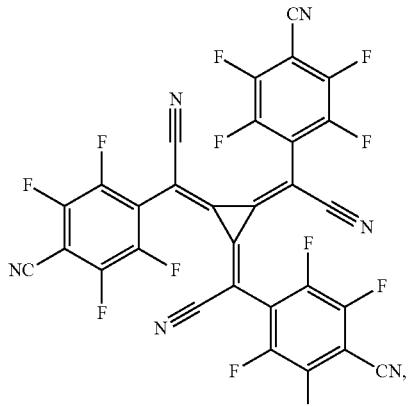
I-6
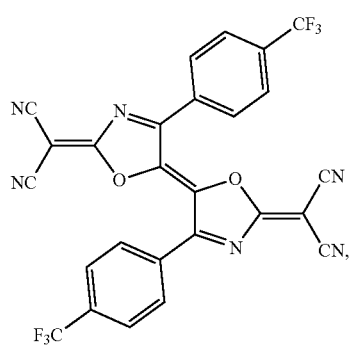
I-8
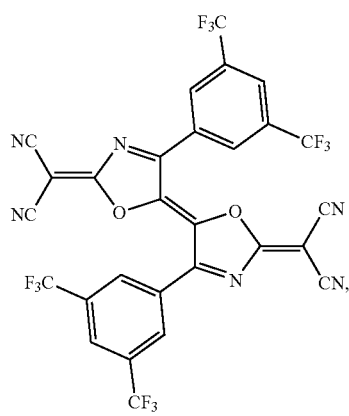
I-109
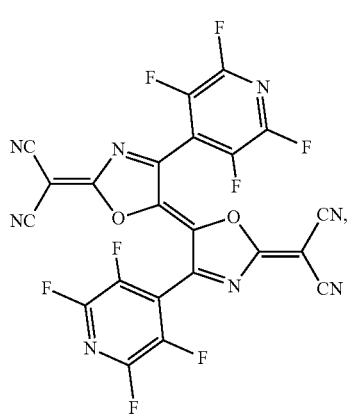
I-111
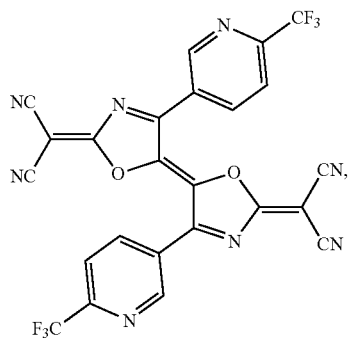
Compound S
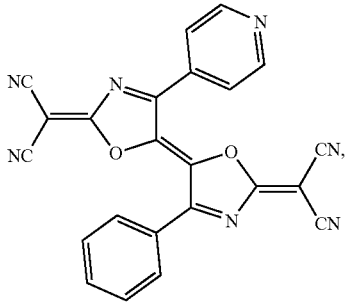
HT1
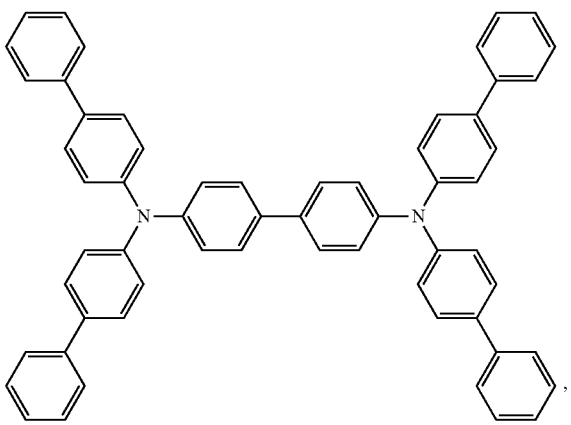
EB1
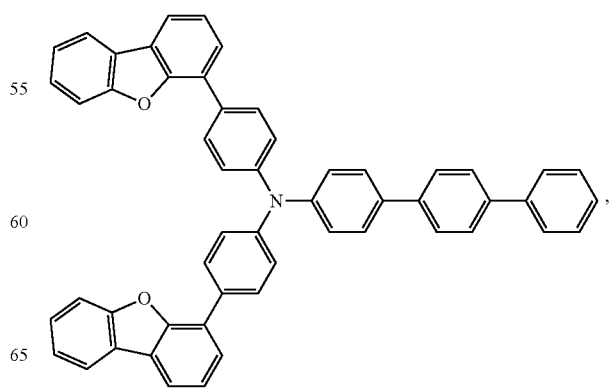

BH

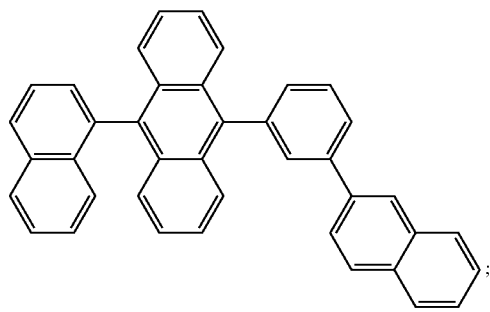

BD

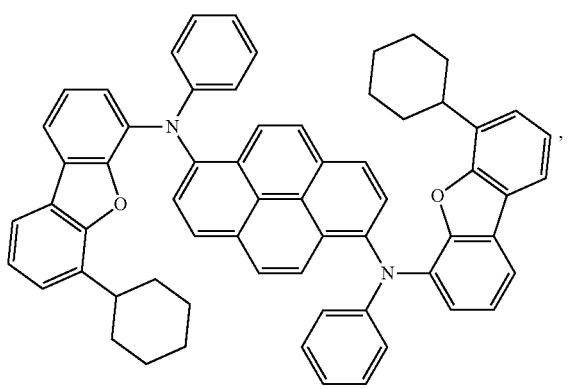

HB1

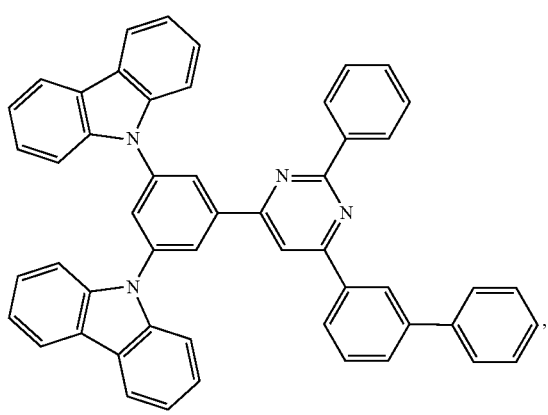

and

ET1

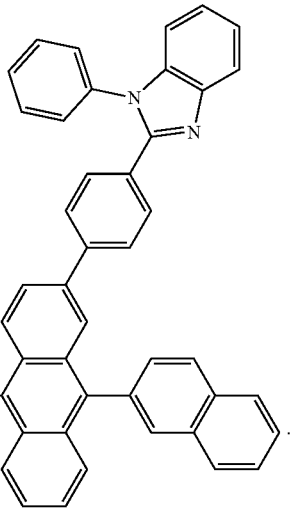

For the device data of Example 1, Example 2, and Comparative Example 1, IVL characteristics were measured at 10 mA/cm$^2$, and the voltage, external quantum efficiency (EQE), power efficiency (PE), and lifetime (LT97) of the devices are recorded and displayed in Table 2.

TABLE 2

Device data of Example 1, Example 2, and Comparative Example 1

| Device No. | Voltage (V) | PE (lm/W) | EQE (%) | LT97 (h) |
| --- | --- | --- | --- | --- |
| Example 1 | 4.39 | 4.39 | 8.26 | 912 |
| Example 2 | 4.52 | 4.30 | 8.35 | 313 |
| Comparative Example 1 | 4.74 | 3.83 | 7.51 | 6 |

As can be seen from Table 2, with the comparison between Examples 1 and 2 and Comparative Example 1, compared to the device in which Compound S was used as the hole injection layer alone, when Compound I-6 and Compound I-8 of the present disclosure each were used as the hole injection layer material alone, the voltage of the device was lower, the PE value was increased by more than 12%, and the EQE was also improved. Especially, the lifetime of the device was increased by more than 50 times. It indicates that due to the introduction of substituents having the electron-withdrawing group, Compounds I-6 and I-8 disclosed in the present disclosure have a better hole injection ability than Compound S. The performance of the compounds of the present disclosure when used in the hole injection layer alone proves that the compounds of the present disclosure are a class of excellent hole injection materials.

For the device data of Examples 3 to 7 and Comparative Examples 2 to 5, IVL characteristics were measured at 10 mA/cm$^2$, and the voltage, power efficiency (PE), and lifetime (LT97) of the devices were recorded and displayed in Tables 3 to 5.

TABLE 3

Device data of Example 3, Comparative Example 2, and Comparative Example 4

| Device No. | Voltage (V) | PE (lm/W) | LT97 (h) |
|---|---|---|---|
| Example 3 | 4.29 | 5.03 | 1132 |
| Comparative Example 2 | 4.25 | 5.09 | 757 |
| Comparative Example 4 | 6.76 | 4.37 | 160 |

As can be seen from Table 3, with the comparison between Example 3 and Comparative Example 2, when Compound I-6 of the present disclosure and Compound HT1 (7:93) were used in the hole injection layer, the voltage, PE, and EQE of the device were similar to these of the device in which Compound HI1 and Compound HT1 (7:93) were used in the hole injection layer, but the lifetime of the device was increased by about 50%. With the comparison between Example 3 and Comparative Example 4, when Compound S and Compound HT1 (7:97) were used in the hole injection layer of the device of Comparative Example 4, the voltage of the device was significantly increased, the PE of the device was also significantly decreased, and the lifetime of the device was far shorter than the lifetime of the device of Example 3. The lifetime of the device of Example 3 was increased by as much as six times as the lifetime of the device of Comparative Example 4, and since the lifetime of the device of Comparative Example 4 was too short, the compounds in Comparative Example 4 could not meet the requirements of commercial materials. It can be seen that, compared with the use of Compound HI1 and Compound S in the hole injection layer, when the compounds the present disclosure are doped in the hole injection material, the compounds of the present disclosure can obtain excellent performance that is same as or better than the commercial HI1, and thus have considerable commercial prospects.

TABLE 4

Device data of Example 4 and Comparative Example 5

| Device No. | Voltage (V) | PE (lm/W) | LT97 (h) |
|---|---|---|---|
| Example 4 | 4.26 | 4.95 | 710 |
| Comparative Example 5 | 6.12 | 4.48 | 157 |

As can be seen from Table 4, with the comparison between Example 4 and Comparative Example 5, when the proportion of both dopant Compound I-6 and Compound S in the hole injection layer was increased to 10%, compared with the compound S, Compound I-6 increased the lifetime of the device by 3.52 times and enabled the device to have a lower driving voltage and higher power efficiency.

TABLE 5

Device data of Example 5, Example 6, Example 7, and Comparative Example 3

| Device No. | Voltage (V) | PE (lm/W) | LT97 (h) |
|---|---|---|---|
| Example 5 | 4.20 | 5.14 | 781 |
| Example 6 | 4.18 | 5.12 | 780 |
| Example 7 | 4.19 | 5.14 | 778 |
| Comparative Example 3 | 4.21 | 5.10 | 777 |

With the comparison between Examples 5, 6, and 7 and Comparative Example 3, compared with Comparative Example 3 using commercial material HI1, for Examples in which Compounds I-8, I-109, and I-111 disclosed in the present disclosure were respectively used in HIL, the devices were improved in all aspects of device performance of voltage, lifetime, and efficiency. It is fully proved that compared with the use of Compound HI1 in the hole injection material, when Compounds I-8, I-109, and I-111 of the present disclosure are doped in the hole injection material, the compounds of the present disclosure can obtain excellent device performance that is the same as or better than the commercial HI1 and thus have considerable commercial prospects.

Compound I-6, Compound I-8, Compound I-109, and Compound I-111 are compounds of the present disclosure having the structure of Formula 1, in which the substituent R is a group having an electron-withdrawing group, while Compound S and Compound T are comparative compounds, in which the substituent R is a group having no electron-withdrawing group. It can be seen from the device results that when the compounds of the present disclosure in which R is a substituent having an electron-withdrawing group are applied to the devices, these compounds can obtain more excellent device results, whether each of them is used alone or doped. When these compounds are doped in the hole injection material, the compounds can achieve the performance that is the same as or better than the performance of commercial HI1 and thus have considerable commercial prospects.

The LUMO energy levels of Compounds I-6, I-8, I-109, and I-111 of the present disclosure and Comparative Compound S and T were tested by cyclic voltammetry, and the results are shown in the following table.

TABLE 6

LUMO energy levels of materials

| | Compound No. | | | | | |
|---|---|---|---|---|---|---|
| Item | I-6 | I-8 | I-109 | I-111 | Compound S | Compound T |
| LUMO energy level/eV | −4.81 | −4.91 | −5.15 | −4.92 | −4.70 | −4.64 |

As can be seen from Table 6, the actual measured LUMO energy levels of Compounds S and T were not as deep as the LUMO energy levels of Compounds I-6, I-8, I-109, and I-111, which indicates that the compounds of the present disclosure having the structure of Formula 1 can have deeper LUMO energy levels when the R substituent is an electron-withdrawing group than the compounds when R is not an electron-withdrawing group and thus are more suitable for being used as the hole injection material in the organic electronic device.

In conjunction with material device data, Compound I-6, Compound I-8, Compound I-109, and Compound I-111 have better device performance than Compound S, which indicates that the deep LUMO energy level of the compound is very important to the device performance of the compound. When the material was used as the dopant of the hole injection layer, the deeper the LUMO energy level, the better the device performance. The LUMO energy level of Compound T was shallower than the LUMO energy level of Compound S, so it can be inferred that the hole injection ability of Compound T is also insufficient. Especially, materials with a LUMO energy level below −4.80 eV (LUMO energy level of −5.20 eV and below calculated by DFT) will be excellent hole injection materials.

The LUMO energy levels of some of the compounds disclosed in the present disclosure were obtained by calculating [GAUSS-09, B3LYP/6-311G (d)] by DFT, and the related compounds and their LUMO values are shown in Tables 7 and 8.

TABLE 7

| DFT calculation results (n = 0) | |
|---|---|
| Compound | LUMO (eV) |
| I-3 | −5.36 |
| I-5 | −5.35 |
| I-6 | −5.20 |
| I-8 | −5.36 |
| I-10 | −5.32 |
| III-3 | −5.26 |
| I-109 | −5.62 |
| I-110 | −5.51 |
| I-111 | −5.34 |
| III-5 | −5.22 |
| III-8 | −5.28 |
| VII-3 | −5.34 |
| VII-5 | −5.30 |
| VII-8 | −5.37 |
| VIII-3 | −5.34 |
| VIII-5 | −5.30 |
| VIII-8 | −5.37 |
| IX-8 | −5.25 |
| X-5 | −5.19 |
| X-8 | −5.25 |
| X-10 | −5.20 |
| II-IO-3 | −5.66 |
| II-IO-4 | −5.77 |
| II-IO-7 | −5.88 |
| II-IO-8 | −5.77 |

TABLE 8

| DFT calculation results | |
|---|---|
| Compound | LUMO (eV) |
| LIO-22 | −5.21 |
| LIO-23 | −5.25 |
| LIOA-3 | −5.31 |
| LIOA-5 | −5.35 |
| LIOA-6 | −5.23 |
| LIOA-19 | −5.74 |
| LIOA-21 | −5.68 |
| LIOA-22 | −5.56 |
| LIOA-24 | −5.55 |

From the DFT theoretical calculations in Tables 7 and 8, it can be seen that the compounds of the present disclosure having the structure of Formula 1 have deep LUMO energy levels and thus are suitable for being used as the hole injection material in the organic electronic device. When L is selected from

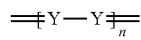

and n=0, for example, some of the compounds shown in Table 7, in which at least one of R and $R_N$ having at least one electron-withdrawing group, have the LUMO energy levels of −5.20 eV and below. For example, the calculated LUMO energy levels of Compounds I-6 and I-8 each were much deeper than the LUMO energy level of Compound S (the LUMO energy level of Compound S calculated by the same calculation method is −4.83 eV). The LUMO energy level of Compound I-8 was deeper than the LUMO energy level of Compound I-6 due to the introduction of more electron-withdrawing groups on the substituent R in Compound I-8. The LUMO energy levels of the compounds in which R and $R_L$ are both groups having the electron-withdrawing group were also deeper than the LUMO energy levels of the compounds in which one of R and $R_L$ has at least one electron-withdrawing group, for example, Compound LIOA-23 vs. Compound LIOA-5.

In summary, it can be concluded from the preceding results that the compounds having the structure of Formula 1 of the present disclosure have the importance of the electron-withdrawing group. The compounds of the present disclosure are very important charge transfer materials, especially have incomparable advantages in hole transporting, are easy to prepare organic semiconductor devices, and are suitable for different types of organic electronic devices, including but not limited to fluorescent OLEDs, phosphorescent OLEDs, white OLEDs, laminated OLEDs, OTFTs, OPVs, etc.

It should be understood that various embodiments described herein are examples and not intended to limit the scope of the present disclosure. Therefore, it is apparent to persons skilled in the art that the present disclosure as claimed may include variations of specific embodiments and preferred embodiments described herein. Many of the materials and structures described herein may be replaced with other materials and structures without departing from the spirit of the present disclosure. It should be understood that various theories as to why the present disclosure works are not intended to be limitative.

What is claimed is:

1. A compound, having a structure represented by Formula 1:

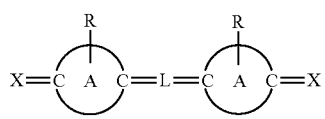

Formula 1 wherein
L is, at each occurrence identically or differently, selected from

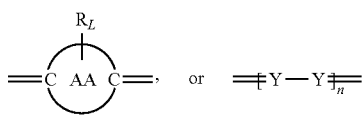

or any combination thereof;
ring AA is a conjugated structure having 4 to 30 ring atoms and at least one intra-ring double bond;
n is, at each occurrence identically or differently, selected from an integer from 0 to 10;
Y is, at each occurrence identically or differently, selected from the group consisting of $CR_L$ and N;
ring A is, at each occurrence identically or differently, a 5-membered heterocyclic ring, and the 5-membered heterocyclic ring comprises an intra-ring double bond, at least one N atom, and at least one W;

W is, at each occurrence identically or differently, selected from the group consisting of O, S, Se, and $NR_N$;

X is, at each occurrence identically or differently, selected from the group consisting of Se, NR', and CR"R'";

R and $R_L$ represent, at each occurrence identically or differently, mono-substitution, multiple substitutions or non-substitution;

R, R', R", R'", $R_L$, and $R_N$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

when L is selected from

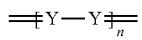

and n=0, at least one of substituents R and $R_N$ is a group having at least one electron-withdrawing group;

when X is selected from NR' or CR"R'", at least one of R', R" and R'" is a group having at least one electron-withdrawing group;

adjacent substituents R", R'" can be optionally joined to form a ring; and adjacent substituents R, $R_L$ can be optionally joined to form a ring; when adjacent substituents $R_L$ are joined to form a ring, the resulting ring has at least 4 ring atoms; and when adjacent substituents R are joined to form a ring, the resulting ring has at least 6 ring atoms.

2. The compound according to claim 1, wherein at least one of substituents R, $R_L$, and $R_N$ is a group having at least one electron-withdrawing group; preferably, at least one of R and $R_L$ is a group having at least one electron-withdrawing group.

3. The compound according to claim 1, wherein ring A in

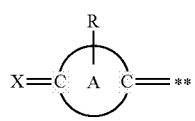

which is connected to both sides of L in Formula 1 contains CR, and R is a group having at least one electron-withdrawing group; preferably

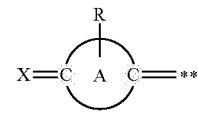

connected to both sides of L in Formula 1 is, at each occurrence identically or differently, selected from any one of the structures represented by Formula 2 to Formula 5:

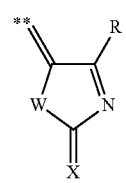

Formula 2

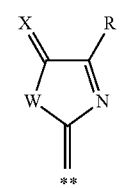

Formula 3

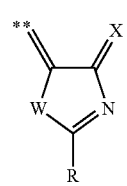

Formula 4

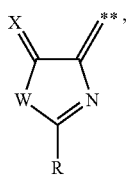

Formula 5 wherein in Formula 2 to Formula 5,

X, W, and R have the same definition as defined in claim 1; and

** represents a position where Formula 2 to Formula 5 are connected to L in Formula 1.

4. The compound according to claim 1, wherein L is, at each occurrence identically or differently, selected from structures represented by Formula 6 and Formula 6A and combinations thereof:

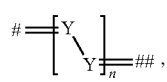

Formula 6

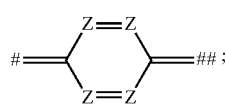

Formula 6A wherein in Formula 6 and Formula 6A, n is, at each occurrence identically or differently, selected from an integer from 0 to 10, Y and Z are, at each occurrence identically or differently, selected from $CR_L$ or N;

$R_L$ is, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

adjacent substituents $R_L$ can be optionally joined to form a ring; and # and ## represent positions where Formula 6 and Formula 6A are connected to ring A or L in Formula 1.

5. The compound according to claim 1, wherein L is

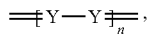

n is 0, and the compound has any one of the structures represented by Formula I to Formula XVI:

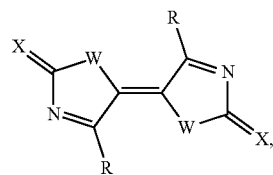

Formula I

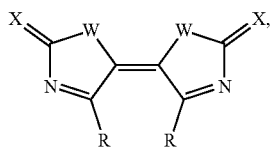

Formula II

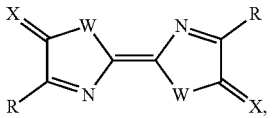

Formula III

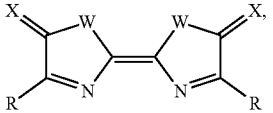

Formula IV

-continued

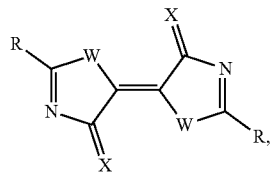

Formula V

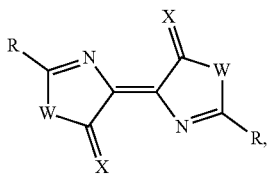

Formula VI

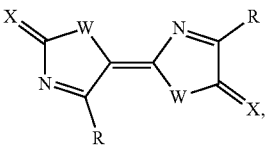

Formula VII

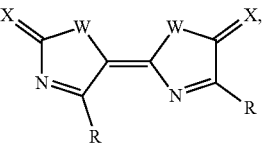

Formula VIII

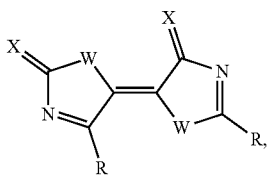

Formula IX

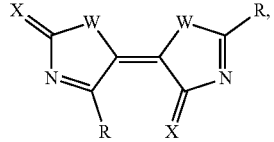

Formula X

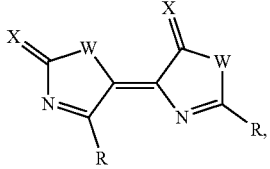

Formula XI

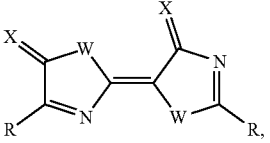

Formula XII

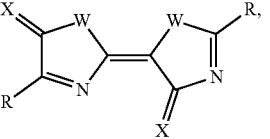

Formula XIII

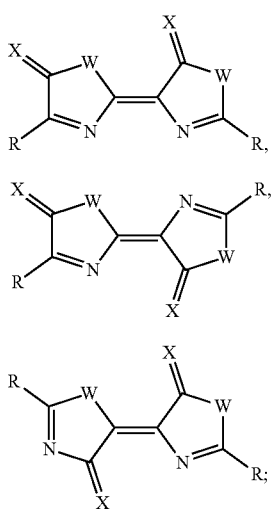

Formula XIV

Formula XV

Formula XVI wherein in Formula I to Formula XVI,
X, W, and R have the same definition as defined in claim 1; and
preferably, the compound has a structure represented by any one of Formula I, Formula II, Formula V, Formula IX, Formula X, Formula XI, and Formula XVI.

6. The compound according to claim 1, wherein the compound has any one of the structures represented by Formula I, Formula LIA and Formula II-I:

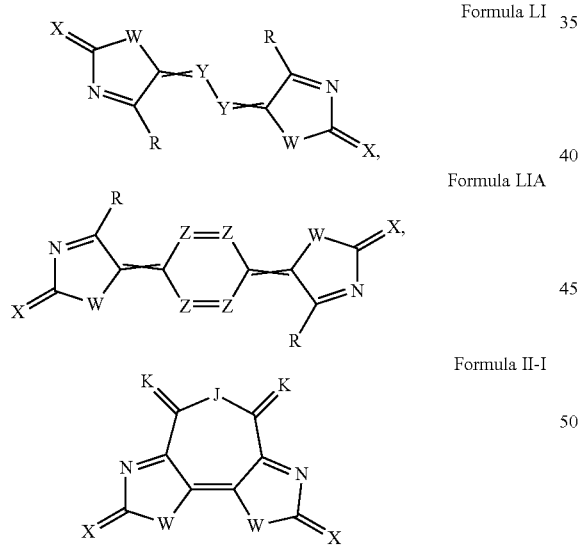

Formula LI

Formula LIA

Formula II-I wherein in Formula LI, Formula LIA and Formula II-I,
K is, at each occurrence identically or differently, selected from the group consisting of O, S, Se, and $CR_AR_B$;
J is, at each occurrence identically or differently, selected from the group consisting of O, S, Se, and $NR_{NJ}$; preferably, J is, at each occurrence identically or differently, selected from $NR_{NJ}$;
Y and Z are, at each occurrence identically or differently, selected from the group consisting of $CR_L$ and N;

X is, at each occurrence identically or differently, selected from the group consisting of Se, NR', and CR"R'";
W is, at each occurrence identically or differently, selected from the group consisting of O, S, Se, and $NR_N$;
$R_A$, $R_B$, R, R', R", R'", $R_L$, $R_N$ and $R_{NJ}$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;
when X is selected from NR' or CR"R'", at least one of R', R", and R'" is a group having at least one electron-withdrawing group;
in Formula II-I, at least one of substituents $R_A$, $R_B$, $R_N$, and $R_{NJ}$ is a group having at least one electron-withdrawing group, and/or at least one of K is O;
adjacent substituents R", R'" can be optionally joined to form a ring;
adjacent substituents $R_A$ and $R_B$ can be optionally joined to form a ring;
adjacent substituents R, $R_L$ can be optionally joined to form a ring; when adjacent substituents $R_L$ are joined to form a ring, the resulting ring has at least 4 ring atoms; and when adjacent substituents R are joined to form a ring, the resulting ring has at least 6 ring atoms; preferably, at least one of substituents R, $R_L$, and $R_N$ is a group having at least one electron-withdrawing group.

7. The compound according to claim 1, wherein Y is, at each occurrence identically or differently, selected from $CR_L$.

8. The compound according to claim 1, wherein X is, at each occurrence identically or differently, selected from CR"R'".

9. The compound according to claim 1, wherein W is, at each occurrence identically or differently, selected from O, S or Se; preferably, W is, at each occurrence identically or differently, selected from O or S; and more preferably, W is O.

10. The compound according to claim 1, wherein W is, at each occurrence identically or differently, selected from $NR_N$, and $R_N$ is, at each occurrence identically or differently, selected from the group consisting of: substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof; and preferably, $R_N$ is, at each occurrence identically or differently, selected from the group consisting of: substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, and combinations thereof.

11. The compound according to claim 1, wherein at least one of R is a group having at least one electron-withdrawing group;

preferably, R is, at each occurrence identically or differently, a group having at least one electron-withdrawing group.

12. The compound according to claim 6, wherein at least one of R is a group having at least one electron-withdrawing group; and wherein each of R', R", R''', $R_L$, $R_N$, and $R_{NJ}$ is a group having at least one electron-withdrawing group.

13. The compound according to claim 1, wherein at least one of R is selected from substituted or unsubstituted aryl having 6 to 30 carbon atoms, substituted or unsubstituted heteroaryl having 3 to 30 carbon atoms, or combinations thereof; and preferably, at least one of R is aryl which has 6 to 30 carbon atoms and is substituted with at least one electron-withdrawing group, heteroaryl which has 3 to 30 carbon atoms and is substituted with at least one electron-withdrawing group, or combinations thereof.

14. The compound according to claim 1, wherein R is, at each occurrence identically or differently, selected from substituted or unsubstituted aryl having 6 to 30 carbon atoms, substituted or unsubstituted heteroaryl having 3 to 30 carbon atoms, or combinations thereof; and preferably, R is, at each occurrence, aryl which has 6 to 30 carbon atoms and is substituted with at least one electron-withdrawing group, heteroaryl which has 3 to 30 carbon atoms and is substituted with at least one electron-withdrawing group, or combinations thereof.

15. The compound according to claim 1, wherein the Hammett constant of the electron-withdrawing group is greater than or equal to 0.05, preferably, is greater than or equal to 0.3, and more preferably, is greater than or equal to 0.5.

16. The compound according to claim 1, wherein the electron-withdrawing group is selected from the group consisting of: halogen, a nitroso group, a nitro group, an acyl group, a carbonyl group, a carboxylic acid group, an ester group, a cyano group, an isocyano group, SCN, OCN, SF$_5$, a boranyl group, a sulfinyl group, a sulfonyl group, a phosphoroso group, an aza-aromatic ring group, or any one of the following groups substituted by one or more of halogen, a nitroso group, a nitro group, an acyl group, a carbonyl group, a carboxylic acid group, an ester group, a cyano group, an isocyano group, SCN, OCN, SF$_5$, a boranyl group, a sulfinyl group, a sulfonyl group, a phosphoroso group, and an aza-aromatic ring group: alkyl having 1 to 20 carbon atoms, cycloalkyl having 3 to 20 ring carbon atoms, heteroalkyl having 1 to 20 carbon atoms, a heterocyclic group having 3 to 20 ring atoms, aralkyl having 7 to 30 carbon atoms, alkoxy having 1 to 20 carbon atoms, aryloxy having 6 to 30 carbon atoms, alkenyl having 2 to 20 carbon atoms, alkynyl having 2 to 20 carbon atoms, aryl having 6 to 30 carbon atoms, heteroaryl having 3 to 30 carbon atoms, alkylsilyl having 3 to 20 carbon atoms, arylsilyl having 6 to 20 carbon atoms, and combinations thereof; and preferably, the electron-withdrawing group is selected from the group consisting of: F, CF$_3$, CHF$_2$, OCF$_3$, SF$_5$, SO$_2$CF$_3$, a cyano group, an isocyano group, SCN, OCN, a pyrimidinyl group, a triazinyl group, and combinations thereof.

17. The compound according to claim 1, wherein X is, at each occurrence identically or differently, selected from the group consisting of the following structures:

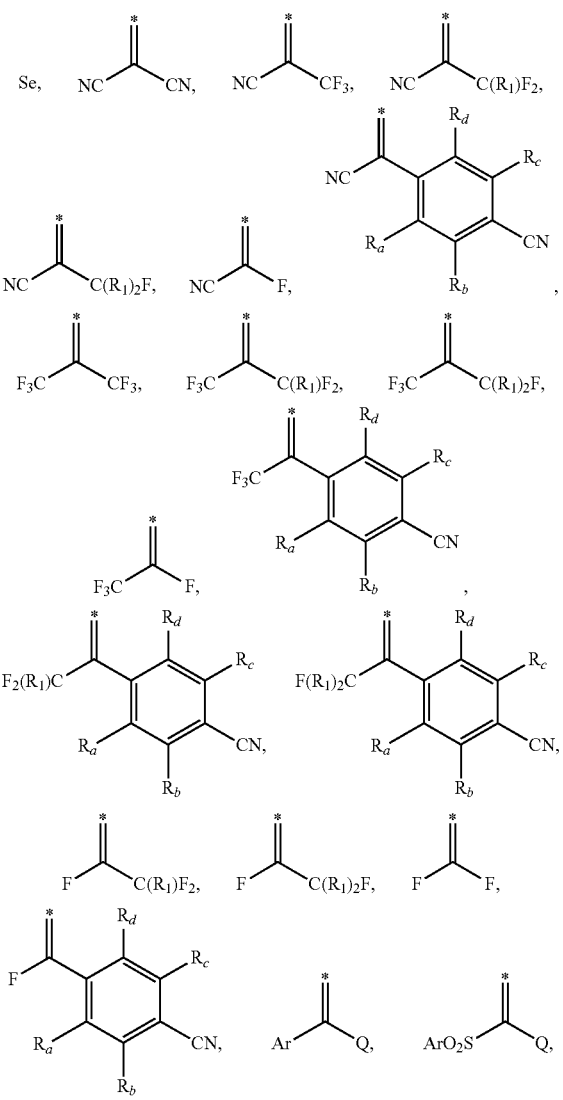

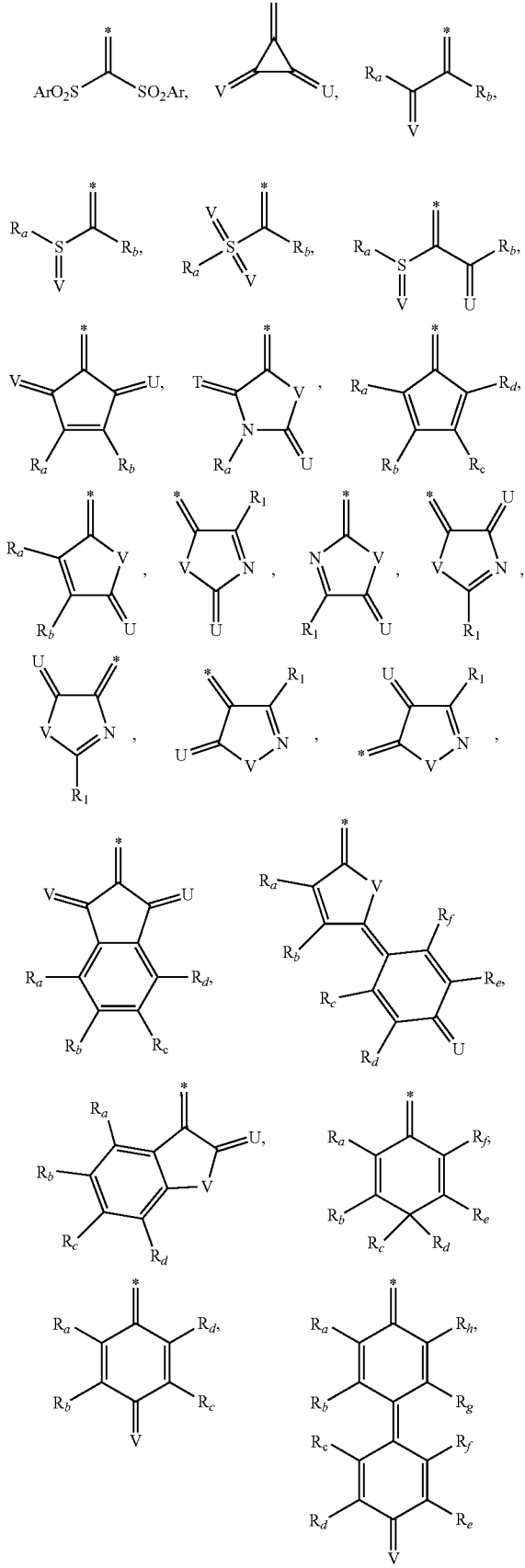
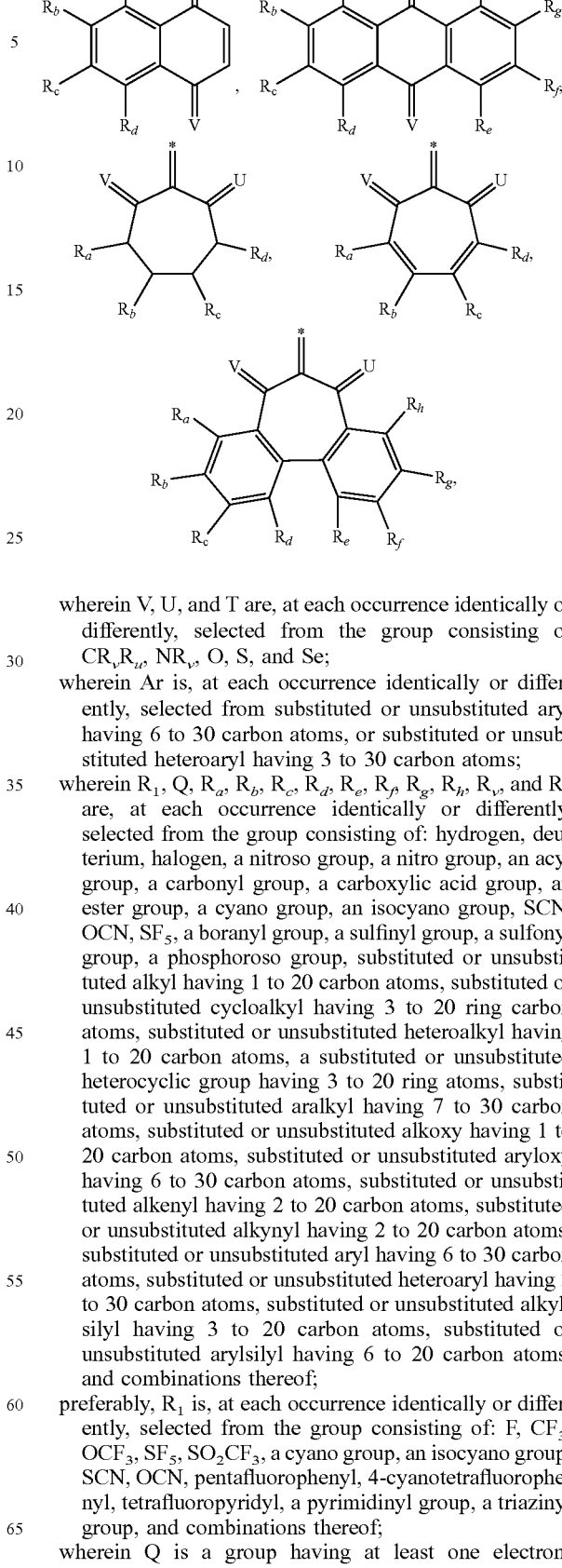

wherein V, U, and T are, at each occurrence identically or differently, selected from the group consisting of $CR_vR_u$, $NR_v$, O, S, and Se;

wherein Ar is, at each occurrence identically or differently, selected from substituted or unsubstituted aryl having 6 to 30 carbon atoms, or substituted or unsubstituted heteroaryl having 3 to 30 carbon atoms;

wherein $R_1$, Q, $R_a$, $R_b$, $R_c$, $R_d$, $R_e$, $R_f$, $R_g$, $R_h$, $R_v$, and $R_u$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof;

preferably, $R_1$ is, at each occurrence identically or differently, selected from the group consisting of: F, $CF_3$, $OCF_3$, $SF_5$, $SO_2CF_3$, a cyano group, an isocyano group, SCN, OCN, pentafluorophenyl, 4-cyanotetrafluorophenyl, tetrafluoropyridyl, a pyrimidinyl group, a triazinyl group, and combinations thereof;

wherein Q is a group having at least one electron-withdrawing group, and for any one of the preceding structures, when one or more of $R_a$, $R_b$, $R_c$, $R_d$, $R_e$, $R_f$, $R_g$, $R_h$, $R_v$, and $R_u$ occur, at least one of $R_a$, $R_b$, $R_c$, $R_d$, $R_e$, $R_f$, $R_g$, $R_h$, $R_v$, and $R_u$ is a group having at least one electron-withdrawing group; preferably, the group having at least one electron-withdrawing group is selected from the group consisting of: F, $CF_3$, $OCF_3$, $SF_5$, $SO_2CF_3$, a cyano group, an isocyano group, SCN, OCN, pentafluorophenyl, 4-cyanotetrafluorophenyl, tetrafluoropyridyl, a pyrimidinyl group, a triazinyl group, and combinations thereof;

adjacent substituents $R_1$, $R_a$, $R_b$, $R_c$, $R_d$, $R_e$, $R_f$, $R_g$, $R_h$, $R_v$, and $R_u$ can be optionally joined to form a ring; and

* represents a position where X having the preceding structures is connected to ring A in Formula 1;

preferably, X is, at each occurrence identically or differently, selected from the group consisting of the following structures:

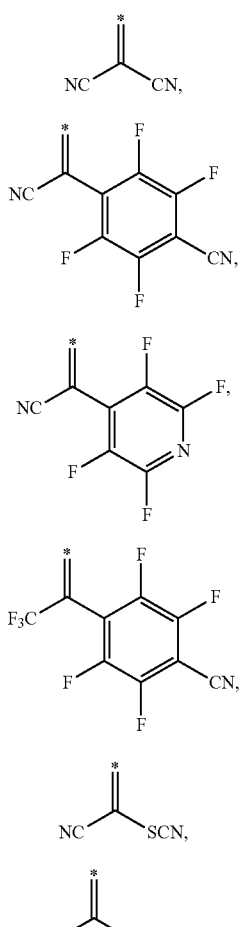

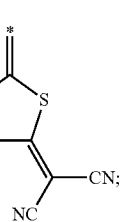

more preferably, X is selected from

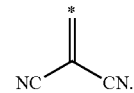

18. The compound according to claim 6, wherein R, $R_L$, $R_N$, and $R_{NJ}$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof; and preferably, R, $R_L$, $R_N$, and $R_{NJ}$ are, at each occurrence identically or differently, selected from the group consisting of: hydrogen, deuterium, a methyl group, an isopropyl group, $NO_2$, $SO_2CH_3$, $SCF_3$, $C_2F_5$, $OC_2F_5$, diphenylmethylsilyl, a phenyl group, methoxyphenyl, p-methylphenyl, 2,6-diisopropylphenyl, a biphenylyl group, polyfluorophenyl, difluopyridyl, nitrophenyl, dimethylthiazolyl, CN, a vinyl group substituted by one or more of CN or $CF_3$, an acetenyl group substituted by one of CN or $CF_3$, dimethylphosphoryl, diphenylphosphoryl, F, $CF_3$, $OCF_3$, $SF_5$, $SO_2CF_3$, a cyano group, an isocyano group, SCN, OCN, trifluoromethylphenyl, trifluoromethoxyphenyl, bis(trifluoromethyl)phenyl, bis(trifluoromethoxy)phenyl, 4-cyanotetrafluorophenyl, a phenyl or biphenylyl group substituted by one or more of F, CN or $CF_3$, tetrafluoropyridyl, a pyrimidinyl group, a triazinyl group, a pyridyl group, diphenylboryl, phenoxaborin, and combinations thereof.

19. The compound according to claim 1, wherein R, $R_L$, $R_N$, and $R_{NJ}$ are, at each occurrence identically or differently, selected from the group consisting of the following structures:

-continued
B3 
B4 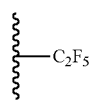
B5 
B6 
B7 
B8 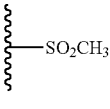
B9 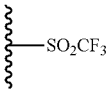
B10 
B11 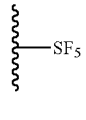
B12 
B13 
B14 
B15 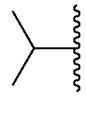
B16 
-continued
B17 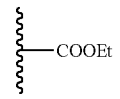
B18 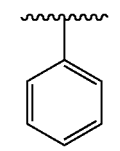
B19 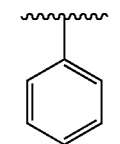
B20 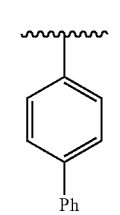
B21 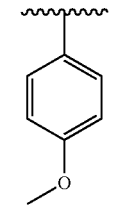
B22 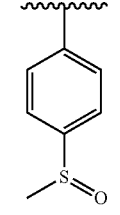
B23 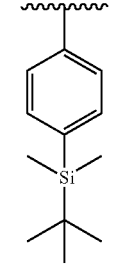
B24 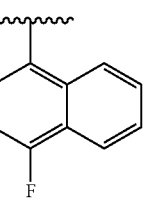

-continued
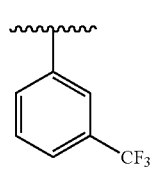 B25
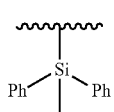 B26
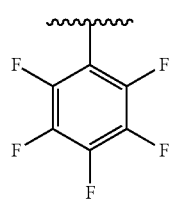 B27
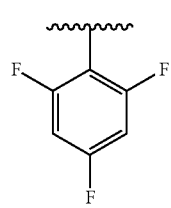 B28
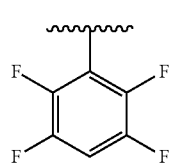 B29
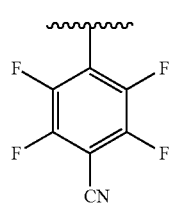 B30
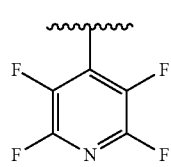 B31
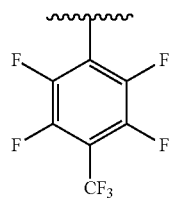 B32
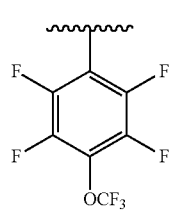 B33
-continued
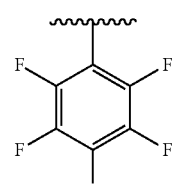 B34
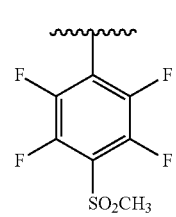 B35
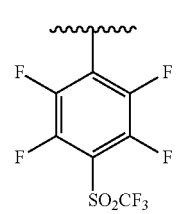 B36
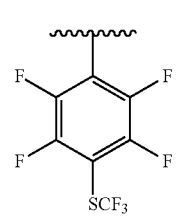 B37
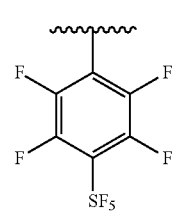 B38
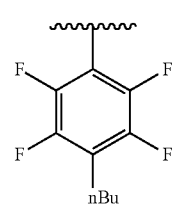 B39
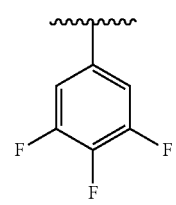 B40
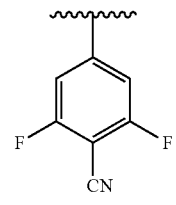 B41

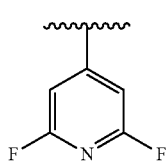 B42
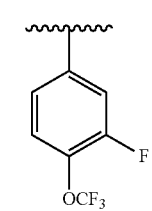
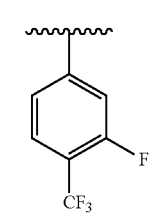
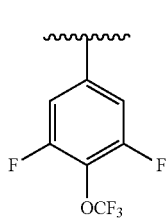 B43
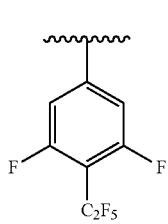 B44
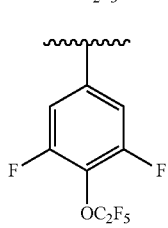 B45
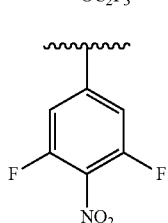 B46
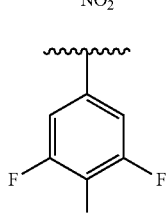 B47
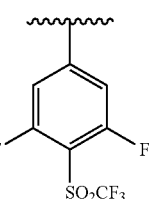 B48
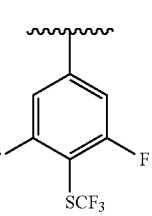 B49
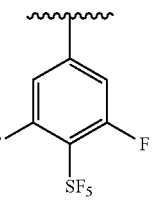 B50
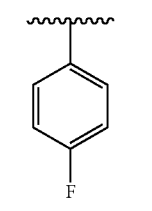 B51
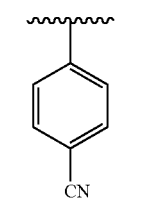 B52
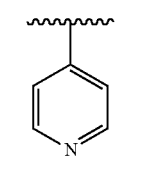 B53
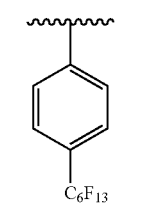 B54
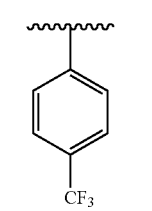 B55
B56
B57

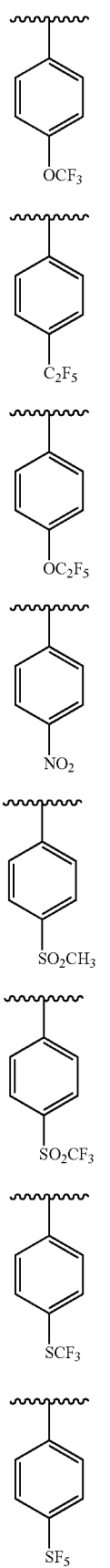
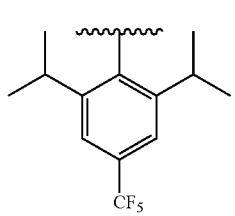 B66
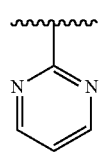 B67
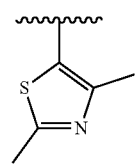 B68
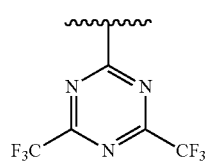 B69
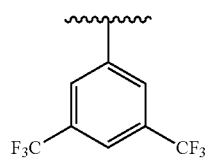 B70
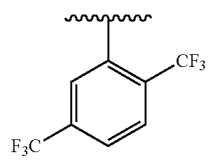 B71
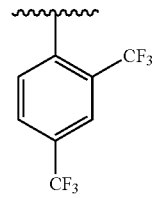 B72
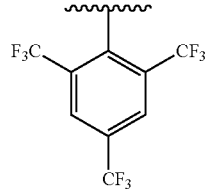 B73

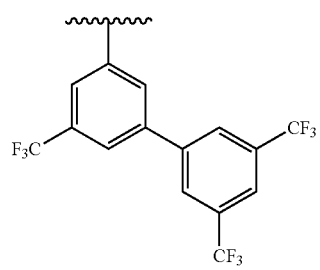 B74
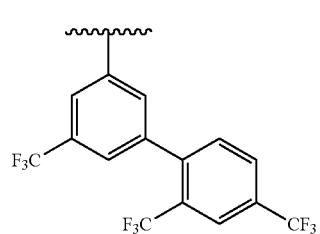 B75
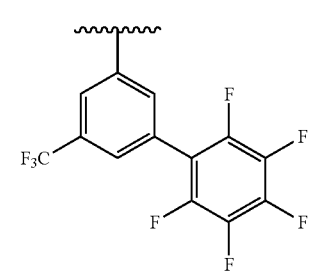 B76
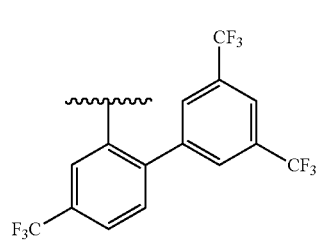 B77
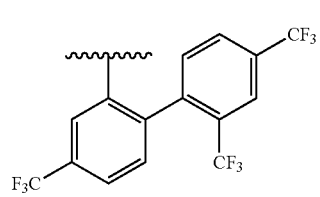 B78
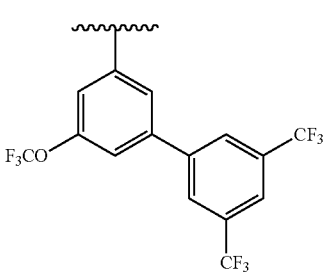 B79
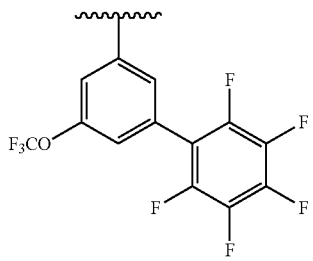 B80
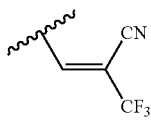 B81
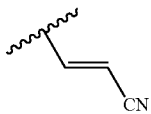 B82
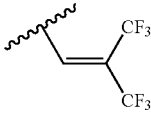 B83
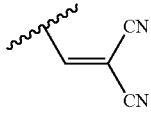 B84
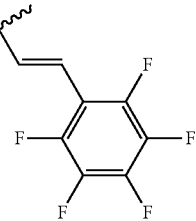 B85
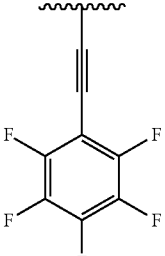 B86
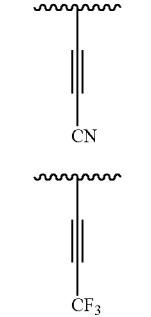 B87
B88

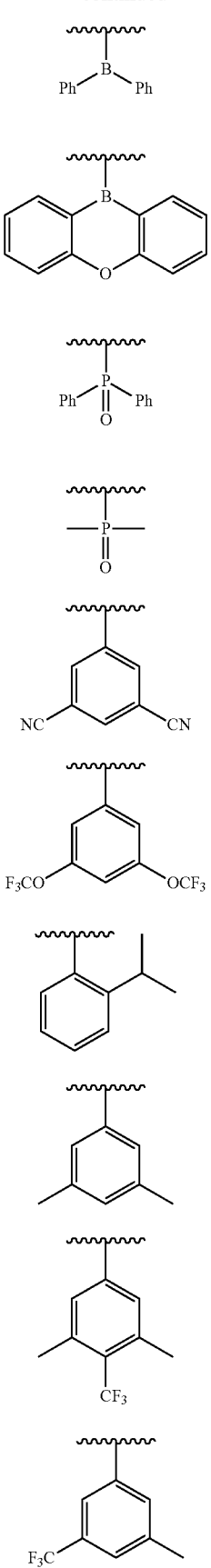

-continued
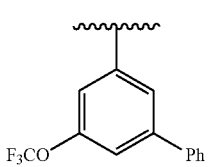
B107
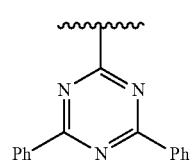
B108
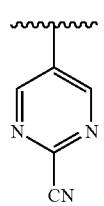
B109
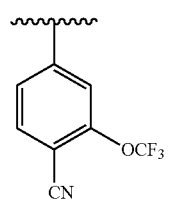
B110
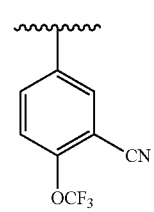
B111
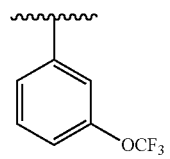
B112
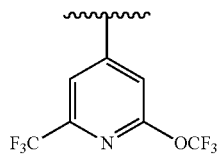
B113
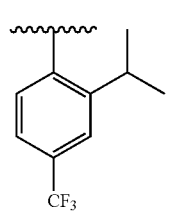
B114
-continued
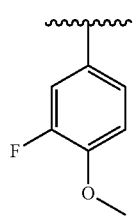
B115
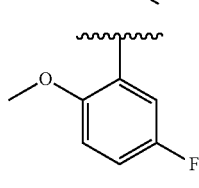
B116
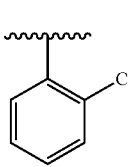
B117
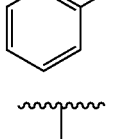
B119
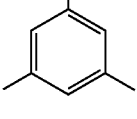
B120
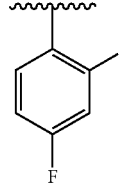
B121
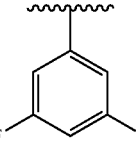
B122
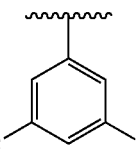
B123
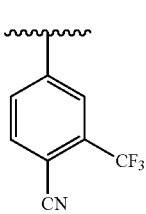
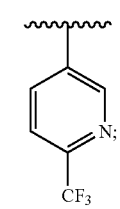
B124 preferably, R, $R_L$, $R_N$, and $R_{NJ}$ are, at each occurrence identically or differently, selected from the group consisting of:
B6
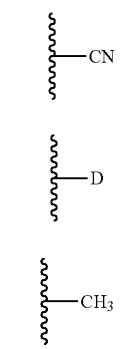
B13
B14
B16
B17
B18
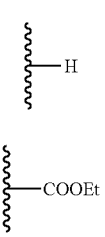
B25
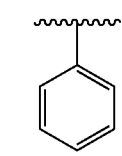
B27
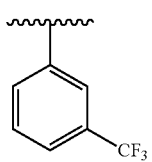
B28
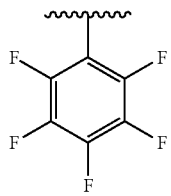
B30
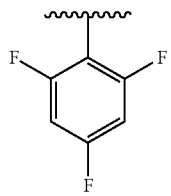
-continued
B31
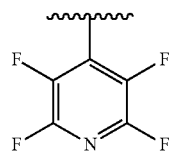
B40
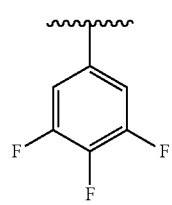
B41
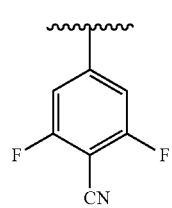
B42
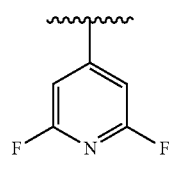
B44
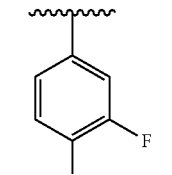
B53
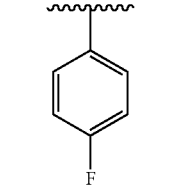
B54
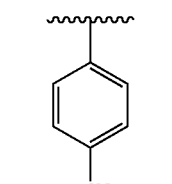
B55
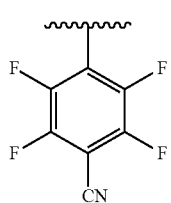

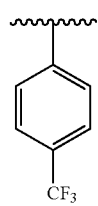 B57
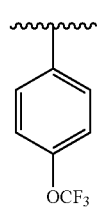 B58
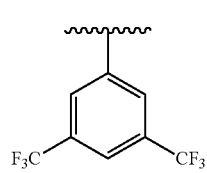 B70
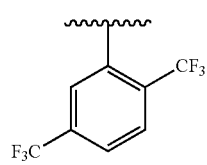 B71
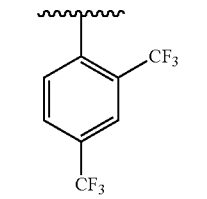 B72
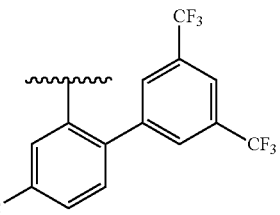 B77
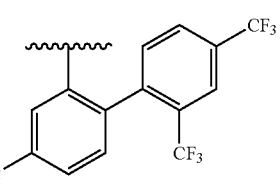 B78
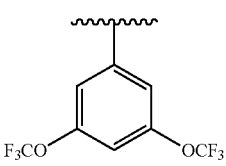 B94
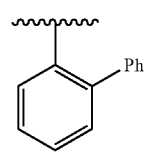 B103
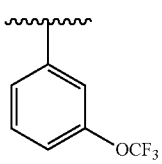 B112
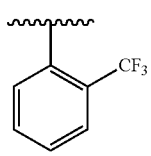 B117
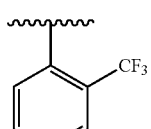 B118
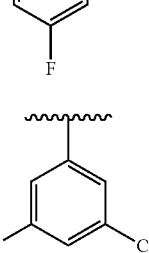 B119
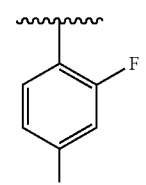 B120
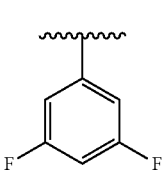 B121
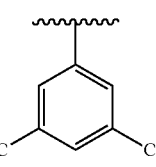 B122
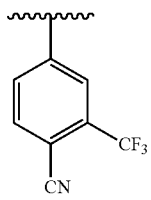 B123

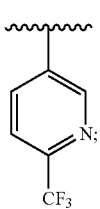

B124 wherein ⁓ represents a position where R having the preceding structures is connected to Formula 1 and a position where $R_L$ having the preceding structures is connected to L; ⁓ further represents a position where $R_{NJ}$ is connected to N when J is selected from $NR_{NJ}$; and ⁓ further represents a position where $R_N$ is connected to N when W is selected from $NR_N$.

20. The compound according to claim 1, wherein the compound is selected from the group consisting of: Compound I-1 to Compound I-114, Compound II-1 to Compound II-108, Compound III-1 to Compound III-108, Compound IV-1 to Compound IV-108, Compound V-1 to Compound V-108, Compound VI-1 to Compound VI-108, Compound VII-1 to Compound VII-108, Compound VIII-1 to Compound VIII-108, Compound IX-1 to Compound IX-108, Compound X-1 to Compound X-108, Compound XI-1 to Compound XI-108, Compound XII-1 to Compound XII-108, Compound XIII-1 to Compound XIII-108, Compound XIV-1 to Compound XIV-108, Compound XV-1 to Compound XV-108, and Compound XVI-1 to Compound XVI-108, Compound LIO-1 to Compound LIO-108, and Compound LIOA-1 to Compound LIOA-66, Compound II-IO-1 to Compound II-IO-60;

wherein Compound I-1 to Compound I-114 have a structure represented by Formula I:

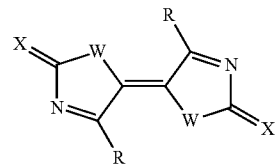

Formula I in Formula I, two X are identical, two W are identical, two R are identical, and X, W, and R correspond to an atom or a group selected from the following table, respectively:

| No. | X | W | R | No | X | W | R | No | X | W | R |
|---|---|---|---|---|---|---|---|---|---|---|---|
| I-1 | A1 | O | B1 | I-2 | A1 | O | B17 | I-3 | A1 | O | B27 |
| I-4 | A1 | O | B30 | I-5 | A1 | O | B54 | I-6 | A1 | O | B57 |
| I-7 | A1 | O | B58 | I-8 | A1 | O | B70 | I-9 | A1 | O | B71 |
| I-10 | A1 | O | B72 | I-11 | A1 | O | B117 | I-12 | A1 | O | B122 |
| I-13 | A1 | S | B1 | I-14 | A1 | S | B17 | I-15 | A1 | S | B27 |
| I-16 | A1 | S | B30 | I-17 | A1 | S | B54 | I-18 | A1 | S | B57 |
| I-19 | A1 | S | B58 | I-20 | A1 | S | B70 | I-21 | A1 | S | B71 |
| I-22 | A1 | S | B72 | I-23 | A1 | S | B117 | I-24 | A1 | S | B122 |
| I-25 | A1 | Se | B1 | I-26 | A1 | Se | B17 | I-27 | A1 | Se | B27 |
| I-28 | A1 | Se | B30 | I-29 | A1 | Se | B54 | I-30 | A1 | Se | B57 |
| I-31 | A1 | Se | B58 | I-32 | A1 | Se | B70 | I-33 | A1 | Se | B71 |
| I-34 | A1 | Se | B72 | I-35 | A1 | Se | B117 | I-36 | A1 | Se | B122 |
| I-37 | A1 | NMe | B1 | I-38 | A1 | NMe | B17 | I-39 | A1 | NMe | B27 |
| I-40 | A1 | NMe | B30 | I-41 | A1 | NMe | B54 | I-42 | A1 | NMe | B57 |
| I-43 | A1 | NMe | B58 | I-44 | A1 | NMe | B70 | I-45 | A1 | NMe | B71 |
| I-46 | A1 | NMe | B72 | I-47 | A1 | NMe | B117 | I-48 | A1 | NMe | B122 |
| I-49 | A2 | O | B1 | I-50 | A2 | O | B17 | I-51 | A2 | O | B27 |
| I-52 | A2 | O | B30 | I-53 | A2 | O | B54 | I-54 | A2 | O | B57 |
| I-55 | A2 | O | B58 | I-56 | A2 | O | B70 | I-57 | A2 | O | B71 |
| I-58 | A2 | O | B72 | I-59 | A2 | O | B117 | I-60 | A2 | O | B122 |
| I-61 | A2 | S | B1 | I-62 | A2 | S | B17 | I-63 | A2 | S | B27 |
| I-64 | A2 | S | B30 | I-65 | A2 | S | B54 | I-66 | A2 | S | B57 |
| I-67 | A2 | S | B58 | I-68 | A2 | S | B70 | I-69 | A2 | S | B71 |
| I-70 | A2 | S | B72 | I-71 | A2 | S | B117 | I-72 | A2 | S | B122 |
| I-73 | A2 | Se | B1 | I-74 | A2 | Se | B17 | I-75 | A2 | Se | B27 |
| I-76 | A2 | Se | B30 | I-77 | A2 | Se | B54 | I-78 | A2 | Se | B57 |
| I-79 | A2 | Se | B58 | I-80 | A2 | Se | B70 | I-81 | A2 | Se | B71 |
| I-82 | A2 | Se | B72 | I-83 | A2 | Se | B117 | I-84 | A2 | Se | B122 |
| I-85 | A3 | O | B1 | I-86 | A3 | O | B17 | I-87 | A3 | O | B27 |
| I-88 | A3 | O | B30 | I-89 | A3 | O | B54 | I-90 | A3 | O | B57 |
| I-91 | A3 | O | B58 | I-92 | A3 | O | B70 | I-93 | A3 | O | B71 |
| I-94 | A3 | O | B72 | I-95 | A3 | O | B117 | I-96 | A3 | O | B122 |
| I-97 | A3 | S | B1 | I-98 | A3 | S | B17 | I-99 | A3 | S | B27 |
| I-100 | A3 | S | B30 | I-101 | A3 | S | B54 | I-102 | A3 | S | B57 |
| I-103 | A3 | S | B58 | I-104 | A3 | S | B70 | I-105 | A3 | S | B71 |
| I-106 | A3 | S | B72 | I-107 | A3 | S | B117 | I-108 | A3 | S | B122 |
| I-109 | A1 | O | B31 | I-110 | A1 | O | B123 | I-111 | A1 | O | B124 |
| I-112 | A1 | O | B32 | I-113 | A1 | O | B33 | I-114 | A1 | O | B113 | wherein Compound II-1 to Compound II-108 have a structure represented by Formula II:

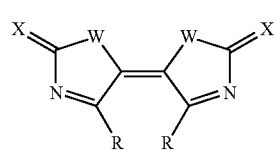

Formula II in Formula II, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| II-1 | A1 | O | B1 | II-2 | A1 | O | B17 | II-3 | A1 | O | B27 |
| II-4 | A1 | O | B30 | II-5 | A1 | O | B54 | II-6 | A1 | O | B57 |
| II-7 | A1 | O | B58 | II-8 | A1 | O | B70 | II-9 | A1 | O | B71 |
| II-10 | A1 | O | B72 | II-11 | A1 | O | B117 | II-12 | A1 | O | B122 |
| II-13 | A1 | S | B1 | II-14 | A1 | S | B17 | II-15 | A1 | S | B27 |
| II-16 | A1 | S | B30 | II-17 | A1 | S | B54 | II-18 | A1 | S | B57 |
| II-19 | A1 | S | B58 | II-20 | A1 | S | B70 | II-21 | A1 | S | B71 |
| II-22 | A1 | S | B72 | II-23 | A1 | S | B117 | II-24 | A1 | S | B122 |
| II-25 | A1 | Se | B1 | II-26 | A1 | Se | B17 | II-27 | A1 | Se | B27 |
| II-28 | A1 | Se | B30 | II-29 | A1 | Se | B54 | II-30 | A1 | Se | B57 |
| II-31 | A1 | Se | B58 | II-32 | A1 | Se | B70 | II-33 | A1 | Se | B71 |
| II-34 | A1 | Se | B72 | II-35 | A1 | Se | B117 | II-36 | A1 | Se | B122 |
| II-37 | A1 | NMe | B1 | II-38 | A1 | NMe | B17 | II-39 | A1 | NMe | B27 |
| II-40 | A1 | NMe | B30 | II-41 | A1 | NMe | B54 | II-42 | A1 | NMe | B57 |
| II-43 | A1 | NMe | B58 | II-44 | A1 | NMe | B70 | II-45 | A1 | NMe | B71 |
| II-46 | A1 | NMe | B72 | II-47 | A1 | NMe | B117 | II-48 | A1 | NMe | B122 |
| II-49 | A2 | O | B1 | II-50 | A2 | O | B17 | II-51 | A2 | O | B27 |
| II-52 | A2 | O | B30 | II-53 | A2 | O | B54 | II-54 | A2 | O | B57 |
| II-55 | A2 | O | B58 | II-56 | A2 | O | B70 | II-57 | A2 | O | B71 |
| II-58 | A2 | O | B72 | II-59 | A2 | O | B117 | II-60 | A2 | O | B122 |
| II-61 | A2 | S | B1 | II-62 | A2 | S | B17 | II-63 | A2 | S | B27 |
| II-64 | A2 | S | B30 | II-65 | A2 | S | B54 | II-66 | A2 | S | B57 |
| II-67 | A2 | S | B58 | II-68 | A2 | S | B70 | II-69 | A2 | S | B71 |
| II-70 | A2 | S | B72 | II-71 | A2 | S | B117 | II-72 | A2 | S | B122 |
| II-73 | A2 | Se | B1 | II-74 | A2 | Se | B17 | II-75 | A2 | Se | B27 |
| II-76 | A2 | Se | B30 | II-77 | A2 | Se | B54 | II-78 | A2 | Se | B57 |
| II-79 | A2 | Se | B58 | II-80 | A2 | Se | B70 | II-81 | A2 | Se | B71 |
| II-82 | A2 | Se | B72 | II-83 | A2 | Se | B117 | II-84 | A2 | Se | B122 |
| II-85 | A3 | O | B1 | II-86 | A3 | O | B17 | II-87 | A3 | O | B27 |
| II-88 | A3 | O | B30 | II-89 | A3 | O | B54 | II-90 | A3 | O | B57 |
| II-91 | A3 | O | B58 | II-92 | A3 | O | B70 | II-93 | A3 | O | B71 |
| II-94 | A3 | O | B72 | II-95 | A3 | O | B117 | II-96 | A3 | O | B122 |
| II-97 | A3 | S | B1 | II-98 | A3 | S | B17 | II-99 | A3 | S | B27 |
| II-100 | A3 | S | B30 | II-101 | A3 | S | B54 | II-102 | A3 | S | B57 |
| II-103 | A3 | S | B58 | II-104 | A3 | S | B70 | II-105 | A3 | S | B71 |
| II-106 | A3 | S | B72 | II-107 | A3 | S | B117 | II-108 | A3 | S | B122 | wherein Compound III-1 to Compound III-108 have a structure represented by Formula III:

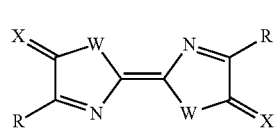

Formula III in Formula III, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| III-1 | A1 | O | B1 | III-2 | A1 | O | B17 | III-3 | A1 | O | B27 |
| III-4 | A1 | O | B30 | III-5 | A1 | O | B54 | III-6 | A1 | O | B57 |
| III-7 | A1 | O | B58 | III-8 | A1 | O | B70 | III-9 | A1 | O | B71 |
| III-10 | A1 | O | B72 | III-11 | A1 | O | B117 | III-12 | A1 | O | B122 |
| III-13 | A1 | S | B1 | III-14 | A1 | S | B17 | III-15 | A1 | S | B27 |
| III-16 | A1 | S | B30 | III-17 | A1 | S | B54 | III-18 | A1 | S | B57 |
| III-19 | A1 | S | B58 | III-20 | A1 | S | B70 | III-21 | A1 | S | B71 |
| III-22 | A1 | S | B72 | III-23 | A1 | S | B117 | III-24 | A1 | S | B122 |
| III-25 | A1 | Se | B1 | III-26 | A1 | Se | B17 | III-27 | A1 | Se | B27 |
| III-28 | A1 | Se | B30 | III-29 | A1 | Se | B54 | III-30 | A1 | Se | B57 |
| III-31 | A1 | Se | B58 | III-32 | A1 | Se | B70 | III-33 | A1 | Se | B71 |
| III-34 | A1 | Se | B72 | III-35 | A1 | Se | B117 | III-36 | A1 | Se | B122 |
| III-37 | A1 | NMe | B1 | III-38 | A1 | NMe | B17 | III-39 | A1 | NMe | B27 |
| III-40 | A1 | NMe | B30 | III-41 | A1 | NMe | B54 | III-42 | A1 | NMe | B57 |
| III-43 | A1 | NMe | B58 | III-44 | A1 | NMe | B70 | III-45 | A1 | NMe | B71 |
| III-46 | A1 | NMe | B72 | III-47 | A1 | NMe | B117 | III-48 | A1 | NMe | B122 |
| III-49 | A2 | O | B1 | III-50 | A2 | O | B17 | III-51 | A2 | O | B27 |
| III-52 | A2 | O | B30 | III-53 | A2 | O | B54 | III-54 | A2 | O | B57 |
| III-55 | A2 | O | B58 | III-56 | A2 | O | B70 | III-57 | A2 | O | B71 |
| III-58 | A2 | O | B72 | III-59 | A2 | O | B117 | III-60 | A2 | O | B122 |
| III-61 | A2 | S | B1 | III-62 | A2 | S | B17 | III-63 | A2 | S | B27 |
| III-64 | A2 | S | B30 | III-65 | A2 | S | B54 | III-66 | A2 | S | B57 |
| III-67 | A2 | S | B58 | III-68 | A2 | S | B70 | III-69 | A2 | S | B71 |
| III-70 | A2 | S | B72 | III-71 | A2 | S | B117 | III-72 | A2 | S | B122 |
| III-73 | A2 | Se | B1 | III-74 | A2 | Se | B17 | III-75 | A2 | Se | B27 |
| III-76 | A2 | Se | B30 | III-77 | A2 | Se | B54 | III-78 | A2 | Se | B57 |
| III-79 | A2 | Se | B58 | III-80 | A2 | Se | B70 | III-81 | A2 | Se | B71 |
| III-82 | A2 | Se | B72 | III-83 | A2 | Se | B117 | III-84 | A2 | Se | B122 |
| III-85 | A3 | O | B1 | III-86 | A3 | O | B17 | III-87 | A3 | O | B27 |
| III-88 | A3 | O | B30 | III-89 | A3 | O | B54 | III-90 | A3 | O | B57 |
| III-91 | A3 | O | B58 | III-92 | A3 | O | B70 | III-93 | A3 | O | B71 |
| III-94 | A3 | O | B72 | III-95 | A3 | O | B117 | III-96 | A3 | O | B122 |
| III-97 | A3 | S | B1 | III-98 | A3 | S | B17 | III-99 | A3 | S | B27 |
| III-100 | A3 | S | B30 | III-101 | A3 | S | B54 | III-102 | A3 | S | B57 |
| III-103 | A3 | S | B58 | III-104 | A3 | S | B70 | III-105 | A3 | S | B71 |
| III-106 | A3 | S | B72 | III-107 | A3 | S | B117 | III-108 | A3 | S | B122 | wherein Compound IV-1 to Compound IV-108 have a structure represented by Formula IV:

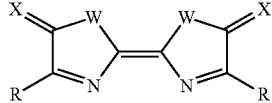

Formula IV in Formula IV, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| IV-1 | A1 | O | B1 | IV-2 | A1 | O | B17 | IV-3 | A1 | O | B27 |
| IV-4 | A1 | O | B30 | IV-5 | A1 | O | B54 | IV-6 | A1 | O | B57 |
| IV-7 | A1 | O | B58 | IV-8 | A1 | O | B70 | IV-9 | A1 | O | B71 |
| IV-10 | A1 | O | B72 | IV-11 | A1 | O | B117 | IV-12 | A1 | O | B122 |
| IV-13 | A1 | S | B1 | IV-14 | A1 | S | B17 | IV-15 | A1 | S | B27 |
| IV-16 | A1 | S | B30 | IV-17 | A1 | S | B54 | IV-18 | A1 | S | B57 |
| IV-19 | A1 | S | B58 | IV-20 | A1 | S | B70 | IV-21 | A1 | S | B71 |
| IV-22 | A1 | S | B72 | IV-23 | A1 | S | B117 | IV-24 | A1 | S | B122 |
| IV-25 | A1 | Se | B1 | IV-26 | A1 | Se | B17 | IV-27 | A1 | Se | B27 |
| IV-28 | A1 | Se | B30 | IV-29 | A1 | Se | B54 | IV-30 | A1 | Se | B57 |
| IV-31 | A1 | Se | B58 | IV-32 | A1 | Se | B70 | IV-33 | A1 | Se | B71 |
| IV-34 | A1 | Se | B72 | IV-35 | A1 | Se | B117 | IV-36 | A1 | Se | B122 |
| IV-37 | A1 | NMe | B1 | IV-38 | A1 | NMe | B17 | IV-39 | A1 | NMe | B27 |
| IV-40 | A1 | NMe | B30 | IV-41 | A1 | NMe | B54 | IV-42 | A1 | NMe | B57 |
| IV-43 | A1 | NMe | B58 | IV-44 | A1 | NMe | B70 | IV-45 | A1 | NMe | B71 |
| IV-46 | A1 | NMe | B72 | IV-47 | A1 | NMe | B117 | IV-48 | A1 | NMe | B122 |
| IV-49 | A2 | O | B1 | IV-50 | A2 | O | B17 | IV-51 | A2 | O | B27 |
| IV-52 | A2 | O | B30 | IV-53 | A2 | O | B54 | IV-54 | A2 | O | B57 |

-continued

| No. | X | W | R | No. | X | W | R | No. | X | W | R |
|---|---|---|---|---|---|---|---|---|---|---|---|
| IV-55 | A2 | O | B58 | IV-56 | A2 | O | B70 | IV-57 | A2 | O | B71 |
| IV-58 | A2 | O | B72 | IV-59 | A2 | O | B117 | IV-60 | A2 | O | B122 |
| IV-61 | A2 | S | B1 | IV-62 | A2 | S | B17 | IV-63 | A2 | S | B27 |
| IV-64 | A2 | S | B30 | IV-65 | A2 | S | B54 | IV-66 | A2 | S | B57 |
| IV-67 | A2 | S | B58 | IV-68 | A2 | S | B70 | IV-69 | A2 | S | B71 |
| IV-70 | A2 | S | B72 | IV-71 | A2 | S | B117 | IV-72 | A2 | S | B122 |
| IV-73 | A2 | Se | B1 | IV-74 | A2 | Se | B17 | IV-75 | A2 | Se | B27 |
| IV-76 | A2 | Se | B30 | IV-77 | A2 | Se | B54 | IV-78 | A2 | Se | B57 |
| IV-79 | A2 | Se | B58 | IV-80 | A2 | Se | B70 | IV-81 | A2 | Se | B71 |
| IV-82 | A2 | Se | B72 | IV-83 | A2 | Se | B117 | IV-84 | A2 | Se | B122 |
| IV-85 | A3 | O | B1 | IV-86 | A3 | O | B17 | IV-87 | A3 | O | B27 |
| IV-88 | A3 | O | B30 | IV-89 | A3 | O | B54 | IV-90 | A3 | O | B57 |
| IV-91 | A3 | O | B58 | IV-92 | A3 | O | B70 | IV-93 | A3 | O | B71 |
| IV-94 | A3 | O | B72 | IV-95 | A3 | O | B117 | IV-96 | A3 | O | B122 |
| IV-97 | A3 | S | B1 | IV-98 | A3 | S | B17 | IV-99 | A3 | S | B27 |
| IV-100 | A3 | S | B30 | IV-101 | A3 | S | B54 | IV-102 | A3 | S | B57 |
| IV-103 | A3 | S | B58 | IV-104 | A3 | S | B70 | IV-105 | A3 | S | B71 |
| IV-106 | A3 | S | B72 | IV-107 | A3 | S | B117 | IV-108 | A3 | S | B122 | wherein Compound V-1 to Compound V-108 have a structure represented by Formula V:

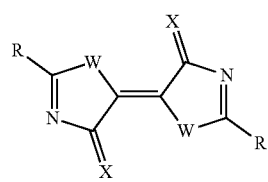

Formula V in Formula V, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| V-1 | A1 | O | B1 | V-2 | A1 | O | B17 | V-3 | A1 | O | B27 |
| V-4 | A1 | O | B30 | V-5 | A1 | O | B54 | V-6 | A1 | O | B57 |
| V-7 | A1 | O | B58 | V-8 | A1 | O | B70 | V-9 | A1 | O | B71 |
| V-10 | A1 | O | B72 | V-11 | A1 | O | B117 | V-12 | A1 | O | B122 |
| V-13 | A1 | S | B1 | V-14 | A1 | S | B17 | V-15 | A1 | S | B27 |
| V-16 | A1 | S | B30 | V-17 | A1 | S | B54 | V-18 | A1 | S | B57 |
| V-19 | A1 | S | B58 | V-20 | A1 | S | B70 | V-21 | A1 | S | B71 |
| V-22 | A1 | S | B72 | V-23 | A1 | S | B117 | V-24 | A1 | S | B122 |
| V-25 | A1 | Se | B1 | V-26 | A1 | Se | B17 | V-27 | A1 | Se | B27 |
| V-28 | A1 | Se | B30 | V-29 | A1 | Se | B54 | V-30 | A1 | Se | B57 |
| V-31 | A1 | Se | B58 | V-32 | A1 | Se | B70 | V-33 | A1 | Se | B71 |
| V-34 | A1 | Se | B72 | V-35 | A1 | Se | B117 | V-36 | A1 | Se | B122 |
| V-37 | A1 | NMe | B1 | V-38 | A1 | NMe | B17 | V-39 | A1 | NMe | B27 |
| V-40 | A1 | NMe | B30 | V-41 | A1 | NMe | B54 | V-42 | A1 | NMe | B57 |
| V-43 | A1 | NMe | B58 | V-44 | A1 | NMe | B70 | V-45 | A1 | NMe | B71 |
| V-46 | A1 | NMe | B72 | V-47 | A1 | NMe | B117 | V-48 | A1 | NMe | B122 |
| V-49 | A2 | O | B1 | V-50 | A2 | O | B17 | V-51 | A2 | O | B27 |
| V-52 | A2 | O | B30 | V-53 | A2 | O | B54 | V-54 | A2 | O | B57 |
| V-55 | A2 | O | B58 | V-56 | A2 | O | B70 | V-57 | A2 | O | B71 |
| V-58 | A2 | O | B72 | V-59 | A2 | O | B117 | V-60 | A2 | O | B122 |
| V-61 | A2 | S | B1 | V-62 | A2 | S | B17 | V-63 | A2 | S | B27 |
| V-64 | A2 | S | B30 | V-65 | A2 | S | B54 | V-66 | A2 | S | B57 |
| V-67 | A2 | S | B58 | V-68 | A2 | S | B70 | V-69 | A2 | S | B71 |
| V-70 | A2 | S | B72 | V-71 | A2 | S | B117 | V-72 | A2 | S | B122 |
| V-73 | A2 | Se | B1 | V-74 | A2 | Se | B17 | V-75 | A2 | Se | B27 |
| V-76 | A2 | Se | B30 | V-77 | A2 | Se | B54 | V-78 | A2 | Se | B57 |
| V-79 | A2 | Se | B58 | V-80 | A2 | Se | B70 | V-81 | A2 | Se | B71 |
| V-82 | A2 | Se | B72 | V-83 | A2 | Se | B117 | V-84 | A2 | Se | B122 |
| V-85 | A3 | O | B1 | V-86 | A3 | O | B17 | V-87 | A3 | O | B27 |
| V-88 | A3 | O | B30 | V-89 | A3 | O | B54 | V-90 | A3 | O | B57 |
| V-91 | A3 | O | B58 | V-92 | A3 | O | B70 | V-93 | A3 | O | B71 |
| V-94 | A3 | O | B72 | V-95 | A3 | O | B117 | V-96 | A3 | O | B122 |

-continued

| No. | X | W | R | No. | X | W | R | No. | X | W | R |
|---|---|---|---|---|---|---|---|---|---|---|---|
| V-97 | A3 | S | B1 | V-98 | A3 | S | B17 | V-99 | A3 | S | B27 |
| V-100 | A3 | S | B30 | V-101 | A3 | S | B54 | V-102 | A3 | S | B57 |
| V-103 | A3 | S | B58 | V-104 | A3 | S | B70 | V-105 | A3 | S | B71 |
| V-106 | A3 | S | B72 | V-107 | A3 | S | B117 | V-108 | A3 | S | B122 | wherein Compound VI-1 to Compound VI-108 have a structure represented by Formula VI:

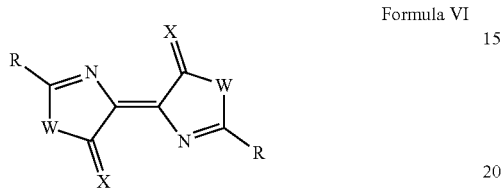

Formula VI in Formula VI, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| VI-1 | A1 | O | B1 | VI-2 | A1 | O | B17 | VI-3 | A1 | O | B27 |
| VI-4 | A1 | O | B30 | VI-5 | A1 | O | B54 | VI-6 | A1 | O | B57 |
| VI-7 | A1 | O | B58 | VI-8 | A1 | O | B70 | VI-9 | A1 | O | B71 |
| VI-10 | A1 | O | B72 | VI-11 | A1 | O | B117 | VI-12 | A1 | O | B122 |
| VI-13 | A1 | S | B1 | VI-14 | A1 | S | B17 | VI-15 | A1 | S | B27 |
| VI-16 | A1 | S | B30 | VI-17 | A1 | S | B54 | VI-18 | A1 | S | B57 |
| VI-19 | A1 | S | B58 | VI-20 | A1 | S | B70 | VI-21 | A1 | S | B71 |
| VI-22 | A1 | S | B72 | VI-23 | A1 | S | B117 | VI-24 | A1 | S | B122 |
| VI-25 | A1 | Se | B1 | VI-26 | A1 | Se | B17 | VI-27 | A1 | Se | B27 |
| VI-28 | A1 | Se | B30 | VI-29 | A1 | Se | B54 | VI-30 | A1 | Se | B57 |
| VI-31 | A1 | Se | B58 | VI-32 | A1 | Se | B70 | VI-33 | A1 | Se | B71 |
| VI-34 | A1 | Se | B72 | VI-35 | A1 | Se | B117 | VI-36 | A1 | Se | B122 |
| VI-37 | A1 | NMe | B1 | VI-38 | A1 | NMe | B17 | VI-39 | A1 | NMe | B27 |
| VI-40 | A1 | NMe | B30 | VI-41 | A1 | NMe | B54 | VI-42 | A1 | NMe | B57 |
| VI-43 | A1 | NMe | B58 | VI-44 | A1 | NMe | B70 | VI-45 | A1 | NMe | B71 |
| VI-46 | A1 | NMe | B72 | VI-47 | A1 | NMe | B117 | VI-48 | A1 | NMe | B122 |
| VI-49 | A2 | O | B1 | VI-50 | A2 | O | B17 | VI-51 | A2 | O | B27 |
| VI-52 | A2 | O | B30 | VI-53 | A2 | O | B54 | VI-54 | A2 | O | B57 |
| VI-55 | A2 | O | B58 | VI-56 | A2 | O | B70 | VI-57 | A2 | O | B71 |
| VI-58 | A2 | O | B72 | VI-59 | A2 | O | B117 | VI-60 | A2 | O | B122 |
| VI-61 | A2 | S | B1 | VI-62 | A2 | S | B17 | VI-63 | A2 | S | B27 |
| VI-64 | A2 | S | B30 | VI-65 | A2 | S | B54 | VI-66 | A2 | S | B57 |
| VI-67 | A2 | S | B58 | VI-68 | A2 | S | B70 | VI-69 | A2 | S | B71 |
| VI-70 | A2 | S | B72 | VI-71 | A2 | S | B117 | VI-72 | A2 | S | B122 |
| VI-73 | A2 | Se | B1 | VI-74 | A2 | Se | B17 | VI-75 | A2 | Se | B27 |
| VI-76 | A2 | Se | B30 | VI-77 | A2 | Se | B54 | VI-78 | A2 | Se | B57 |
| VI-79 | A2 | Se | B58 | VI-80 | A2 | Se | B70 | VI-81 | A2 | Se | B71 |
| VI-82 | A2 | Se | B72 | VI-83 | A2 | Se | B117 | VI-84 | A2 | Se | B122 |
| VI-85 | A3 | O | B1 | VI-86 | A3 | O | B17 | VI-87 | A3 | O | B27 |
| VI-88 | A3 | O | B30 | VI-89 | A3 | O | B54 | VI-90 | A3 | O | B57 |
| VI-91 | A3 | O | B58 | VI-92 | A3 | O | B70 | VI-93 | A3 | O | B71 |
| VI-94 | A3 | O | B72 | VI-95 | A3 | O | B117 | VI-96 | A3 | O | B122 |
| VI-97 | A3 | S | B1 | VI-98 | A3 | S | B17 | VI-99 | A3 | S | B27 |
| VI-100 | A3 | S | B30 | VI-101 | A3 | S | B54 | VI-102 | A3 | S | B57 |
| VI-103 | A3 | S | B58 | VI-104 | A3 | S | B70 | VI-105 | A3 | S | B71 |
| VI-106 | A3 | S | B72 | VI-107 | A3 | S | B117 | VI-108 | A3 | S | B122; | wherein Compound VII-1 to Compound VII-108 have a structure represented by Formula VII:

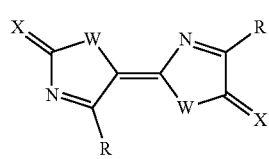

Formula VII in Formula VII, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| VII-1 | A1 | O | B1 | VII-2 | A1 | O | B17 | VII-3 | A1 | O | B27 |
| VII-4 | A1 | O | B30 | VII-5 | A1 | O | B54 | VII-6 | A1 | O | B57 |
| VII-7 | A1 | O | B58 | VII-8 | A1 | O | B70 | VII-9 | A1 | O | B71 |
| VII-10 | A1 | O | B72 | VII-11 | A1 | O | B117 | VII-12 | A1 | O | B122 |
| VII-13 | A1 | S | B1 | VII-14 | A1 | S | B17 | VII-15 | A1 | S | B27 |
| VII-16 | A1 | S | B30 | VII-17 | A1 | S | B54 | VII-18 | A1 | S | B57 |
| VII-19 | A1 | S | B58 | VII-20 | A1 | S | B70 | VII-21 | A1 | S | B71 |
| VII-22 | A1 | S | B72 | VII-23 | A1 | S | B117 | VII-24 | A1 | S | B122 |
| VII-25 | A1 | Se | B1 | VII-26 | A1 | Se | B17 | VII-27 | A1 | Se | B27 |
| VII-28 | A1 | Se | B30 | VII-29 | A1 | Se | B54 | VII-30 | A1 | Se | B57 |
| VII-31 | A1 | Se | B58 | VII-32 | A1 | Se | B70 | VII-33 | A1 | Se | B71 |
| VII-34 | A1 | Se | B72 | VII-35 | A1 | Se | B117 | VII-36 | A1 | Se | B122 |
| VII-37 | A1 | NMe | B1 | VII-38 | A1 | NMe | B17 | VII-39 | A1 | NMe | B27 |
| VII-40 | A1 | NMe | B30 | VII-41 | A1 | NMe | B54 | VII-42 | A1 | NMe | B57 |
| VII-43 | A1 | NMe | B58 | VII-44 | A1 | NMe | B70 | VII-45 | A1 | NMe | B71 |
| VII-46 | A1 | NMe | B72 | VII-47 | A1 | NMe | B117 | VII-48 | A1 | NMe | B122 |
| VII-49 | A2 | O | B1 | VII-50 | A2 | O | B17 | VII-51 | A2 | O | B27 |
| VII-52 | A2 | O | B30 | VII-53 | A2 | O | B54 | VII-54 | A2 | O | B57 |
| VII-55 | A2 | O | B58 | VII-56 | A2 | O | B70 | VII-57 | A2 | O | B71 |
| VII-58 | A2 | O | B72 | VII-59 | A2 | O | B117 | VII-60 | A2 | O | B122 |
| VII-61 | A2 | S | B1 | VII-62 | A2 | S | B17 | VII-63 | A2 | S | B27 |
| VII-64 | A2 | S | B30 | VII-65 | A2 | S | B54 | VII-66 | A2 | S | B57 |
| VII-67 | A2 | S | B58 | VII-68 | A2 | S | B70 | VII-69 | A2 | S | B71 |
| VII-70 | A2 | S | B72 | VII-71 | A2 | S | B117 | VII-72 | A2 | S | B122 |
| VII-73 | A2 | Se | B1 | VII-74 | A2 | Se | B17 | VII-75 | A2 | Se | B27 |
| VII-76 | A2 | Se | B30 | VII-77 | A2 | Se | B54 | VII-78 | A2 | Se | B57 |
| VII-79 | A2 | Se | B58 | VII-80 | A2 | Se | B70 | VII-81 | A2 | Se | B71 |
| VII-82 | A2 | Se | B72 | VII-83 | A2 | Se | B117 | VII-84 | A2 | Se | B122 |
| VII-85 | A3 | O | B1 | VII-86 | A3 | O | B17 | VII-87 | A3 | O | B27 |
| VII-88 | A3 | O | B30 | VII-89 | A3 | O | B54 | VII-90 | A3 | O | B57 |
| VII-91 | A3 | O | B58 | VII-92 | A3 | O | B70 | VII-93 | A3 | O | B71 |
| VII-94 | A3 | O | B72 | VII-95 | A3 | O | B117 | VII-96 | A3 | O | B122 |
| VII-97 | A3 | S | B1 | VII-98 | A3 | S | B17 | VII-99 | A3 | S | B27 |
| VII-100 | A3 | S | B30 | VII-101 | A3 | S | B54 | VII-102 | A3 | S | B57 |
| VII-103 | A3 | S | B58 | VII-104 | A3 | S | B70 | VII-105 | A3 | S | B71 |
| VII-106 | A3 | S | B72 | VII-107 | A3 | S | B117 | VII-108 | A3 | S | B122; | wherein Compound VIII-1 to Compound VIII-108 have a structure represented by Formula VIII:

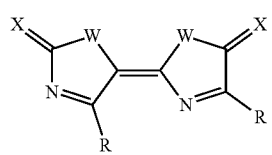

Formula VIII in Formula VIII, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| VIII-1 | A1 | O | B1 | VIII-2 | A1 | O | B17 | VIII-3 | A1 | O | B27 |
| VIII-4 | A1 | O | B30 | VIII-5 | A1 | O | B54 | VIII-6 | A1 | O | B57 |
| VIII-7 | A1 | O | B58 | VIII-8 | A1 | O | B70 | VIII-9 | A1 | O | B71 |
| VIII-10 | A1 | O | B72 | VIII-11 | A1 | O | B117 | VIII-12 | A1 | O | B122 |
| VIII-13 | A1 | S | B1 | VIII-14 | A1 | S | B17 | VIII-15 | A1 | S | B27 |
| VIII-16 | A1 | S | B30 | VIII-17 | A1 | S | B54 | VIII-18 | A1 | S | B57 |
| VIII-19 | A1 | S | B58 | VIII-20 | A1 | S | B70 | VIII-21 | A1 | S | B71 |
| VIII-22 | A1 | S | B72 | VIII-23 | A1 | S | B117 | VIII-24 | A1 | S | B122 |
| VIII-25 | A1 | Se | B1 | VIII-26 | A1 | Se | B17 | VIII-27 | A1 | Se | B27 |
| VIII-28 | A1 | Se | B30 | VIII-29 | A1 | Se | B54 | VIII-30 | A1 | Se | B57 |
| VIII-31 | A1 | Se | B58 | VIII-32 | A1 | Se | B70 | VIII-33 | A1 | Se | B71 |
| VIII-34 | A1 | Se | B72 | VIII-35 | A1 | Se | B117 | VIII-36 | A1 | Se | B122 |
| VIII-37 | A1 | NMe | B1 | VIII-38 | A1 | NMe | B17 | VIII-39 | A1 | NMe | B27 |
| VIII-40 | A1 | NMe | B30 | VIII-41 | A1 | NMe | B54 | VIII-42 | A1 | NMe | B57 |
| VIII-43 | A1 | NMe | B58 | VIII-44 | A1 | NMe | B70 | VIII-45 | A1 | NMe | B71 |
| VIII-46 | A1 | NMe | B72 | VIII-47 | A1 | NMe | B117 | VIII-48 | A1 | NMe | B122 |
| VIII-49 | A2 | O | B1 | VIII-50 | A2 | O | B17 | VIII-51 | A2 | O | B27 |
| VIII-52 | A2 | O | B30 | VIII-53 | A2 | O | B54 | VIII-54 | A2 | O | B57 |
| VIII-55 | A2 | O | B58 | VIII-56 | A2 | O | B70 | VIII-57 | A2 | O | B71 |
| VIII-58 | A2 | O | B72 | VIII-59 | A2 | O | B117 | VIII-60 | A2 | O | B122 |
| VIII-61 | A2 | S | B1 | VIII-62 | A2 | S | B17 | VIII-63 | A2 | S | B27 |
| VIII-64 | A2 | S | B30 | VIII-65 | A2 | S | B54 | VIII-66 | A2 | S | B57 |
| VIII-67 | A2 | S | B58 | VIII-68 | A2 | S | B70 | VIII-69 | A2 | S | B71 |
| VIII-70 | A2 | S | B72 | VIII-71 | A2 | S | B117 | VIII-72 | A2 | S | B122 |
| VIII-73 | A2 | Se | B1 | VIII-74 | A2 | Se | B17 | VIII-75 | A2 | Se | B27 |
| VIII-76 | A2 | Se | B30 | VIII-77 | A2 | Se | B54 | VIII-78 | A2 | Se | B57 |
| VIII-79 | A2 | Se | B58 | VIII-80 | A2 | Se | B70 | VIII-81 | A2 | Se | B71 |
| VIII-82 | A2 | Se | B72 | VIII-83 | A2 | Se | B117 | VIII-84 | A2 | Se | B122 |
| VIII-85 | A3 | O | B1 | VIII-86 | A3 | O | B17 | VIII-87 | A3 | O | B27 |
| VIII-88 | A3 | O | B30 | VIII-89 | A3 | O | B54 | VIII-90 | A3 | O | B57 |
| VIII-91 | A3 | O | B58 | VIII-92 | A3 | O | B70 | VIII-93 | A3 | O | B71 |
| VIII-94 | A3 | O | B72 | VIII-95 | A3 | O | B117 | VIII-96 | A3 | O | B122 |
| VIII-97 | A3 | S | B1 | VIII-98 | A3 | S | B17 | VIII-99 | A3 | S | B27 |
| VIII-100 | A3 | S | B30 | VIII-101 | A3 | S | B54 | VIII-102 | A3 | S | B57 |
| VIII-103 | A3 | S | B58 | VIII-104 | A3 | S | B70 | VIII-105 | A3 | S | B71 |
| VIII-106 | A3 | S | B72 | VIII-107 | A3 | S | B117 | VIII-108 | A3 | S | B122; | wherein Compound IX-1 to Compound IX-108 have a structure represented by Formula IX:

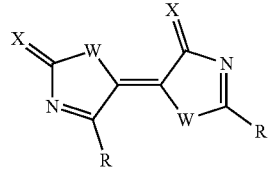

Formula IX in Formula IX, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| IX-1 | A1 | O | B1 | IX-2 | A1 | O | B17 | IX-3 | A1 | O | B27 |
| IX-4 | A1 | O | B30 | IX-5 | A1 | O | B54 | IX-6 | A1 | O | B57 |
| IX-7 | A1 | O | B58 | IX-8 | A1 | O | B70 | IX-9 | A1 | O | B71 |
| IX-10 | A1 | O | B72 | IX-11 | A1 | O | B117 | IX-12 | A1 | O | B122 |
| IX-13 | A1 | S | B1 | IX-14 | A1 | S | B17 | IX-15 | A1 | S | B27 |
| IX-16 | A1 | S | B30 | IX-17 | A1 | S | B54 | IX-18 | A1 | S | B57 |
| IX-19 | A1 | S | B58 | IX-20 | A1 | S | B70 | IX-21 | A1 | S | B71 |
| IX-22 | A1 | S | B72 | IX-23 | A1 | S | B117 | IX-24 | A1 | S | B122 |
| IX-25 | A1 | Se | B1 | IX-26 | A1 | Se | B17 | IX-27 | A1 | Se | B27 |
| IX-28 | A1 | Se | B30 | IX-29 | A1 | Se | B54 | IX-30 | A1 | Se | B57 |
| IX-31 | A1 | Se | B58 | IX-32 | A1 | Se | B70 | IX-33 | A1 | Se | B71 |
| IX-34 | A1 | Se | B72 | IX-35 | A1 | Se | B117 | IX-36 | A1 | Se | B122 |
| IX-37 | A1 | NMe | B1 | IX-38 | A1 | NMe | B17 | IX-39 | A1 | NMe | B27 |
| IX-40 | A1 | NMe | B30 | IX-41 | A1 | NMe | B54 | IX-42 | A1 | NMe | B57 |
| IX-43 | A1 | NMe | B58 | IX-44 | A1 | NMe | B70 | IX-45 | A1 | NMe | B71 |

-continued

| No. | X | W | R | No. | X | W | R | No. | X | W | R |
|---|---|---|---|---|---|---|---|---|---|---|---|
| IX-46 | A1 | NMe | B72 | IX-47 | A1 | NMe | B117 | IX-48 | A1 | NMe | B122 |
| IX-49 | A2 | O | B1 | IX-50 | A2 | O | B17 | IX-51 | A2 | O | B27 |
| IX-52 | A2 | O | B30 | IX-53 | A2 | O | B54 | IX-54 | A2 | O | B57 |
| IX-55 | A2 | O | B58 | IX-56 | A2 | O | B70 | IX-57 | A2 | O | B71 |
| IX-58 | A2 | O | B72 | IX-59 | A2 | O | B117 | IX-60 | A2 | O | B122 |
| IX-61 | A2 | S | B1 | IX-62 | A2 | S | B17 | IX-63 | A2 | S | B27 |
| IX-64 | A2 | S | B30 | IX-65 | A2 | S | B54 | IX-66 | A2 | S | B57 |
| IX-67 | A2 | S | B58 | IX-68 | A2 | S | B70 | IX-69 | A2 | S | B71 |
| IX-70 | A2 | S | B72 | IX-71 | A2 | S | B117 | IX-72 | A2 | S | B122 |
| IX-73 | A2 | Se | B1 | IX-74 | A2 | Se | B17 | IX-75 | A2 | Se | B27 |
| IX-76 | A2 | Se | B30 | IX-77 | A2 | Se | B54 | IX-78 | A2 | Se | B57 |
| IX-79 | A2 | Se | B58 | IX-80 | A2 | Se | B70 | IX-81 | A2 | Se | B71 |
| IX-82 | A2 | Se | B72 | IX-83 | A2 | Se | B117 | IX-84 | A2 | Se | B122 |
| IX-85 | A3 | O | B1 | IX-86 | A3 | O | B17 | IX-87 | A3 | O | B27 |
| IX-88 | A3 | O | B30 | IX-89 | A3 | O | B54 | IX-90 | A3 | O | B57 |
| IX-91 | A3 | O | B58 | IX-92 | A3 | O | B70 | IX-93 | A3 | O | B71 |
| IX-94 | A3 | O | B72 | IX-95 | A3 | O | B117 | IX-96 | A3 | O | B122 |
| IX-97 | A3 | S | B1 | IX-98 | A3 | S | B17 | IX-99 | A3 | S | B27 |
| IX-100 | A3 | S | B30 | IX-101 | A3 | S | B54 | IX-102 | A3 | S | B57 |
| IX-103 | A3 | S | B58 | IX-104 | A3 | S | B70 | IX-105 | A3 | S | B71 |
| IX-106 | A3 | S | B72 | IX-107 | A3 | S | B117 | IX-108 | A3 | S | B122; | wherein Compound X-1 to Compound X-108 have a structure represented by Formula X:

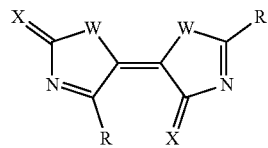

Formula X in Formula X, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| X-1 | A1 | O | B1 | X-2 | A1 | O | B17 | X-3 | A1 | O | B27 |
| X-4 | A1 | O | B30 | X-5 | A1 | O | B54 | X-6 | A1 | O | B57 |
| X-7 | A1 | O | B58 | X-8 | A1 | O | B70 | X-9 | A1 | O | B71 |
| X-10 | A1 | O | B72 | X-11 | A1 | O | B117 | X-12 | A1 | O | B122 |
| X-13 | A1 | S | B1 | X-14 | A1 | S | B17 | X-15 | A1 | S | B27 |
| X-16 | A1 | S | B30 | X-17 | A1 | S | B54 | X-18 | A1 | S | B57 |
| X-19 | A1 | S | B58 | X-20 | A1 | S | B70 | X-21 | A1 | S | B71 |
| X-22 | A1 | S | B72 | X-23 | A1 | S | B117 | X-24 | A1 | S | B122 |
| X-25 | A1 | Se | B1 | X-26 | A1 | Se | B17 | X-27 | A1 | Se | B27 |
| X-28 | A1 | Se | B30 | X-29 | A1 | Se | B54 | X-30 | A1 | Se | B57 |
| X-31 | A1 | Se | B58 | X-32 | A1 | Se | B70 | X-33 | A1 | Se | B71 |
| X-34 | A1 | Se | B72 | X-35 | A1 | Se | B117 | X-36 | A1 | Se | B122 |
| X-37 | A1 | NMe | B1 | X-38 | A1 | NMe | B17 | X-39 | A1 | NMe | B27 |
| X-40 | A1 | NMe | B30 | X-41 | A1 | NMe | B54 | X-42 | A1 | NMe | B57 |
| X-43 | A1 | NMe | B58 | X-44 | A1 | NMe | B70 | X-45 | A1 | NMe | B71 |
| X-46 | A1 | NMe | B72 | X-47 | A1 | NMe | B117 | X-48 | A1 | NMe | B122 |
| X-49 | A2 | O | B1 | X-50 | A2 | O | B17 | X-51 | A2 | O | B27 |
| X-52 | A2 | O | B30 | X-53 | A2 | O | B54 | X-54 | A2 | O | B57 |
| X-55 | A2 | O | B58 | X-56 | A2 | O | B70 | X-57 | A2 | O | B71 |
| X-58 | A2 | O | B72 | X-59 | A2 | O | B117 | X-60 | A2 | O | B122 |
| X-61 | A2 | S | B1 | X-62 | A2 | S | B17 | X-63 | A2 | S | B27 |
| X-64 | A2 | S | B30 | X-65 | A2 | S | B54 | X-66 | A2 | S | B57 |
| X-67 | A2 | S | B58 | X-68 | A2 | S | B70 | X-69 | A2 | S | B71 |
| X-70 | A2 | S | B72 | X-71 | A2 | S | B117 | X-72 | A2 | S | B122 |
| X-73 | A2 | Se | B1 | X-74 | A2 | Se | B17 | X-75 | A2 | Se | B27 |
| X-76 | A2 | Se | B30 | X-77 | A2 | Se | B54 | X-78 | A2 | Se | B57 |
| X-79 | A2 | Se | B58 | X-80 | A2 | Se | B70 | X-81 | A2 | Se | B71 |
| X-82 | A2 | Se | B72 | X-83 | A2 | Se | B117 | X-84 | A2 | Se | B122 |
| X-85 | A3 | O | B1 | X-86 | A3 | O | B17 | X-87 | A3 | O | B27 |
| X-88 | A3 | O | B30 | X-89 | A3 | O | B54 | X-90 | A3 | O | B57 |

-continued

| No. | X | W | R | No. | X | W | R | No. | X | W | R |
|---|---|---|---|---|---|---|---|---|---|---|---|
| X-91 | A3 | O | B58 | X-92 | A3 | O | B70 | X-93 | A3 | O | B71 |
| X-94 | A3 | O | B72 | X-95 | A3 | O | B117 | X-96 | A3 | O | B122 |
| X-97 | A3 | S | B1 | X-98 | A3 | S | B17 | X-99 | A3 | S | B27 |
| X-100 | A3 | S | B30 | X-101 | A3 | S | B54 | X-102 | A3 | S | B57 |
| X-103 | A3 | S | B58 | X-104 | A3 | S | B70 | X-105 | A3 | S | B71 |
| X-106 | A3 | S | B72 | X-107 | A3 | S | B117 | X-108 | A3 | S | B122; | wherein Compound XI-1 to Compound XI-108 have a structure represented by Formula XI:

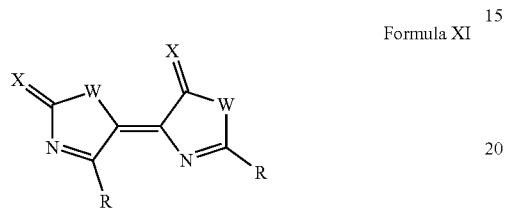

Formula XI in Formula XI, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| XI-1 | A1 | O | B1 | XI-2 | A1 | O | B17 | XI-3 | A1 | O | B27 |
| XI-4 | A1 | O | B30 | XI-5 | A1 | O | B54 | XI-6 | A1 | O | B57 |
| XI-7 | A1 | O | B58 | XI-8 | A1 | O | B70 | XI-9 | A1 | O | B71 |
| XI-10 | A1 | O | B72 | XI-11 | A1 | O | B117 | XI-12 | A1 | O | B122 |
| XI-13 | A1 | S | B1 | XI-14 | A1 | S | B17 | XI-15 | A1 | S | B27 |
| XI-16 | A1 | S | B30 | XI-17 | A1 | S | B54 | XI-18 | A1 | S | B57 |
| XI-19 | A1 | S | B58 | XI-20 | A1 | S | B70 | XI-21 | A1 | S | B71 |
| XI-22 | A1 | S | B72 | XI-23 | A1 | S | B117 | XI-24 | A1 | S | B122 |
| XI-25 | A1 | Se | B1 | XI-26 | A1 | Se | B17 | XI-27 | A1 | Se | B27 |
| XI-28 | A1 | Se | B30 | XI-29 | A1 | Se | B54 | XI-30 | A1 | Se | B57 |
| XI-31 | A1 | Se | B58 | XI-32 | A1 | Se | B70 | XI-33 | A1 | Se | B71 |
| XI-34 | A1 | Se | B72 | XI-35 | A1 | Se | B117 | XI-36 | A1 | Se | B122 |
| XI-37 | A1 | NMe | B1 | XI-38 | A1 | NMe | B17 | XI-39 | A1 | NMe | B27 |
| XI-40 | A1 | NMe | B30 | XI-41 | A1 | NMe | B54 | XI-42 | A1 | NMe | B57 |
| XI-43 | A1 | NMe | B58 | XI-44 | A1 | NMe | B70 | XI-45 | A1 | NMe | B71 |
| XI-46 | A1 | NMe | B72 | XI-47 | A1 | NMe | B117 | XI-48 | A1 | NMe | B122 |
| XI-49 | A2 | O | B1 | XI-50 | A2 | O | B17 | XI-51 | A2 | O | B27 |
| XI-52 | A2 | O | B30 | XI-53 | A2 | O | B54 | XI-54 | A2 | O | B57 |
| XI-55 | A2 | O | B58 | XI-56 | A2 | O | B70 | XI-57 | A2 | O | B71 |
| XI-58 | A2 | O | B72 | XI-59 | A2 | O | B117 | XI-60 | A2 | O | B122 |
| XI-61 | A2 | S | B1 | XI-62 | A2 | S | B17 | XI-63 | A2 | S | B27 |
| XI-64 | A2 | S | B30 | XI-65 | A2 | S | B54 | XI-66 | A2 | S | B57 |
| XI-67 | A2 | S | B58 | XI-68 | A2 | S | B70 | XI-69 | A2 | S | B71 |
| XI-70 | A2 | S | B72 | XI-71 | A2 | S | B117 | XI-72 | A2 | S | B122 |
| XI-73 | A2 | Se | B1 | XI-74 | A2 | Se | B17 | XI-75 | A2 | Se | B27 |
| XI-76 | A2 | Se | B30 | XI-77 | A2 | Se | B54 | XI-78 | A2 | Se | B57 |
| XI-79 | A2 | Se | B58 | XI-80 | A2 | Se | B70 | XI-81 | A2 | Se | B71 |
| XI-82 | A2 | Se | B72 | XI-83 | A2 | Se | B117 | XI-84 | A2 | Se | B122 |
| XI-85 | A3 | O | B1 | XI-86 | A3 | O | B17 | XI-87 | A3 | O | B27 |
| XI-88 | A3 | O | B30 | XI-89 | A3 | O | B54 | XI-90 | A3 | O | B57 |
| XI-91 | A3 | O | B58 | XI-92 | A3 | O | B70 | XI-93 | A3 | O | B71 |
| XI-94 | A3 | O | B72 | XI-95 | A3 | O | B117 | XI-96 | A3 | O | B122 |
| XI-97 | A3 | S | B1 | XI-98 | A3 | S | B17 | XI-99 | A3 | S | B27 |
| XI-100 | A3 | S | B30 | XI-101 | A3 | S | B54 | XI-102 | A3 | S | B57 |
| XI-103 | A3 | S | B58 | XI-104 | A3 | S | B70 | XI-105 | A3 | S | B71 |
| XI-106 | A3 | S | B72 | XI-107 | A3 | S | B117 | XI-108 | A3 | S | B122; | wherein Compound XII-1 to Compound XII-108 have a structure represented by Formula XII:

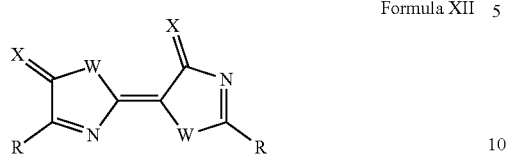

Formula XII in Formula XII, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| XII-1 | A1 | O | B1 | XII-2 | A1 | O | B17 | XII-3 | A1 | O | B27 |
| XII-4 | A1 | O | B30 | XII-5 | A1 | O | B54 | XII-6 | A1 | O | B57 |
| XII-7 | A1 | O | B58 | XII-8 | A1 | O | B70 | XII-9 | A1 | O | B71 |
| XII-10 | A1 | O | B72 | XII-11 | A1 | O | B117 | XII-12 | A1 | O | B122 |
| XII-13 | A1 | S | B1 | XII-14 | A1 | S | B17 | XII-15 | A1 | S | B27 |
| XII-16 | A1 | S | B30 | XII-17 | A1 | S | B54 | XII-18 | A1 | S | B57 |
| XII-19 | A1 | S | B58 | XII-20 | A1 | S | B70 | XII-21 | A1 | S | B71 |
| XII-22 | A1 | S | B72 | XII-23 | A1 | S | B117 | XII-24 | A1 | S | B122 |
| XII-25 | A1 | Se | B1 | XII-26 | A1 | Se | B17 | XII-27 | A1 | Se | B27 |
| XII-28 | A1 | Se | B30 | XII-29 | A1 | Se | B54 | XII-30 | A1 | Se | B57 |
| XII-31 | A1 | Se | B58 | XII-32 | A1 | Se | B70 | XII-33 | A1 | Se | B71 |
| XII-34 | A1 | Se | B72 | XII-35 | A1 | Se | B117 | XII-36 | A1 | Se | B122 |
| XII-37 | A1 | NMe | B1 | XII-38 | A1 | NMe | B17 | XII-39 | A1 | NMe | B27 |
| XII-40 | A1 | NMe | B30 | XII-41 | A1 | NMe | B54 | XII-42 | A1 | NMe | B57 |
| XII-43 | A1 | NMe | B58 | XII-44 | A1 | NMe | B70 | XII-45 | A1 | NMe | B71 |
| XII-46 | A1 | NMe | B72 | XII-47 | A1 | NMe | B117 | XII-48 | A1 | NMe | B122 |
| XII-49 | A2 | O | B1 | XII-50 | A2 | O | B17 | XII-51 | A2 | O | B27 |
| XII-52 | A2 | O | B30 | XII-53 | A2 | O | B54 | XII-54 | A2 | O | B57 |
| XII-55 | A2 | O | B58 | XII-56 | A2 | O | B70 | XII-57 | A2 | O | B71 |
| XII-58 | A2 | O | B72 | XII-59 | A2 | O | B117 | XII-60 | A2 | O | B122 |
| XII-61 | A2 | S | B1 | XII-62 | A2 | S | B17 | XII-63 | A2 | S | B27 |
| XII-64 | A2 | S | B30 | XII-65 | A2 | S | B54 | XII-66 | A2 | S | B57 |
| XII-67 | A2 | S | B58 | XII-68 | A2 | S | B70 | XII-69 | A2 | S | B71 |
| XII-70 | A2 | S | B72 | XII-71 | A2 | S | B117 | XII-72 | A2 | S | B122 |
| XII-73 | A2 | Se | B1 | XII-74 | A2 | Se | B17 | XII-75 | A2 | Se | B27 |
| XII-76 | A2 | Se | B30 | XII-77 | A2 | Se | B54 | XII-78 | A2 | Se | B57 |
| XII-79 | A2 | Se | B58 | XII-80 | A2 | Se | B70 | XII-81 | A2 | Se | B71 |
| XII-82 | A2 | Se | B72 | XII-83 | A2 | Se | B117 | XII-84 | A2 | Se | B122 |
| XII-85 | A3 | O | B1 | XII-86 | A3 | O | B17 | XII-87 | A3 | O | B27 |
| XII-88 | A3 | O | B30 | XII-89 | A3 | O | B54 | XII-90 | A3 | O | B57 |
| XII-91 | A3 | O | B58 | XII-92 | A3 | O | B70 | XII-93 | A3 | O | B71 |
| XII-94 | A3 | O | B72 | XII-95 | A3 | O | B117 | XII-96 | A3 | O | B122 |
| XII-97 | A3 | S | B1 | XII-98 | A3 | S | B17 | XII-99 | A3 | S | B27 |
| XII-100 | A3 | S | B30 | XII-101 | A3 | S | B54 | XII-102 | A3 | S | B57 |
| XII-103 | A3 | S | B58 | XII-104 | A3 | S | B70 | XII-105 | A3 | S | B71 |
| XII-106 | A3 | S | B72 | XII-107 | A3 | S | B117 | XII-108 | A3 | S | B122; | wherein Compound XIII-1 to Compound XIII-108 have a structure represented by Formula XIII:

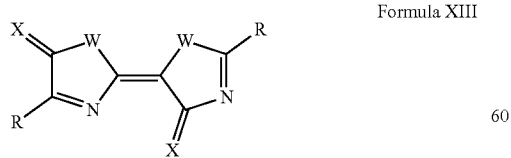

Formula XIII in Formula XIII, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| XII-1 | A1 | O | B1 | XIII-2 | A1 | O | B17 | XIII-3 | A1 | O | B27 |
| XIII-4 | A1 | O | B30 | XIII-5 | A1 | O | B54 | XIII-6 | A1 | O | B57 |
| XIII-7 | A1 | O | B58 | XIII-8 | A1 | O | B70 | XIII-9 | A1 | O | B71 |
| XIII-10 | A1 | O | B72 | XIII-11 | A1 | O | B117 | XIII-12 | A1 | O | B122 |
| XIII-13 | A1 | S | B1 | XIII-14 | A1 | S | B17 | XIII-15 | A1 | S | B27 |
| XIII-16 | A1 | S | B30 | XIII-17 | A1 | S | B54 | XIII-18 | A1 | S | B57 |
| XIII-19 | A1 | S | B58 | XIII-20 | A1 | S | B70 | XIII-21 | A1 | S | B71 |
| XIII-22 | A1 | S | B72 | XIII-23 | A1 | S | B117 | XIII-24 | A1 | S | B122 |
| XIII-25 | A1 | Se | B1 | XIII-26 | A1 | Se | B17 | XIII-27 | A1 | Se | B27 |
| XIII-28 | A1 | Se | B30 | XIII-29 | A1 | Se | B54 | XIII-30 | A1 | Se | B57 |
| XIII-31 | A1 | Se | B58 | XIII-32 | A1 | Se | B70 | XIII-33 | A1 | Se | B71 |
| XIII-34 | A1 | Se | B72 | XIII-35 | A1 | Se | B117 | XIII-36 | A1 | Se | B122 |
| XIII-37 | A1 | NMe | B1 | XIII-38 | A1 | NMe | B17 | XIII-39 | A1 | NMe | B27 |
| XIII-40 | A1 | NMe | B30 | XIII-41 | A1 | NMe | B54 | XIII-42 | A1 | NMe | B57 |
| XIII-43 | A1 | NMe | B58 | XIII-44 | A1 | NMe | B70 | XIII-45 | A1 | NMe | B71 |
| XIII-46 | A1 | NMe | B72 | XIII-47 | A1 | NMe | B117 | XIII-48 | A1 | NMe | B122 |
| XIII-49 | A2 | O | B1 | XIII-50 | A2 | O | B17 | XIII-51 | A2 | O | B27 |
| XIII-52 | A2 | O | B30 | XIII-53 | A2 | O | B54 | XIII-54 | A2 | O | B57 |
| XIII-55 | A2 | O | B58 | XIII-56 | A2 | O | B70 | XIII-57 | A2 | O | B71 |
| XIII-58 | A2 | O | B72 | XIII-59 | A2 | O | B117 | XIII-60 | A2 | O | B122 |
| XIII-61 | A2 | S | B1 | XIII-62 | A2 | S | B17 | XIII-63 | A2 | S | B27 |
| XIII-64 | A2 | S | B30 | XIII-65 | A2 | S | B54 | XIII-66 | A2 | S | B57 |
| XIII-67 | A2 | S | B58 | XIII-68 | A2 | S | B70 | XIII-69 | A2 | S | B71 |
| XIII-70 | A2 | S | B72 | XIII-71 | A2 | S | B117 | XIII-72 | A2 | S | B122 |
| XIII-73 | A2 | Se | B1 | XIII-74 | A2 | Se | B17 | XIII-75 | A2 | Se | B27 |
| XIII-76 | A2 | Se | B30 | XIII-77 | A2 | Se | B54 | XIII-78 | A2 | Se | B57 |
| XIII-79 | A2 | Se | B58 | XIII-80 | A2 | Se | B70 | XIII-81 | A2 | Se | B71 |
| XIII-82 | A2 | Se | B72 | XIII-83 | A2 | Se | B117 | XIII-84 | A2 | Se | B122 |
| XIII-85 | A3 | O | B1 | XIII-86 | A3 | O | B17 | XIII-87 | A3 | O | B27 |
| XIII-88 | A3 | O | B30 | XIII-89 | A3 | O | B54 | XIII-90 | A3 | O | B57 |
| XIII-91 | A3 | O | B58 | XIII-92 | A3 | O | B70 | XIII-93 | A3 | O | B71 |
| XIII-94 | A3 | O | B72 | XIII-95 | A3 | O | B117 | XIII-96 | A3 | O | B122 |
| XIII-97 | A3 | S | B1 | XIII-98 | A3 | S | B17 | XIII-99 | A3 | S | B27 |
| XIII-100 | A3 | S | B30 | XIII-101 | A3 | S | B54 | XIII-102 | A3 | S | B57 |
| XIII-103 | A3 | S | B58 | XIII-104 | A3 | S | B70 | XIII-105 | A3 | S | B71 |
| XIII-106 | A3 | S | B72 | XIII-107 | A3 | S | B117 | XIII-108 | A3 | S | B122; | wherein Compound XIV-1 to Compound XIV-108 have a structure represented by Formula XIV:

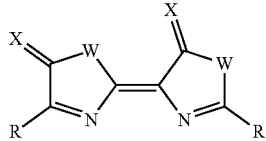

Formula XIV in Formula XIV, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| XIV-1 | A1 | O | B1 | XIV-2 | A1 | O | B17 | XIV-3 | A1 | O | B27 |
| XIV-4 | A1 | O | B30 | XIV-5 | A1 | O | B54 | XIV-6 | A1 | O | B57 |
| XIV-7 | A1 | O | B58 | XIV-8 | A1 | O | B70 | XIV-9 | A1 | O | B71 |
| XIV-10 | A1 | O | B72 | XIV-11 | A1 | O | B117 | XIV-12 | A1 | O | B122 |
| XIV-13 | A1 | S | B1 | XIV-14 | A1 | S | B17 | XIV-15 | A1 | S | B27 |
| XIV-16 | A1 | S | B30 | XIV-17 | A1 | S | B54 | XIV-18 | A1 | S | B57 |
| XIV-19 | A1 | S | B58 | XIV-20 | A1 | S | B70 | XIV-21 | A1 | S | B71 |
| XIV-22 | A1 | S | B72 | XIV-23 | A1 | S | B117 | XIV-24 | A1 | S | B122 |
| XIV-25 | A1 | Se | B1 | XIV-26 | A1 | Se | B17 | XIV-27 | A1 | Se | B27 |
| XIV-28 | A1 | Se | B30 | XIV-29 | A1 | Se | B54 | XIV-30 | A1 | Se | B57 |
| XIV-31 | A1 | Se | B58 | XIV-32 | A1 | Se | B70 | XIV-33 | A1 | Se | B71 |
| XIV-34 | A1 | Se | B72 | XIV-35 | A1 | Se | B117 | XIV-36 | A1 | Se | B122 |
| XIV-37 | A1 | NMe | B1 | XIV-38 | A1 | NMe | B17 | XIV-39 | A1 | NMe | B27 |
| XIV-40 | A1 | NMe | B30 | XIV-41 | A1 | NMe | B54 | XIV-42 | A1 | NMe | B57 |
| XIV-43 | A1 | NMe | B58 | XIV-44 | A1 | NMe | B70 | XIV-45 | A1 | NMe | B71 |
| XIV-46 | A1 | NMe | B72 | XIV-47 | A1 | NMe | B117 | XIV-48 | A1 | NMe | B122 |
| XIV-49 | A2 | O | B1 | XIV-50 | A2 | O | B17 | XIV-51 | A2 | O | B27 |

-continued

| No. | X | W | R | No. | X | W | R | No. | X | W | R |
|---|---|---|---|---|---|---|---|---|---|---|---|
| XIV-52 | A2 | O | B30 | XIV-53 | A2 | O | B54 | XIV-54 | A2 | O | B57 |
| XIV-55 | A2 | O | B58 | XIV-56 | A2 | O | B70 | XIV-57 | A2 | O | B71 |
| XIV-58 | A2 | O | B72 | XIV-59 | A2 | O | B117 | XIV-60 | A2 | O | B122 |
| XIV-61 | A2 | S | B1 | XIV-62 | A2 | S | B17 | XIV-63 | A2 | S | B27 |
| XIV-64 | A2 | S | B30 | XIV-65 | A2 | S | B54 | XIV-66 | A2 | S | B57 |
| XIV-67 | A2 | S | B58 | XIV-68 | A2 | S | B70 | XIV-69 | A2 | S | B71 |
| XIV-70 | A2 | S | B72 | XIV-71 | A2 | S | B117 | XIV-72 | A2 | S | B122 |
| XIV-73 | A2 | Se | B1 | XIV-74 | A2 | Se | B17 | XIV-75 | A2 | Se | B27 |
| XIV-76 | A2 | Se | B30 | XIV-77 | A2 | Se | B54 | XIV-78 | A2 | Se | B57 |
| XIV-79 | A2 | Se | B58 | XIV-80 | A2 | Se | B70 | XIV-81 | A2 | Se | B71 |
| XIV-82 | A2 | Se | B72 | XIV-83 | A2 | Se | B117 | XIV-84 | A2 | Se | B122 |
| XIV-85 | A3 | O | B1 | XIV-86 | A3 | O | B17 | XIV-87 | A3 | O | B27 |
| XIV-88 | A3 | O | B30 | XIV-89 | A3 | O | B54 | XIV-90 | A3 | O | B57 |
| XIV-91 | A3 | O | B58 | XIV-92 | A3 | O | B70 | XIV-93 | A3 | O | B71 |
| XIV-94 | A3 | O | B72 | XIV-95 | A3 | O | B117 | XIV-96 | A3 | O | B122 |
| XIV-97 | A3 | S | B1 | XIV-98 | A3 | S | B17 | XIV-99 | A3 | S | B27 |
| XIV-100 | A3 | S | B30 | XIV-101 | A3 | S | B54 | XIV-102 | A3 | S | B57 |
| XIV-103 | A3 | S | B58 | XIV-104 | A3 | S | B70 | XIV-105 | A3 | S | B71 |
| XIV-106 | A3 | S | B72 | XIV-107 | A3 | S | B117 | XIV-108 | A3 | S | B122; | wherein Compound XV-1 to Compound XV-108 have a structure represented by Formula XV:

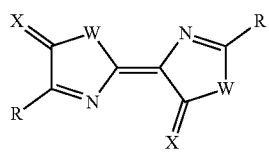

Formula XV in Formula XV, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| XV-1 | A1 | O | B1 | XV-2 | A1 | O | B17 | XV-3 | A1 | O | B27 |
| XV-4 | A1 | O | B30 | XV-5 | A1 | O | B54 | XV-6 | A1 | O | B57 |
| XV-7 | A1 | O | B58 | XV-8 | A1 | O | B70 | XV-9 | A1 | O | B71 |
| XV-10 | A1 | O | B72 | XV-11 | A1 | O | B117 | XV-12 | A1 | O | B122 |
| XV-13 | A1 | S | B1 | XV-14 | A1 | S | B17 | XV-15 | A1 | S | B27 |
| XV-16 | A1 | S | B30 | XV-17 | A1 | S | B54 | XV-18 | A1 | S | B57 |
| XV-19 | A1 | S | B58 | XV-20 | A1 | S | B70 | XV-21 | A1 | S | B71 |
| XV-22 | A1 | S | B72 | XV-23 | A1 | S | B117 | XV-24 | A1 | S | B122 |
| XV-25 | A1 | Se | B1 | XV-26 | A1 | Se | B17 | XV-27 | A1 | Se | B27 |
| XV-28 | A1 | Se | B30 | XV-29 | A1 | Se | B54 | XV-30 | A1 | Se | B57 |
| XV-31 | A1 | Se | B58 | XV-32 | A1 | Se | B70 | XV-33 | A1 | Se | B71 |
| XV-34 | A1 | Se | B72 | XV-35 | A1 | Se | B117 | XV-36 | A1 | Se | B122 |
| XV-37 | A1 | NMe | B1 | XV-38 | A1 | NMe | B17 | XV-39 | A1 | NMe | B27 |
| XV-40 | A1 | NMe | B30 | XV-41 | A1 | NMe | B54 | XV-42 | A1 | NMe | B57 |
| XV-43 | A1 | NMe | B58 | XV-44 | A1 | NMe | B70 | XV-45 | A1 | NMe | B71 |
| XV-46 | A1 | NMe | B72 | XV-47 | A1 | NMe | B117 | XV-48 | A1 | NMe | B122 |
| XV-49 | A2 | O | B1 | XV-50 | A2 | O | B17 | XV-51 | A2 | O | B27 |
| XV-52 | A2 | O | B30 | XV-53 | A2 | O | B54 | XV-54 | A2 | O | B57 |
| XV-55 | A2 | O | B58 | XV-56 | A2 | O | B70 | XV-57 | A2 | O | B71 |
| XV-58 | A2 | O | B72 | XV-59 | A2 | O | B117 | XV-60 | A2 | O | B122 |
| XV-61 | A2 | S | B1 | XV-62 | A2 | S | B17 | XV-63 | A2 | S | B27 |
| XV-64 | A2 | S | B30 | XV-65 | A2 | S | B54 | XV-66 | A2 | S | B57 |
| XV-67 | A2 | S | B58 | XV-68 | A2 | S | B70 | XV-69 | A2 | S | B71 |
| XV-70 | A2 | S | B72 | XV-71 | A2 | S | B117 | XV-72 | A2 | S | B122 |
| XV-73 | A2 | Se | B1 | XV-74 | A2 | Se | B17 | XV-75 | A2 | Se | B27 |
| XV-76 | A2 | Se | B30 | XV-77 | A2 | Se | B54 | XV-78 | A2 | Se | B57 |
| XV-79 | A2 | Se | B58 | XV-80 | A2 | Se | B70 | XV-81 | A2 | Se | B71 |
| XV-82 | A2 | Se | B72 | XV-83 | A2 | Se | B117 | XV-84 | A2 | Se | B122 |
| XV-85 | A3 | O | B1 | XV-86 | A3 | O | B17 | XV-87 | A3 | O | B27 |
| XV-88 | A3 | O | B30 | XV-89 | A3 | O | B54 | XV-90 | A3 | O | B57 |
| XV-91 | A3 | O | B58 | XV-92 | A3 | O | B70 | XV-93 | A3 | O | B71 |
| XV-94 | A3 | O | B72 | XV-95 | A3 | O | B117 | XV-96 | A3 | O | B122 |

-continued

| No. | X | W | R | No. | X | W | R | No. | X | W | R |
|---|---|---|---|---|---|---|---|---|---|---|---|
| XV-97 | A3 | S | B1 | XV-98 | A3 | S | B17 | XV-99 | A3 | S | B27 |
| XV-100 | A3 | S | B30 | XV-101 | A3 | S | B54 | XV-102 | A3 | S | B57 |
| XV-103 | A3 | S | B58 | XV-104 | A3 | S | B70 | XV-105 | A3 | S | B71 |
| XV-106 | A3 | S | B72 | XV-107 | A3 | S | B117 | XV-108 | A3 | S | B122; | wherein Compound XVI-1 to Compound XVI-108 have a structure represented by Formula XVI:

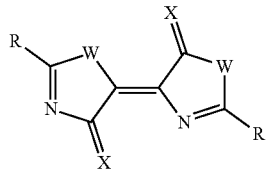

Formula XVI in Formula XVI, two X are identical, two W are identical, two R are identical, and X, W, and R correspond to an atom or a group selected from the following table, respectively:

| No. | X | W | R | No. | X | W | R | No. | X | W | R |
|---|---|---|---|---|---|---|---|---|---|---|---|
| XVI-1 | A1 | O | B1 | XVI-2 | A1 | O | B17 | XVI-3 | A1 | O | B27 |
| XVI-4 | A1 | O | B30 | XVI-5 | A1 | O | B54 | XVI-6 | A1 | O | B57 |
| XVI-7 | A1 | O | B58 | XVI-8 | A1 | O | B70 | XVI-9 | A1 | O | B71 |
| XVI-10 | A1 | O | B72 | XVI-11 | A1 | O | B117 | XVI-12 | A1 | O | B122 |
| XVI-13 | A1 | S | B1 | XVI-14 | A1 | S | B17 | XVI-15 | A1 | S | B27 |
| XVI-16 | A1 | S | B30 | XVI-17 | A1 | S | B54 | XVI-18 | A1 | S | B57 |
| XVI-19 | A1 | S | B58 | XVI-20 | A1 | S | B70 | XVI-21 | A1 | S | B71 |
| XVI-22 | A1 | S | B72 | XVI-23 | A1 | S | B117 | XVI-24 | A1 | S | B122 |
| XVI-25 | A1 | Se | B1 | XVI-26 | A1 | Se | B17 | XVI-27 | A1 | Se | B27 |
| XVI-28 | A1 | Se | B30 | XVI-29 | A1 | Se | B54 | XVI-30 | A1 | Se | B57 |
| XVI-31 | A1 | Se | B58 | XVI-32 | A1 | Se | B70 | XVI-33 | A1 | Se | B71 |
| XVI-34 | A1 | Se | B72 | XVI-35 | A1 | Se | B117 | XVI-36 | A1 | Se | B122 |
| XVI-37 | A1 | NMe | B1 | XVI-38 | A1 | NMe | B17 | XVI-39 | A1 | NMe | B27 |
| XVI-40 | A1 | NMe | B30 | XVI-41 | A1 | NMe | B54 | XVI-42 | A1 | NMe | B57 |
| XVI-43 | A1 | NMe | B58 | XVI-44 | A1 | NMe | B70 | XVI-45 | A1 | NMe | B71 |
| XVI-46 | A1 | NMe | B72 | XVI-47 | A1 | NMe | B117 | XVI-48 | A1 | NMe | B122 |
| XVI-49 | A2 | O | B1 | XVI-50 | A2 | O | B17 | XVI-51 | A2 | O | B27 |
| XVI-52 | A2 | O | B30 | XVI-53 | A2 | O | B54 | XVI-54 | A2 | O | B57 |
| XVI-55 | A2 | O | B58 | XVI-56 | A2 | O | B70 | XVI-57 | A2 | O | B71 |
| XVI-58 | A2 | O | B72 | XVI-59 | A2 | O | B117 | XVI-60 | A2 | O | B122 |
| XVI-61 | A2 | S | B1 | XVI-62 | A2 | S | B17 | XVI-63 | A2 | S | B27 |
| XVI-64 | A2 | S | B30 | XVI-65 | A2 | S | B54 | XVI-66 | A2 | S | B57 |
| XVI-67 | A2 | S | B58 | XVI-68 | A2 | S | B70 | XVI-69 | A2 | S | B71 |
| XVI-70 | A2 | S | B72 | XVI-71 | A2 | S | B117 | XVI-72 | A2 | S | B122 |
| XVI-73 | A2 | Se | B1 | XVI-74 | A2 | Se | B17 | XVI-75 | A2 | Se | B27 |
| XVI-76 | A2 | Se | B30 | XVI-77 | A2 | Se | B54 | XVI-78 | A2 | Se | B57 |
| XVI-79 | A2 | Se | B58 | XVI-80 | A2 | Se | B70 | XVI-81 | A2 | Se | B71 |
| XVI-82 | A2 | Se | B72 | XVI-83 | A2 | Se | B117 | XVI-84 | A2 | Se | B122 |
| XVI-85 | A3 | O | B1 | XVI-86 | A3 | O | B17 | XVI-87 | A3 | O | B27 |
| XVI-88 | A3 | O | B30 | XVI-89 | A3 | O | B54 | XVI-90 | A3 | O | B57 |
| XVI-91 | A3 | O | B58 | XVI-92 | A3 | O | B70 | XVI-93 | A3 | O | B71 |
| XVI-94 | A3 | O | B72 | XVI-95 | A3 | O | B117 | XVI-96 | A3 | O | B122 |
| XVI-97 | A3 | S | B1 | XVI-98 | A3 | S | B17 | XVI-99 | A3 | S | B27 |
| XVI-100 | A3 | S | B30 | XVI-101 | A3 | S | B54 | XVI-102 | A3 | S | B57 |
| XVI-103 | A3 | S | B58 | XVI-104 | A3 | S | B70 | XVI-105 | A3 | S | B71 |
| XVI-106 | A3 | S | B72 | XVI-107 | A3 | S | B117 | XVI-108 | A3 | S | B122; | wherein Compound LIO-1 to Compound LIO-108 have a structure represented by Formula LIO:

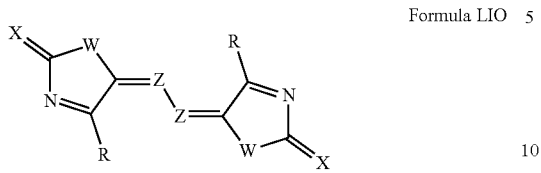

Formula LIO in Formula LIO, two X are identical, two W are identical, two R are identical, two Z are identical and are $CR_L$, and X, W, R, and $R_L$ correspond to an atom or a group selected from the following table, respectively:

| No. | X | W | R | $R_L$ | No. | X | W | R | $R_L$ | No. | X | W | R | $R_L$ |
|---|---|---|---|---|---|---|---|---|---|---|---|---|---|---|
| LIO-1 | A1 | O | B1 | H | LIO-2 | A1 | O | B17 | H | LIO-3 | A1 | O | B25 | H |
| LIO-4 | A1 | O | B54 | H | LIO-5 | A1 | O | B70 | H | LIO-6 | A1 | O | B72 | H |
| LIO-7 | A1 | S | B1 | H | LIO-8 | A1 | S | B17 | H | LIO-9 | A1 | S | B25 | H |
| LIO-10 | A1 | S | B54 | H | LIO-11 | A1 | S | B70 | H | LIO-12 | A1 | S | B72 | H |
| LIO-13 | A1 | Se | B54 | H | LIO-14 | A1 | Se | B70 | H | LIO-15 | A1 | Se | B72 | H |
| LIO-16 | A1 | NMe | B54 | H | LIO-17 | A1 | NMe | B70 | H | LIO-18 | A1 | NMe | B72 | H |
| LIO-19 | A1 | O | H | F | LIO-20 | A1 | O | B17 | F | LIO-21 | A1 | O | B25 | F |
| LIO-22 | A1 | O | B54 | F | LIO-23 | A1 | O | B70 | F | LIO-24 | A1 | O | B72 | F |
| LIO-25 | A1 | S | H | F | LIO-26 | A1 | S | B17 | F | LIO-27 | A1 | S | B25 | F |
| LIO-28 | A1 | S | B54 | F | LIO-29 | A1 | S | B70 | F | LIO-30 | A1 | S | B72 | F |
| LIO-31 | A1 | O | H | B6 | LIO-32 | A1 | O | B17 | B6 | LIO-33 | A1 | O | B25 | B6 |
| LIO-34 | A1 | O | B54 | B6 | LIO-35 | A1 | O | B70 | B6 | LIO-36 | A1 | O | B72 | B6 |
| LIO-37 | A1 | S | B1 | B6 | LIO-38 | A1 | S | B17 | B6 | LIO-39 | A1 | S | B25 | B6 |
| LIO-40 | A1 | S | B54 | B6 | LIO-41 | A1 | S | B70 | B6 | LIO-42 | A1 | S | B72 | B6 |
| LIO-43 | A1 | O | H | B70 | LIO-44 | A1 | O | B17 | B70 | LIO-45 | A1 | O | B25 | B70 |
| LIO-46 | A1 | O | B54 | B70 | LIO-47 | A1 | O | B70 | B70 | LIO-48 | A1 | O | B72 | B70 |
| LIO-49 | A1 | S | B1 | B70 | LIO-50 | A1 | S | B17 | B70 | LIO-51 | A1 | S | B25 | B70 |
| LIO-52 | A1 | S | B54 | B70 | LIO-53 | A1 | S | B70 | B70 | LIO-54 | A1 | S | B72 | B70 |
| LIO-55 | A2 | O | B1 | H | LIO-56 | A2 | O | B17 | H | LIO-57 | A2 | O | B25 | H |
| LIO-58 | A2 | O | B54 | H | LIO-59 | A2 | O | B70 | H | LIO-60 | A2 | O | B72 | H |
| LIO-61 | A2 | S | B1 | H | LIO-62 | A2 | S | B17 | H | LIO-63 | A2 | S | B25 | H |
| LIO-64 | A2 | S | B54 | H | LIO-65 | A2 | S | B70 | H | LIO-66 | A2 | S | B72 | H |
| LIO-67 | A2 | O | B54 | F | LIO-68 | A2 | O | B70 | F | LIO-69 | A2 | O | B72 | F |
| LIO-70 | A2 | S | B54 | F | LIO-71 | A2 | S | B70 | F | LIO-72 | A2 | S | B72 | F |
| LIO-73 | A2 | O | B54 | B6 | LIO-74 | A2 | O | B70 | B6 | LIO-75 | A2 | O | B72 | B6 |
| LIO-76 | A2 | S | B54 | B6 | LIO-77 | A2 | S | B70 | B6 | LIO-78 | A2 | S | B72 | B6 |
| LIO-79 | A2 | O | B54 | B70 | LIO-80 | A2 | O | B70 | B70 | LIO-81 | A2 | O | B72 | B70 |
| LIO-82 | A3 | O | B1 | H | LIO-83 | A3 | O | B17 | H | LIO-84 | A3 | O | B25 | H |
| LIO-85 | A3 | O | B54 | H | LIO-86 | A3 | O | B70 | H | LIO-87 | A3 | O | B72 | H |
| LIO-88 | A3 | S | B1 | H | LIO-89 | A3 | S | B17 | H | LIO-90 | A3 | S | B25 | H |
| LIO-91 | A3 | S | B54 | H | LIO-92 | A3 | S | B70 | H | LIO-93 | A3 | S | B72 | H |
| LIO-94 | A3 | O | B54 | F | LIO-95 | A3 | O | B70 | F | LIO-96 | A3 | O | B72 | F |
| LIO-97 | A3 | S | B54 | F | LIO-98 | A3 | S | B70 | F | LIO-99 | A3 | S | B72 | F |
| LIO-100 | A3 | O | B54 | B6 | LIO-101 | A3 | O | B70 | B6 | LIO-102 | A3 | O | B72 | B6 |
| LIO-103 | A3 | S | B54 | B6 | LIO-104 | A3 | S | B70 | B6 | LIO-105 | A3 | S | B72 | B6 |
| LIO-106 | A3 | O | B54 | B70 | LIO-107 | A3 | O | B70 | B70 | LIO-108 | A3 | O | B72 | B70; | wherein Compound LIOA-1 to Compound LIOA-66 have a structure represented by Formula LIOA:

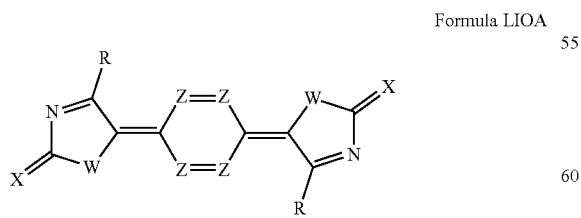

Formula LIOA in Formula LIOA, two X are identical, two W are identical, two R are identical, four Z are identical and are $CR_L$, and X, W, R, and $R_L$ correspond to an atom or a group selected from the following table, respectively:

| No. | X | W | R | $R_L$ | No. | X | W | R | $R_L$ | No. | X | W | R | $R_L$ |
|---|---|---|---|---|---|---|---|---|---|---|---|---|---|---|
| LIOA-1 | A1 | O | B1 | H | LIOA-2 | A1 | O | B17 | H | LIOA-3 | A1 | O | B54 | H |
| LIOA-4 | A1 | O | B57 | H | LIOA-5 | A1 | O | B70 | H | LIOA-6 | A1 | O | B72 | H |
| LIOA-7 | A1 | S | B1 | H | LIOA-8 | A1 | S | B17 | H | LIOA-9 | A1 | S | B25 | H |
| LIOA-10 | A1 | S | B54 | H | LIOA-11 | A1 | S | B70 | H | LIOA-12 | A1 | S | B72 | H |
| LIOA-13 | A1 | Se | B54 | H | LIOA-14 | A1 | Se | B70 | H | LIOA-15 | A1 | Se | B72 | H |
| LIOA-16 | A1 | NMe | B54 | H | LIOA-17 | A1 | NMe | B70 | H | LIOA-18 | A1 | NMe | B72 | H |
| LIOA-19 | A1 | O | H | F | LIOA-20 | A1 | O | B17 | F | LIOA-21 | A1 | O | B54 | F |
| LIOA-22 | A1 | O | B57 | F | LIOA-23 | A1 | O | B70 | F | LIOA-24 | A1 | O | B72 | F |
| LIOA-25 | A1 | S | H | F | LIOA-26 | A1 | S | B17 | F | LIOA-27 | A1 | S | B25 | F |
| LIOA-28 | A1 | S | B54 | F | LIOA-29 | A1 | S | B70 | F | LIOA-30 | A1 | S | B72 | F |
| LIOA-31 | A2 | O | B1 | H | LIOA-32 | A2 | O | B17 | H | LIOA-33 | A2 | O | B25 | H |
| LIOA-34 | A2 | O | B54 | H | LIOA-35 | A2 | O | B70 | H | LIOA-36 | A2 | O | B72 | H |
| LIOA-37 | A2 | S | B1 | H | LIOA-38 | A2 | S | B17 | H | LIOA-39 | A2 | S | B25 | H |
| LIOA-40 | A2 | S | B54 | H | LIOA-41 | A2 | S | B70 | H | LIOA-42 | A2 | S | B72 | H |
| LIOA-43 | A2 | O | B54 | F | LIOA-44 | A2 | O | B70 | F | LIOA-45 | A2 | O | B72 | F |
| LIOA-46 | A2 | S | B54 | F | LIOA-47 | A2 | S | B70 | F | LIOA-48 | A2 | S | B72 | F |
| LIOA-49 | A3 | O | B1 | H | LIOA-50 | A3 | O | B17 | H | LIOA-51 | A3 | O | B25 | H |
| LIOA-52 | A3 | O | B54 | H | LIOA-53 | A3 | O | B70 | H | LIOA-54 | A3 | O | B72 | H |
| LIOA-55 | A3 | S | B1 | H | LIOA-56 | A3 | S | B17 | H | LIOA-57 | A3 | S | B25 | H |
| LIOA-58 | A3 | S | B54 | H | LIOA-59 | A3 | S | B70 | H | LXVO-60 | A3 | S | B72 | H |
| LIOA-61 | A3 | O | B54 | F | LIOA-62 | A3 | O | B70 | F | LIOA-63 | A3 | O | B72 | F |
| LIOA-64 | A3 | S | B54 | F | LIOA-65 | A3 | S | B70 | F | LIOA-66 | A3 | S | B72 | F; | wherein Compound II-IO-1 to Compound II-IO-60 have a structure represented by Formula II-IO:

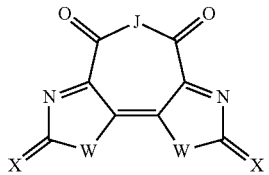

Formula II-IO in Formula II-IO, two X are identical, two W are identical, J is $NR_{NJ}$, and X, W, and $R_{NJ}$ correspond to an atom or a group selected from the following table, respectively:

| No. | X | W | $R_{NJ}$ | No. | X | W | $R_{NJ}$ | No. | X | W | $R_{NJ}$ |
|---|---|---|---|---|---|---|---|---|---|---|---|---|
| II-IO-1 | A1 | O | B14 | II-IO-2 | A1 | O | B16 | II-IO-3 | A1 | O | B18 |
| II-IO-4 | A1 | O | B25 | II-IO-5 | A1 | O | B57 | II-IO-6 | A1 | O | B58 |
| II-IO-7 | A1 | O | B70 | II-IO-8 | A1 | O | B71 | II-IO-9 | A1 | O | B117 |
| II-IO-10 | A1 | S | B14 | II-IO-11 | A1 | S | B16 | II-IO-12 | A1 | S | B18 |
| II-IO-13 | A1 | S | B25 | II-IO-14 | A1 | S | B57 | II-IO-15 | A1 | S | B58 |
| II-IO-16 | A1 | S | B70 | II-IO-17 | A1 | S | B71 | II-IO-18 | A1 | S | B117 |
| II-IO-19 | A1 | Se | B25 | II-IO-20 | A1 | Se | B57 | II-IO-21 | A1 | Se | B58 |
| II-IO-22 | A1 | Se | B70 | II-IO-23 | A1 | Se | B71 | II-IO-24 | A1 | Se | B117 |
| II-IO-25 | A2 | O | B14 | II-IO-26 | A2 | O | B16 | II-IO-27 | A2 | O | B18 |
| II-IO-28 | A2 | O | B25 | II-IO-29 | A2 | O | B57 | II-IO-30 | A2 | O | B58 |
| II-IO-31 | A2 | O | B70 | II-IO-32 | A2 | O | B71 | II-IO-33 | A2 | O | B117 |
| II-IO-34 | A2 | S | B25 | II-IO-35 | A2 | S | B57 | II-IO-36 | A2 | S | B58 |
| II-IO-37 | A2 | S | B70 | II-IO-38 | A2 | S | B71 | II-IO-39 | A2 | S | B117 |
| II-IO-40 | A2 | Se | B25 | II-IO-41 | A2 | Se | B57 | II-IO-42 | A2 | Se | B58 |
| II-IO-43 | A3 | O | B14 | II-IO-44 | A3 | O | B16 | II-IO-45 | A3 | O | B18 |
| II-IO-46 | A3 | O | B25 | II-IO-47 | A3 | O | B57 | II-IO-48 | A3 | O | B58 |
| II-IO-49 | A3 | O | B70 | II-IO-50 | A3 | O | B71 | II-IO-51 | A3 | O | B117 |
| II-IO-52 | A3 | S | B25 | II-IO-53 | A3 | S | B57 | II-IO-54 | A3 | S | B58 |
| II-IO-55 | A3 | S | B70 | II-IO-56 | A3 | S | B71 | II-IO-57 | A3 | S | B117 |
| II-IO-58 | A3 | Se | B25 | II-IO-59 | A3 | Se | B57 | II-IO-60 | A3 | Se | B58. |

21. An electroluminescent device, comprising:
an anode,
a cathode, and
an organic layer disposed between the anode and the cathode, wherein the organic layer comprises the compound according to claim 1.

22. The electroluminescent device according to claim 21, wherein the organic layer is a hole injection layer or a hole transporting layer, and the hole injection layer or the hole transporting layer is formed by the compound alone;
or the hole injection layer or the hole transporting layer further comprises at least one hole transporting material; wherein the molar doping ratio of the compound to the hole transporting material ranges from 10000:1 to 1:10000; and preferably, the molar ratio of the compound to the hole transporting material ranges from 10:1 to 1:100.

23. The electroluminescent device according to claim 21, wherein the electroluminescent device comprises a plurality of stack layers between the anode and the cathode, and the plurality of stack layers comprise a first emissive layer and a second emissive layer, wherein a first stack layer comprises the first emissive layer, a second stack layer comprises the second emissive layer, and a charge generation layer is disposed between the first stack layer and the second stack layer, wherein the charge generation layer comprises a p-type charge generation layer and an n-type charge generation layer;

wherein the p-type charge generation layer comprises the compound; preferably, the p-type charge generation layer further comprises at least one hole transporting material, wherein the molar doping ratio of the compound to the hole transporting material ranges from 10000:1 to 1:10000; preferably, wherein the molar doping ratio of the compound to the hole transporting material ranges from 10:1 to 1:100.

24. The electroluminescent device according to claim 22, wherein the hole transporting material comprises a compound having a triarylamine unit, a spirodifluorene compound, a pentacene compound, an oligothiophene compound, an oligomeric phenyl compound, an oligomeric phenylenevinylene compound, an oligomeric fluorene compound, a porphyrin complex or a metal phthalocyanine complex.

25. The electroluminescent device according to claim 23, wherein the charge generation layer further comprises a buffer layer disposed between the p-type charge generation layer and the N-type charge generation layer, and the buffer layer comprises the compound.

26. The electroluminescent device according to claim 21, wherein the electroluminescent device is prepared by vacuum evaporation.

27. A compound formulation, comprising the compound according to claim 1.

* * * * *